(12) United States Patent
Connolly et al.

(10) Patent No.: US 7,196,090 B2
(45) Date of Patent: Mar. 27, 2007

(54) KINASE INHIBITORS

(75) Inventors: Cleo J. Chivikas Connolly, Livonia, MI (US); Christopher James Deur, Ann Arbor, MI (US); James Marino Hamby, Ann Arbor, MI (US); Denton Wade Hoyer, Dexter, MI (US); Chris Limberakis, Saline, MI (US); Jessica Elizabeth Reed, Ann Arbor, MI (US); Mel Conrad Schroeder, Dexter, MI (US); Clarke Taylor, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 346 days.

(21) Appl. No.: 10/621,983

(22) Filed: Jul. 17, 2003

(65) Prior Publication Data

US 2004/0019210 A1 Jan. 29, 2004

Related U.S. Application Data

(60) Provisional application No. 60/398,638, filed on Jul. 25, 2002.

(51) Int. Cl.
*A01N 43/54* (2006.01)
*A61K 31/505* (2006.01)
*C07D 487/00* (2006.01)

(52) U.S. Cl. ...................................... 514/258; 544/256
(58) Field of Classification Search ................ 514/258; 544/256
See application file for complete search history.

(56) References Cited

U.S. PATENT DOCUMENTS

| | | |
|---|---|---|
| 2,949,466 A | 8/1960 | Hoefle et al. |
| 3,912,723 A | 10/1975 | Miller |
| 4,425,346 A | 1/1984 | Harlington |
| 4,886,807 A | 12/1989 | Kitamura et al. |
| 5,654,307 A | 8/1997 | Bridges et al. |
| 6,084,095 A | 7/2000 | Bridges et al. |

FOREIGN PATENT DOCUMENTS

| | | |
|---|---|---|
| WO | WO 96/13262 A1 | 5/1996 |
| WO | WO 96/15128 A2 | 5/1996 |
| WO | WO 96/34867 A1 | 11/1996 |
| WO | WO 97/38983 A1 | 10/1997 |
| WO | WO 99/61444 | * 12/1999 |
| WO | WO 99/61444 A2 | 12/1999 |
| WO | WO 00/24744 A1 | 5/2000 |
| WO | WO 01/29041 | * 4/2001 |
| WO | WO 01/29041 A1 | 4/2001 |
| WO | WO 01/29042 | * 4/2001 |
| WO | WO 01/29042 A1 | 4/2001 |
| WO | WO 01/64679 A1 | 9/2001 |

OTHER PUBLICATIONS

Adachi, K., "Synthesis of Orcinol Monomethl Ether", Memoirs of the Osaka Institute of Technology, Series A, 1983 pp. 33-42, vol. 28, No. 1.

* cited by examiner

*Primary Examiner*—James O. Wilson
*Assistant Examiner*—Paul V. Ward
(74) *Attorney, Agent, or Firm*—Steve Eck; Wendy Hsu; Eric Baude

(57) ABSTRACT

This invention provides phenyl-substituted pyrimidopyrimidines, dihydropyrimido-pyrimidines, pyridopyrimidines, naphthyridines, and pyridopyrazines of the general formula:

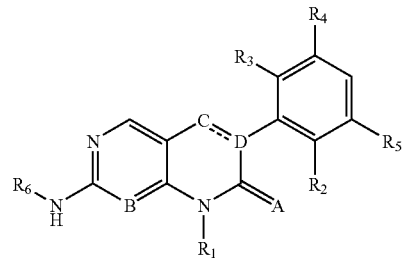

that inhibit cyclin-dependent kinase and tyrosine kinase enzymes, methods and intermediate compounds for their synthesis, as well as pharmaceutical compositions and methods for their use in treating, inhibiting or preventing maladies associated with cell proliferative disorders, including angiogenesis, atherosclerosis, restenosis, and cancer.

10 Claims, No Drawings

KINASE INHIBITORS

This application is a Non-Provisional Utility Application, which claims priority to U.S. provisional application Ser. No. 60/398,638, filed Jul. 25, 2002.

FIELD OF THE INVENTION

This invention relates to substituted pyrimidopyrimidines, dihydropyrimidopyrimidines, pyridopyrimidines, naphthyridines and pyridopyrazines that inhibit cyclin-dependent kinase and tyrosine kinase enzymes, and as such are useful to treat cell proliferative disorders such as angiogenesis, atherosclerosis, restenosis, and cancer.

BACKGROUND OF THE INVENTION

Tyrosine kinases are an integral part of growth factor receptors and are essential for the propagation of growth factor signal transduction leading to cellular proliferation, differentiation, and migration. Growth factor receptors are also known as receptor tyrosine kinases (RTKs). The aberrant regulation of growth factors or their cognate receptors are reputed to play a critical role in the progression of proliferative diseases. Fibroblast growth factor (FGF) and vascular endothelial growth factor (VEGF) have been implicated as important mediators of tumor promoted angiogenesis. Solid tumors are dependent upon the formation of new blood vessels from preexisting vessels (angiogenesis) to nourish their growth and to provide a conduit for metastases. Accordingly, inhibitors of the FGF and VEGF RTKs, as well as other tyrosine kinases, are useful agents for the prevention and treatment of proliferative diseases dependent on these enzymes.

WO 00/24744 (Harris et al.), WO 96/13262 (Thompson et al.), WO 01/64679 (Adams et al.), WO 01/29041 and WO 01/29042 (both to Dunn et al.) teach pyrimidopyrimidinone compounds useful in treating proliferative diseases.

Despite the progress that has been made, the search continues for small molecular weight compounds that are orally bioavailable and useful for treating a wide variety of human tumors and other proliferative disorders such as restenosis, angiogenesis, diabetic retinopathy, and atherosclerosis.

SUMMARY OF THE INVENTION

This invention comprises compounds of the formula:

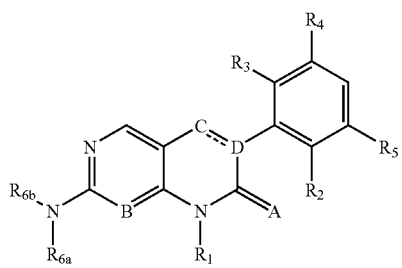

wherein:

A is O, $NH_2$, $NH(C_1-C_6$ alkyl), $N(C_1-C_6$ alkyl$)_2$, or —NHC(O)—$NHR_{12}$;

$R_{12}$ is $C_1-C_6$ straight or branched chain alkyl, preferably $C_1-C_4$ straight or branched chain alkyl, or —$(CH_2)_n$— $C_3-C_8$ cycloalkyl ring, preferably —$(CH_2)_n$—$C_3-C_7$ cycloalkyl, wherein n is an integer of from 1 to 3;

B, C, and D are independently selected from CH or N, with the proviso that C and D are not both N;

$R_1$ is selected from the group of $C_1-C_6$ straight or branched chain alkyl, preferably $C_1-C_4$ straight or branched chain alkyl, optionally substituted by —COOH, or;

a) a phenyl, benzyl or $C_3-C_8$ cycloalkyl group, preferably $C_3-C_7$ cycloalkyl, or —$CH_2$—$C_3-C_8$ cycloalkyl group, preferably —$CH_2$—$C_3-C_7$ cycloalkyl, with the rings of the phenyl, benzyl or cycloalkyl groups being optionally substituted by 1 or 2 COOH or —$CH_2$—COOH groups; or b) a piperidine or piperazine moiety selected from group of:

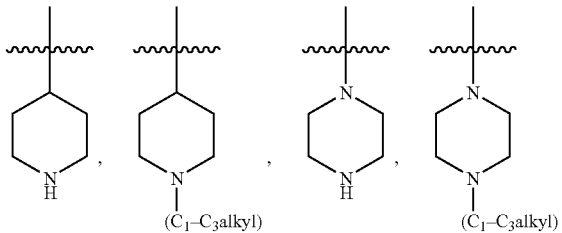

the rings of the piperidine or piperazine moieties being optionally substituted by 1 or 2 COOH or —$CH_2$—COOH groups; or c) a tetrahydropyran or morpholine moiety of the formulae:

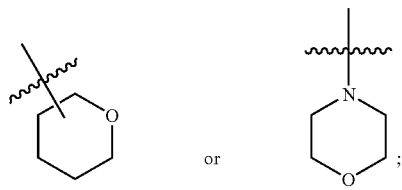

$R_2$ is H, Cl or F;

$R_3$ is H, Cl or F, with the proviso that at least one of $R_2$ or $R_3$ is F;

$R_4$ is H, OH, —$OCH_3$, or —$OCH_2CH_3$, with the proviso that, if $R_4$ is H, $R_2$ and $R_3$ are not H;

$R_5$ is —$OCH_3$, or —$OCH_2CH_3$;

$R_{6a}$ is selected from H or $C_1-C_6$ alkyl, preferably $C_1-C_3$ alkyl;

$R_{6b}$ is selected from the group of H, —$(C_1-C_5$ alkyl)-$NH_2$, —$(C_1-C_5$ alkyl)-NH—$(C_1-C_3$ alkyl)-$R_{11}$, —$(C_1-C_5$ alkyl)-N—$(C_1-C_3$ alkyl-$R_{11})_2$, —O—$(C_1-C_5$ alkyl)-$NH_2$, —O—$(C_1-C_5$ alkyl)-NH—$(C_1-C_3$ alkyl)-$R_{11}$, —O—$(C_1-C_5$ alkyl)-N—$(C_1-C_3$ alkyl-$R_{11})_2$, —$CH(CH_2OH)_2$, —$(C_1-C_3$ alkyl)-$(CH_2OH)_2$, —$(C_1-C_3$ alkyl)-O—$(C_1-C_3$ alkyl)-$R_{11}$, —$(C_1-C_3$ alkyl)-O—$(C_1-C_3$ alkyl)-$NH_2$, —$(C_1-C_3$ alkyl)-O—$(C_1-C_3$ alkyl)-NH—$(C_1-C_3$ alkyl)-$R_{11}$, —$(C_1-C_3$ alkyl)-O—$(C_1-C_3$ alkyl)-N($C_1-C_3$ alkyl-$R_{11})_2$, phenyl substituted by 1 or 2 groups selected from $NH_2$, —N($C_1-C_3$ alkyl), —N($C_1-C_3$ alkyl$)_2$, CN or —$(C_1-C_3$ alkyl)-tetrazole, or $C_1-C_6$ alkyl,

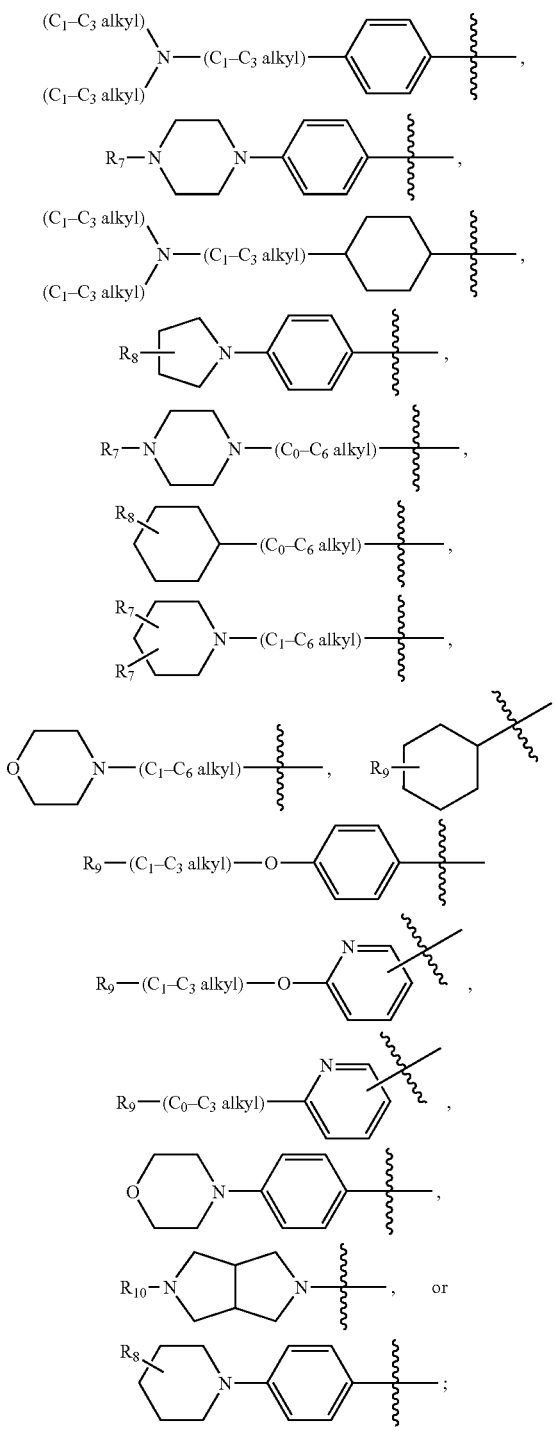

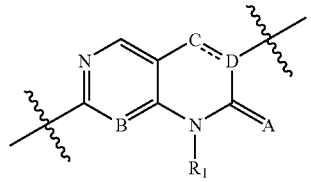

$R_{10}$ is H or $C_1$–$C_3$ alkyl;

$R_{11}$ is H, CN, OH, $NH_2$, F, or $CF_3$;

or a pharmaceutically acceptable salt or ester form thereof.

This invention also includes subgroups of the compounds described above in which the core structure designated:

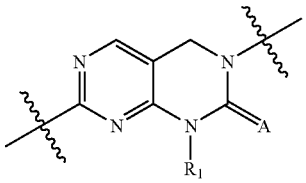

is selected independently in each subgroup from the moieties:

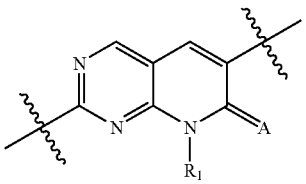

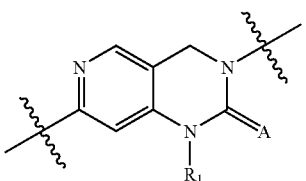

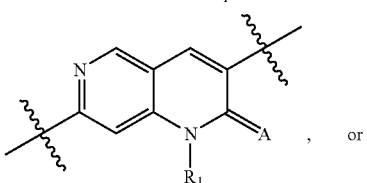

, or

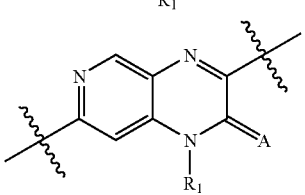

;

with each of the alkyl chains of any group in this $R_4$ definition being optionally substituted by from 1 to 4 OH groups;

$R_7$ in each instance is independently selected from H, —$NH_2$, $NH(C_1$–$C_3$ alkyl), $N(C_1$–$C_3$ alkyl)$_2$, or $C_1$–$C_3$ alkyl;

$R_8$ is H, OH or $C_1$–$C_3$ alkyl;

$R_9$ is H, OH, —$NH_2$, $NH(C_1$–$C_3$ alkyl), or $N(C_1$–$C_3$ alkyl)$_2$;

wherein, in each case, the variables A, $R_1$, $R_2$, $R_3$, $R_4$, $R_5$, $R_6$, $R_7$, $R_8$, $R_9$, $R_{10}$, $R_{11}$, and $R_{12}$ are as defined above. It will be understood that the dashed lines in the structures above indicate an optional double bond at the position indicated.

Within each of the groups and subgroups described herein is another subgroup of compounds of this invention wherein the variable A is O. Another subgroup within each group or subgroup of compounds comprises those wherein A is selected from $NH_2$, $NH(C_1$–$C_6$ alkyl) or $N(C_1$–$C_6$ alkyl)$_2$. A further subgroup therein comprises those compounds wherein A is selected from $NH_2$, $NH(C_1-C_3$ alkyl) or $N(C_1-C_3$ alkyl$)_2$.

In each description of compounds herein it is understood the moiety designated by the structure:

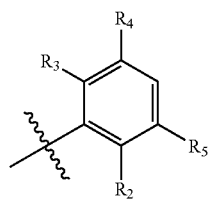

includes, but is not limited to, the representative groups 2,6-difluoro-3,5-dimethoxy-phenyl; 2,6-difluoro-3,5-diethoxy-phenyl; 3-ethoxy-2,6-difluoro-5-methoxy-phenyl; 2-fluoro-3,5-dimethoxy-phenyl; 2-fluoro-3,5-diethoxy-phenyl; 3-ethoxy-2-fluoro-5-methoxy-phenyl; 5-ethoxy-2-fluoro-3-methoxy-phenyl; 5-methoxy-2,6-difluoro-3-hydroxy-phenyl; 2-fluoro-3-hydroxy-5-methoxy-phenyl; 2-fluoro-3-methoxy-5-hydroxy-phenyl; 2-fluoro-3-hydroxy-5-ethoxy-phenyl; 2-fluoro-3-ethoxy-5-hydroxy-phenyl; 2,6-difluoro-3-methoxy-phenyl, 2,6-difluoro-3-ethoxyphenyl, 2,6-difluoro-3-ethoxy-phenyl, 2-chloro-6-fluoro-3,5-dimethoxy-phenyl, 2-chloro-5-ethoxy-6-fluoro-3-methoxy-phenyl, 2-chloro-3-ethoxy-6-fluoro-5-methoxy-phenyl, 2-chloro-3-ethoxy-6-fluoro-5-hydroxy-phenyl, 2-chloro-3-methoxy-6-fluoro-5-hydroxy-phenyl, 2-fluoro-3-methoxy-6-chloro-5-hydroxy-phenyl, 2-chloro-6-fluoro-3-methoxy-phenyl, or 6-chloro-3-ethoxy-2-fluoro-phenyl. Within each of the groups of compounds described herein is a subgroup wherein one of $R_2$ and $R_3$ is H and the other is F, and $R_4$ and $R_5$ are as defined above. In another subgroup within each group or subgroup described herein, $R_2$ and $R_3$ are both F and $R_4$ and $R_5$ are as defined above.

Within each compound description herein also exists a further subgroup in which $R_1$ is selected from $C_1-C_6$ straight or branched chain alkyl, preferably $C_1-C_4$ straight or branched chain alkyl, optionally substituted by —COOH, or a benzyl or $C_3-C_8$ cycloalkyl ring, preferably $C_3-C_7$ cycloalkyl, with the benzyl or cycloalkyl rings being optionally substituted by 1 or 2 COOH groups.

One group of compounds of this invention comprises those of the formula:

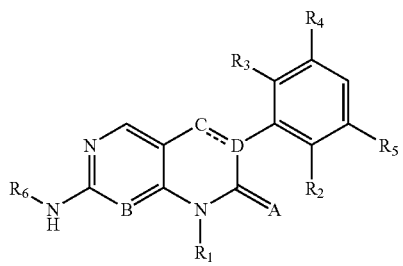

wherein:

A is O , $NH_2$, $NH(C_1-C_6$ alkyl), $N(C_1-C_6$ alkyl$)_2$, or —NHC(O)—$NHR_{12}$;

$R_{12}$ is $C_1-C_6$ straight or branched chain alkyl, preferably $C_1-C_4$ straight or branched chain alkyl, or —$(CH_2)_n$— $C_3-C_8$ cycloalkyl ring, preferably —$(CH_2)_n$—$C_3-C_7$ cycloalkyl, wherein n is an integer of from 1 to 3;

B, C, and D are independently selected from CH or N, with the proviso that C and D are not both N;

$R_1$ is selected from the group of $C_1-C_6$ straight or branched chain alkyl, preferably $C_1-C_4$ straight or branched chain alkyl, optionally substituted by —COOH, or;

c) a phenyl, benzyl, or $C_3-C_8$ cycloalkyl ring, preferably $C_3-C_7$ cycloalkyl, or —$CH_2$—$C_3-C_8$ cycloalkyl ring, preferably —$CH_2$—$C_3-C_7$ cycloalkyl, with the phenyl, benzyl or cycloalkyl rings being optionally substituted by 1 or 2 COOH or —$CH_2$—COOH groups;

$R_2$ is H or F;

$R_3$ is H or F, with the proviso that at least one of $R_2$ or $R_3$ is F;

$R_4$ is H, OH, —$OCH_3$, or —$OCH_2CH_3$, with the proviso that, if $R_4$ is H, $R_2$ and $R_3$ are not H;

$R_5$ is —$OCH_3$, or —$OCH_2CH_3$;

$R_6$ is selected from the group of H, —$(C_1-C_5$ alkyl)-$NH_2$, —$(C_1-C_5$ alkyl)-NH—$(C_1-C_3$ alkyl)-$R_{11}$, —$(C_1-C_5$ alkyl)-N—$(C_1-C_3$ alkyl-$R_{11})_2$, —O—$(C_1-C_5$ alkyl)-$NH_2$, —O—$(C_1-C_5$ alkyl)-NH—$(C_1-C_3$ alkyl)-$R_{11}$, —O—$(C_1-C_5$ alkyl)-N—$(C_1-C_3$ alkyl-$R_{11})_2$, —$CH(CH_2OH)_2$, —$(C_1-C_3$ alkyl)-$(CH_2OH)_2$, —$(C_1-C_3$ alkyl)-O—$(C_1-C_3$ alkyl)-$R_{11}$, —$(C_1-C_3$ alkyl)-O—$(C_1-C_3$ alkyl)-$NH_2$, —$(C_1-C_3$ alkyl)-O—$(C_1-C_3$ alkyl)-NH—$(C_1-C_3$ alkyl)-$R_{11}$, —$(C_1-C_3$ alkyl)-O—$(C_1-C_3$ alkyl)-N$(C_1-C_3$ alkyl-$R_{11})_2$, phenyl substituted by one or two groups selected from $NH_2$, —$N(C_1-C_3$ alkyl), —$N(C_1-C_3$ alkyl$)_2$, CN or —$(C_1-C_3$ alkyl)-tetrazole, or $C_1-C_6$ alkyl,

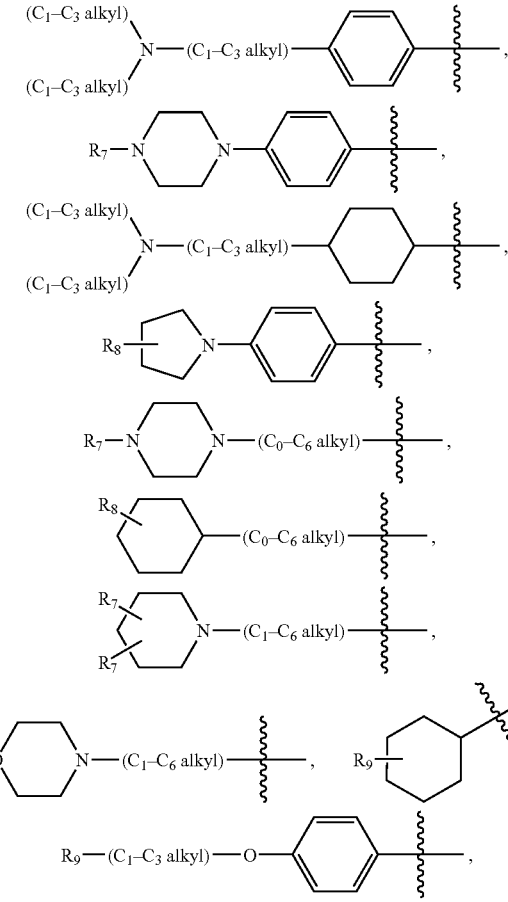

-continued

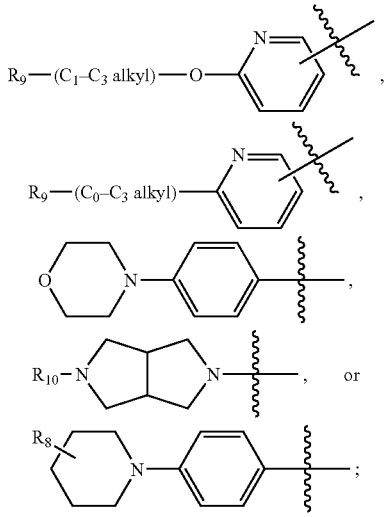

with each of the alkyl chains of any group in this $R_4$ definition being optionally substituted by from 1 to 4 OH groups;

$R_7$ in each instance is independently selected from H, —$NH_2$, $NH(C_1-C_3$ alkyl), $N(C_1-C_3$ alkyl)$_2$, or $C_1-C_3$ alkyl;

$R_8$ is H, OH or $C_1-C_3$ alkyl;

9 H, OH, —$NH_2$, $NH(C_1-C_3$ alkyl), or $N(C_1-C_3$ alkyl)$_2$;

$R_{10}$ is H or $C_1-C_3$ alkyl;

$R_{11}$ is H, CN, OH, $NH_2$, F, or $CF_3$;

or a pharmaceutically acceptable salt or ester form thereof.

Another group of compounds of this invention comprises those of the formulae:

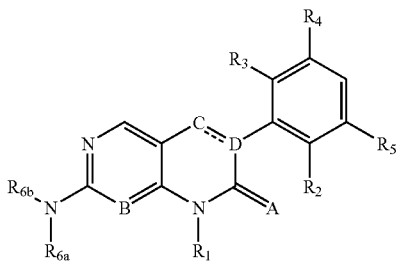

wherein:

A is O, $NH_2$, $NH(C_1-C_6$ alkyl), $N(C_1-C_6$ alkyl)$_2$, or —NHC(O)—$NHR_{12}$;

$R_{12}$ is $C_1-C_6$ straight or branched chain alkyl, preferably $C_1-C_4$ straight or branched chain alkyl, or —$(CH_2)_n$—$C_3-C_8$ cycloalkyl ring, preferably —$(CH_2)_n$—$C_3-C_7$ cycloalkyl, wherein n is an integer of from 1 to 3;

B, C, and D are independently selected from CH or N, with the proviso that C and D are not both N;

$R_1$ is selected from the group of $C_1-C_6$ straight or branched chain alkyl, preferably $C_1-C_4$ straight or branched chain alkyl, optionally substituted by —COOH, or a phenyl, benzyl, or $C_3-C_8$ cycloalkyl ring, preferably $C_3-C_7$ cycloalkyl, or —$CH_2$—$C_3-C_8$ cycloalkyl ring, preferably —$CH_2$—$C_3-C_7$ cycloalkyl, with the phenyl, benzyl or cycloalkyl rings being optionally substituted by 1 or 2 COOH or —$CH_2$—COOH groups; or $R_2$ is H, Cl or F;

$R_3$ is H, Cl or F, with the proviso that at least one of $R_2$ or $R_3$ is F;

$R_4$ is H, OH, —$OCH_3$, or —$OCH_2CH_3$, with the proviso that, if $R_4$ is H, $R_2$ and $R_3$ are not H;

$R_5$ is —$OCH_3$, or —$OCH_2CH_3$;

$R_{6a}$ is selected from H or $C_1-C_6$ alkyl, preferably $C_1-C_3$ alkyl;

$R_{6b}$ is selected from the group of —$(C_1-C_5$ alkyl)-$NH_2$, —$(C_1-C_5$ alkyl)-NH—$(C_1-C_3$ alkyl)-$R_{11}$, —$(C_1-C_5$ alkyl)-N—$(C_1-C_3$ alkyl-$R_{11})_2$, —O—$(C_1-C_5$ alkyl)-$NH_2$, —O—$(C_1-C_5$ alkyl)-NH—$(C_1-C_3$ alkyl)-$R_{11}$, —O—$(C_1-C_5$ alkyl)-N—$(C_1-C_3$ alkyl-$R_{11})_2$, —$(C_1-C_3$ alkyl)-$(CH_2OH)_2$, —$(C_1-C_3$ alkyl)-O—$(C_1-C_3$ alkyl)-$R_{11}$, —$(C_1-C_3$ alkyl)-O—$(C_1-C_3$ alkyl)-$NH_2$, —$(C_1-C_3$ alkyl)-O—$(C_1-C_3$ alkyl)-NH—$(C_1-C_3$ alkyl)-$R_{11}$, —$(C_1-C_3$ alkyl)-O—$(C_1-C_3$ alkyl)-N$(C_1-C_3$ alkyl-$R_{11})_2$, phenyl substituted by 1 or 2 groups selected from $NH_2$, —N$(C_1-C_3$ alkyl), —N$(C_1-C_3$ alkyl)$_2$, CN or —$(C_1-C_3$ alkyl)-tetrazole, or $C_1-C_6$ alkyl,

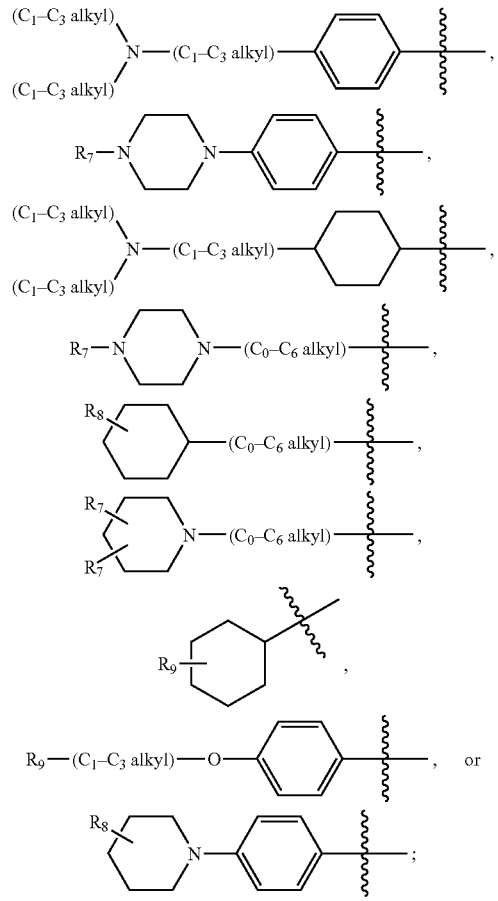

with each of the alkyl chains of any group in this $R_4$ definition being optionally substituted by from 1 to 4 OH groups;

$R_7$ in each instance is independently selected from H, —$NH_2$, $NH(C_1-C_3$ alkyl), $N(C_1-C_3$ alkyl)$_2$, or $C_1-C_3$ alkyl;

$R_8$ is H, OH or $C_1-C_3$ alkyl;

$R_9$ is H, OH, —$NH_2$, $NH(C_1-C_3$ alkyl), or $N(C_1-C_3$ alkyl)$_2$;

$R_{10}$ is H or $C_1$–$C_3$ alkyl;

$R_{11}$ is H, CN, OH, $NH_2$, F, or $CF_3$;

or a pharmaceutically acceptable salt or ester form thereof.

It will also be understood that the definition of $C_3$–$C_8$ cycloalkyl ring includes fully saturated rings, such as cyclopropyl, cyclobutyl, cyclopentyl, cyclohexyl, cycloheptyl and cyclooctyl groups, partially saturated carbocyclic rings having from 3 to 8 ring carbon atoms, such as cyclohexene, and bridged cycloalkyl groups, such as bicyclo[2.2.1]heptane.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of Formula I are capable of further forming both pharmaceutically acceptable formulations comprising salts, including but not limited to acid addition and/or base salts, solvates and N-oxides. This invention also provides pharmaceutical formulations comprising a compound of Formula I together with a pharmaceutically acceptable carrier, diluent, or excipient therefor. All of these forms are within the present invention.

Pharmaceutically acceptable acid addition salts of the compounds of Formula I include salts derived form inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge, et al., "Pharmaceutical Salts," *J. of Pharmaceutical Science*, 1977; 66:1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge, supra, 1977.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

Esters of the compounds of this invention may include those known in the art as acceptable for pharmaceutical uses. Non-limiting examples of pharmaceutically useful esters include branched or straight chain alkyl esters, particularly including alkyl, alkenyl or alkynyl groups of from 1 to 20 carbon atoms, preferably from 1 to 10 carbon atoms, including such esters as methyl, ethyl, propyl, isopropyl, butyl, t-butyl, pentyl, hexyl, lauryl, cetyl, myristyl, stearyl, pentenyl, hexynyl, vinyl, allyl, undecenyl, oleyl, linolenyl, etc.; alkoxyalkyl esters, preferably of from 1 to 10 carbon atoms, such as methoxymethyl ester; cycloalkyl or cycloalkenyl esters of from 1 to 8 carbon atoms, such as cyclopropyl, cyclohexyl, cyclohexenyl, cyclooctyl, or bicyclo[2.2.1]heptyl esters; alkylcycloalkyl esters, wherein a cycloalkyl group of from 3 to 8 carbon atoms is bridged to an acid moiety by an alkyl chain of from 1 to 6 carbon atoms, such as methylcyclopropyl or methylcyclohexyl esters; alkoxycycloalkyl esters wherein a cycloalkyl group of from 3 to 8 carbon atoms is bridged to an acid moiety by an alkoxy chain of from 1 to 6 carbon atoms, such as methoxycyclopropyl or methoxycycloheptyl esters; aryl or heteroaryl esters, such as phenyl, toluyl, xylyl, naphthyl, indolyl, pyridinyl or pyrimidinyl esters; arylalkyl esters, such as benzyl ester; heteroarylalkyl esters, such as pyridinylmethyl ester or indolylmethyl esters; arylalkoxy esters or heteroalkoxy esters, such as benzyloxy or pyridinylmethoxy esters.

It will be understood that the alkyl, alkenyl and alkynyl groups in the ester moieties herein, whether appearing alone or as a bridging group to, or substituent on, a ring moiety (cycloalkyl, aryl, heteroaryl, etc.) may be optionally substituted by groups including hydroxy, amino, nitro, perfluorinated alkyl (such as trifluoromethyl or pentafluoroethyl groups), cyano, or halo groups. Ring moieties in the esters, whether alone or bridged to the acidic moiety, are also optionally substituted by from 1 to 6 substituents selected from the group of alkyl of from 1 to 6 carbon atoms, hydroxy, amino, nitro, perfluorinated alkyl (such as trifluoromethyl or pentafluoroethyl groups), cyano, or halo groups.

This invention also provides substituted phenyl compounds that may be used to prepare compounds of this invention. They comprise those of the formula:

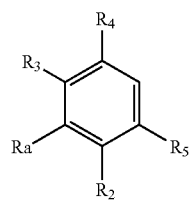

wherein:

$R_2$ is Cl or F;

$R_3$ is Cl or F, with the proviso that at least one of $R_2$ or $R_3$ is F;

$R_4$ is H, OH, —$OCH_3$, or —$OCH_2CH_3$;

$R_5$ is —$OCH_3$, or —$OCH_2CH_3$; and

Ra is selected from the group of NH$_2$, I, CN, —CH$_2$CN, —C(O)CN, —CH$_2$OH, —C(O)H, —C(O)OR, —CH$_2$C(O)OR, —C(O)C(O)OR; and R is selected from H or C$_1$–C$_6$ alkyl.

A group of phenyl compounds of this invention are those wherein R$_2$ and R$_3$ are F, and R$_4$ and R$_5$ are as defined above. Further phenyl compounds are those wherein R$_2$ and R$_3$ are F, R$_4$ is —OCH$_3$, and R$_5$ is —OCH$_3$ or —OCH$_2$CH$_3$.

Another group of novel substituted phenyl compounds useful in the preparation of pharmaceutically useful compounds are those of the formulae:

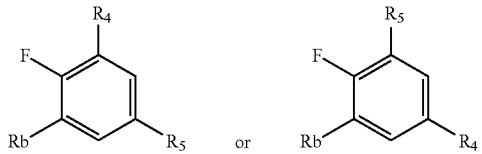

R$_4$ is H, OH, —OCH$_3$, or —OCH$_2$CH$_3$; R$_5$ is —OCH$_3$, or —OCH$_2$CH$_3$;

Rb is selected from NH$_2$, I, CN, —CH$_2$CN, —C(O)CN, —CH$_2$OH, —C(O)H, —C(O)OR, —CH$_2$C(O)OR, and —C(O)C(O)OR; with the proviso that when Rb is —C(O)H, R$_4$ and R$_5$ are not both —OCH$_3$; and R is selected from H or C$_1$–C$_6$ alkyl.

Each of these substituted phenyl compounds may be prepared by methods known in the art, as well as those described herein. It will be understood that —C(O)OR and —C(O)C(O)OR in each instance represents a carboxylic acid and an acetic acid moiety, respectively, or the alkyl esters thereof. It will also be understood that the compounds of the present invention may be prepared utilizing 2-Fluoro-3,5-dimethoxy-benzaldehyde (CAS Registry No. 113984-71-7).

Examples of useful phenylamine intermediates of this invention include 2,6-difluoro-3,5-dimethoxy-phenylamine; 2,6-difluoro-3,5-diethoxy-phenylamine; 3-ethoxy-2,6-difluoro-5-methoxy-phenylamine; 2-fluoro-3,5-dimethoxy-phenylamine; 2-fluoro-3,5-diethoxy-phenylamine; 3-ethoxy-2-fluoro-5-methoxy-phenylamine; 5-ethoxy-2-fluoro-3-methoxy-phenylamine; 5-methoxy-2,6-difluoro-3-hydroxy-phenylamine; 2-fluoro-3-hydroxy-5-methoxy-phenylamine; 2-fluoro-3-methoxy-5-hydroxy-phenylamine; 2-fluoro-3-hydroxy-5-ethoxy-phenylamine; 2-fluoro-3-ethoxy-5-hydroxy-phenylamine; 2,6-difluoro-3-methoxy-phenylamine, 2,6-difluoro-3-ethoxy-phenylamine, 2,6-difluoro-3-ethoxy-phenylamine, 2-chloro-6-fluoro-3,5-dimethoxy-phenylamine, 2-chloro-5-ethoxy-6-fluoro-3-methoxy-phenylamine, 2-chloro-3-ethoxy-6-fluoro-5-methoxy-phenylamine, 2-chloro-3-ethoxy-6-fluoro-5-hydroxy-phenylamine, 2-chloro-3-methoxy-6-fluoro-5-hydroxy-phenylamine, 2-fluoro-3-methoxy-6-chloro-5-hydroxy-phenylamine, 2-chloro-6-fluoro-3-methoxy-phenylamine or 6-chloro-3-ethoxy-2-fluoro-phenylamine.

Examples of useful phenyl intermediates of this invention, defined above, wherein Ra or Rb is CN include 2,6-difluoro-3,5-dimethoxy-benzonitrile; 2,6-difluoro-3,5-diethoxy-benzonitrile; 3-ethoxy-2,6-difluoro-5-methoxy-benzonitrile; 2-fluoro-3,5-dimethoxy-benzonitrile; 2-fluoro-3,5-diethoxy-benzonitrile; 3-ethoxy-2-fluoro-5-methoxy-benzonitrile; 5-ethoxy-2-fluoro-3-methoxy-benzonitrile; 5-methoxy-2,6-difluoro-3-hydroxy-benzonitrile; 2-fluoro-3-hydroxy-5-methoxy-benzonitrile; 2-fluoro-3-methoxy-5-hydroxy-benzonitrile; 2-fluoro-3-hydroxy-5-ethoxy-benzonitrile; 2-fluoro-3-ethoxy-5-hydroxy-benzonitrile; 2,6-difluoro-3-methoxy-benzonitrile, 2,6-difluoro-3-ethoxy-benzonitrile, 2,6-difluoro-3-ethoxy-benzonitrile, 2-chloro-6-fluoro-3,5-dimethoxy-benzonitrile, 2-chloro-5-ethoxy-6-fluoro-3-methoxy-benzonitrile, 2-chloro-3-ethoxy-6-fluoro-5-methoxy-benzonitrile, 2-chloro-3-ethoxy-6-fluoro-5-hydroxy-benzonitrile, 2-chloro-3-methoxy-6-fluoro-5-hydroxy-benzonitrile, 2-fluoro-3-methoxy-6-chloro-5-hydroxy-benzonitrile, 2-chloro-6-fluoro-3-methoxy-benzonitrile or 6-chloro-3-ethoxy-2-fluoro-benzonitrile.

Examples of useful phenyl intermediates of this invention, as defined above, wherein Ra or Rb is —CH$_2$—OH include (2,6-difluoro-3,5-dimethoxy-phenyl)-methanol; (2,6-difluoro-3,5-diethoxy-phenyl)-methanol; (3-ethoxy-2,6-difluoro-5-methoxy-phenyl)-methanol; (2-fluoro-3,5-dimethoxy-phenyl)-methanol; (2-fluoro-3,5-diethoxy-phenyl)-methanol; (3-ethoxy-2-fluoro-5-methoxy-phenyl)-methanol; (5-ethoxy-2-fluoro-3-methoxy-phenyl)-methanol; (5-methoxy-2,6-difluoro-3-hydroxy-phenyl)-methanol; (2-fluoro-3-hydroxy-5-methoxy-phenyl)-methanol; (2-fluoro-3-methoxy-5-hydroxy-phenyl)-methanol; (2-fluoro-3-hydroxy-5-ethoxy-phenyl)-methanol; (2-fluoro-3-ethoxy-5-hydroxy-phenyl)-methanol; (2,6-difluoro-3-methoxy-phenyl)-methanol, 2,6-difluoro-3-ethoxy-phenyl)-methanol, (2,6-difluoro-3-ethoxy-phenyl)-methanol, (2-chloro-6-fluoro-3,5-dimethoxy-phenyl)-methanol, (2-chloro-5-ethoxy-6-fluoro-3-methoxy-phenyl)-methanol, (2-chloro-3-ethoxy-6-fluoro-5-methoxy-phenyl)-methanol, (2-chloro-3-ethoxy-6-fluoro-5-hydroxy-phenyl)-methanol, (2-chloro-3-methoxy-6-fluoro-5-hydroxy-phenyl)-methanol, (2-fluoro-3-methoxy-6-chloro-5-hydroxy-phenyl)-methanol, (2-chloro-6-fluoro-3-methoxy-phenyl)-methanol or (6-chloro-3-ethoxy-2-fluoro-phenyl)-methanol.

Examples of useful phenyl carboxylic acid intermediates of this invention, defined above, wherein Ra or Rb is C(O)OR include 2,6-difluoro-3,5-dimethoxy-benzoic acid; 2,6-difluoro-3,5-diethoxy-benzoic acid; 3-ethoxy-2,6-difluoro-5-methoxy-benzoic acid; 2-fluoro-3,5-dimethoxy-benzoic acid; 2-fluoro-3,5-diethoxy-benzoic acid; 3-ethoxy-2-fluoro-5-methoxy-benzoic acid; 5-ethoxy-2-fluoro-3-methoxy-benzoic acid; 5-methoxy-2,6-difluoro-3-hydroxy-benzoic acid; 2-fluoro-3-hydroxy-5-methoxy-benzoic acid; 2-fluoro-3-methoxy-5-hydroxy-benzoic acid; 2-fluoro-3-hydroxy-5-ethoxy-benzoic acid; 2-fluoro-3-ethoxy-5-hydroxy-benzoic acid; 2,6-difluoro-3-methoxy-benzoic acid, 2,6-difluoro-3-ethoxy-benzoic acid, 2,6-difluoro-3-ethoxy-benzoic acid, 2-chloro-6-fluoro-3,5-dimethoxy-benzoic acid, 2-chloro-5-ethoxy-6-fluoro-3-methoxy-benzoic acid, 2-chloro-3-ethoxy-6-fluoro-5-methoxy-benzoic acid, 2-chloro-3-ethoxy-6-fluoro-5-hydroxy-benzoic acid, 2-chloro-3-methoxy-6-fluoro-5-hydroxy-benzoic acid, 2-fluoro-3-methoxy-6-chloro-5-hydroxy-benzoic acid, 2-chloro-6-fluoro-3-methoxy-benzoic acid or 6-chloro-3-ethoxy-2-fluoro-benzoic acid; or the C$_1$–C$_6$ alkyl esters thereof. Corresponding examples of useful phenyl intermediates of this invention, as defined above, wherein Ra or Rb is —CH$_2$—C(O)OR include (2,6-difluoro-3,5-dimethoxy-phenyl)-acetic acid; (2,6-difluoro-3,5-diethoxy-phenyl)-acetic acid; (3-ethoxy-2,6-difluoro-5-methoxy-phenyl)-acetic acid; (2-fluoro-3,5-dimethoxy-phenyl)-acetic acid; (2-fluoro-3,5-diethoxy-phenyl)-acetic acid; (3-ethoxy-2-fluoro-5-methoxy-phenyl)-acetic acid; (5-ethoxy-2-fluoro-3-methoxy-phenyl)-acetic acid; (5-methoxy-2,6-difluoro-3-hydroxy-phenyl)-acetic acid; (2-fluoro-3-hydroxy-5-methoxy-phenyl)-acetic acid; (2-fluoro-3-methoxy-5-hydroxy-phenyl)-acetic acid; (2-fluoro-3-hydroxy-5-ethoxy-phenyl)-acetic acid; (2-fluoro-3-ethoxy-5-hydroxyphenyl)-acetic acid; (2,6-difluoro-3-methoxy-phenyl)-acetic acid, 2,6-difluoro-3-ethoxy-phenyl)-acetic acid, (2,6-difluoro-3-ethoxy-phenyl)-acetic acid, (2-chloro-6-fluoro-3,5-dimethoxy-phenyl)-acetic acid, (2-chloro-5-ethoxy-6-fluoro-3-methoxy-phenyl)-acetic acid, (2-chloro-3-ethoxy-6-fluoro-5-methoxy-phenyl)-acetic acid, (2-chloro-3-ethoxy-6-fluoro-5-hydroxy-phenyl)-acetic acid, (2-chloro-3-methoxy-6-fluoro-5-hydroxy-phenyl)-acetic acid, (2-fluoro-3-methoxy-6-chloro-5-hydroxy-phenyl)-acetic acid, (2-chloro-6-fluoro-3-methoxy-phenyl)-acetic acid or (6-chloro-3-ethoxy-2-fluoro-phenyl)-acetic acid; or the $C_1$–$C_6$ alkyl esters thereof.

Examples of useful phenyl intermediates of this invention, as defined above, wherein Ra or Rb is —$CH_2$—C(O)C(O)OR include (2,6-difluoro-3,5-dimethoxy-phenyl)-oxo-acetic acid; (2,6-difluoro-3,5-diethoxy-phenyl)-oxo-acetic acid; (3-ethoxy-2,6-difluoro-5-methoxy-phenyl)-oxo-acetic acid; (2-fluoro-3,5-dimethoxy-phenyl)-oxo-acetic acid; (2-fluoro-3,5-diethoxy-phenyl)-oxo-acetic acid; (3-ethoxy-2-fluoro-5-methoxy-phenyl)-oxo-acetic acid; (5-ethoxy-2-fluoro-3-methoxy-phenyl)-oxo-acetic acid; (5-methoxy-2,6-difluoro-3-hydroxy-phenyl)-oxo-acetic acid; (2-fluoro-3-hydroxy-5-methoxy-phenyl)-oxo-acetic acid; (2-fluoro-3-methoxy-5-hydroxy-phenyl)-oxo-acetic acid; (2-fluoro-3-hydroxy-5-ethoxy-phenyl)-oxo-acetic acid; (2-fluoro-3-ethoxy-5-hydroxy-phenyl)-oxo-acetic acid; (2,6-difluoro-3-methoxy-phenyl)-oxo-acetic acid, 2,6-difluoro-3-ethoxy-phenyl)-oxo-acetic acid, (2,6-difluoro-3-ethoxy-phenyl)-oxo-acetic acid, (2-chloro-6-fluoro-3,5-dimethoxy-phenyl)-oxo-acetic acid, (2-chloro-5-ethoxy-6-fluoro-3-methoxy-phenyl)-oxo-acetic acid, (2-chloro-3-ethoxy-6-fluoro-5-methoxy-phenyl)-oxo-acetic acid, (2-chloro-3-ethoxy-6-fluoro-5-hydroxy-phenyl)-oxo-acetic acid, (2-chloro-3-methoxy-6-fluoro-5-hydroxy-phenyl)-oxo-acetic acid, (2-fluoro-3-methoxy-6-chloro-5-hydroxy-phenyl)-oxo-acetic acid, (2-chloro-6-fluoro-3-methoxy-phenyl)-oxo-acetic acid or (6-chloro-3-ethoxy-2-fluoro-phenyl)-oxo-acetic acid; or the $C_1$–$C_6$ alkyl esters thereof.

3-Phenyl-pyrimido[4,5-d]pyrimidin-2-one compounds of this invention may be prepared by methods known in the art, including those described in WO 99/61444 (Dobrusin et al.), and WO 01/29042 (Dunn et al.). An example of useful synthetic routes includes that seen in Scheme 1. Treatment of 4-Chloro-2-methylsulfanyl-pyrimidine-5-carboxylic acid ethyl ester (1) with an $R_1$-substituted amine, wherein $R_1$ is as defined herein, including alkylamines and aryl amines, forms the corresponding 4-$R_1$-amino-2-methylsulfanyl-pyrimidine-5-carboxylic acid ethyl ester (2a–2h). This treatment may be carried out in an art recognized solvent, such as tetrahydrofuran, or dichloromethane. Reduction of the ester (2a–2h) to the corresponding alcohol (3a–3h) can be carried out in art recognized methods, such as using lithium aluminum hydride in tetrahydrofuran.

Scheme 1

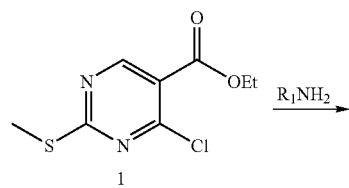

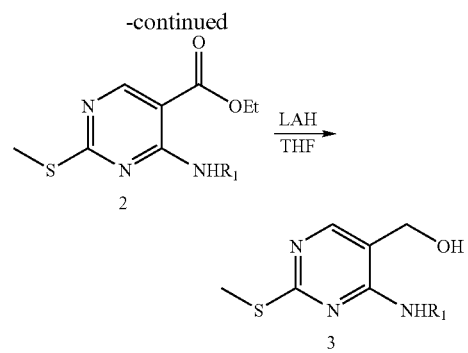

Subsequent oxidation of the alcohol (3) yields the corresponding aldehyde (4), which may be treated with an aryl amine, ArNH$_2$, wherein Ar is as defined for its optionally substituted groups at the desired position, to provide the corresponding 2-methylsulfanyl-4-$R_1$-amino-5-arylimino-pyrimidine (8c).

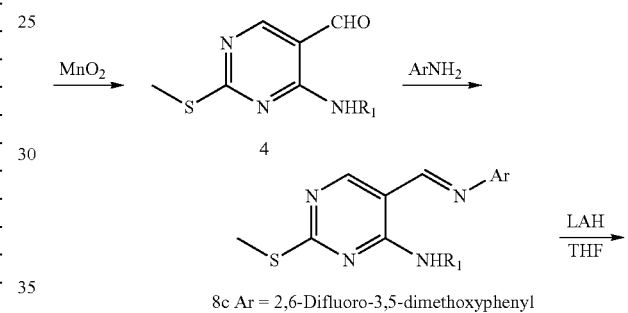

8c Ar = 2,6-Difluoro-3,5-dimethoxyphenyl

The 5-arylamino compound (8c) may then be reduced to the corresponding 5-aryl-amine (13c) using conventional reducing agents, such as sodium borohydride, lithium aluminum hydride or sodium triacetoxyborohydride under art recognized conditions. Cyclization of the amine (13c) to provide the 1-$R_1$-7-methylsulfanyl-3-aryl-1H-pyrimido[4,5-d]pyrimidin-2-one (18c) may be accomplished using sodium hydride and carbonyldiimidazole (CDI). Oxaziridine-mediated oxidation of the 7-position sulfanyl compounds (18c) provides the corresponding sulfinyl compounds (23c), which may then be reacted with an $R_6$-substituted amine, wherein the $R_6$ positional groups are as defined herein, to provide the desired 7-$R_6$-amino-3-Phenyl-pyrimidin-2-one compounds.

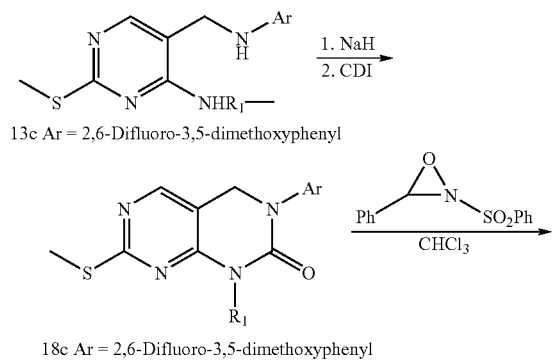

13c Ar = 2,6-Difluoro-3,5-dimethoxyphenyl

18c Ar = 2,6-Difluoro-3,5-dimethoxyphenyl

-continued

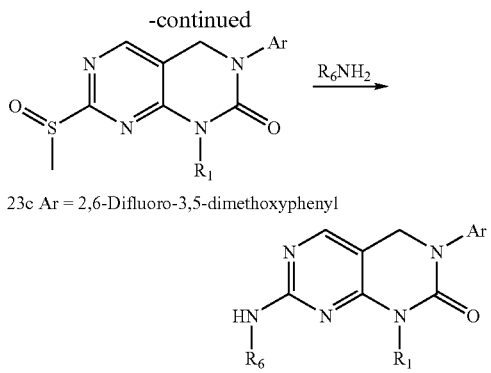

23c Ar = 2,6-Difluoro-3,5-dimethoxyphenyl

As depicted in Scheme 1, above, this application also comprises compounds useful in preparation of the pharmaceutically useful compounds described herein, the compounds having the formulae:

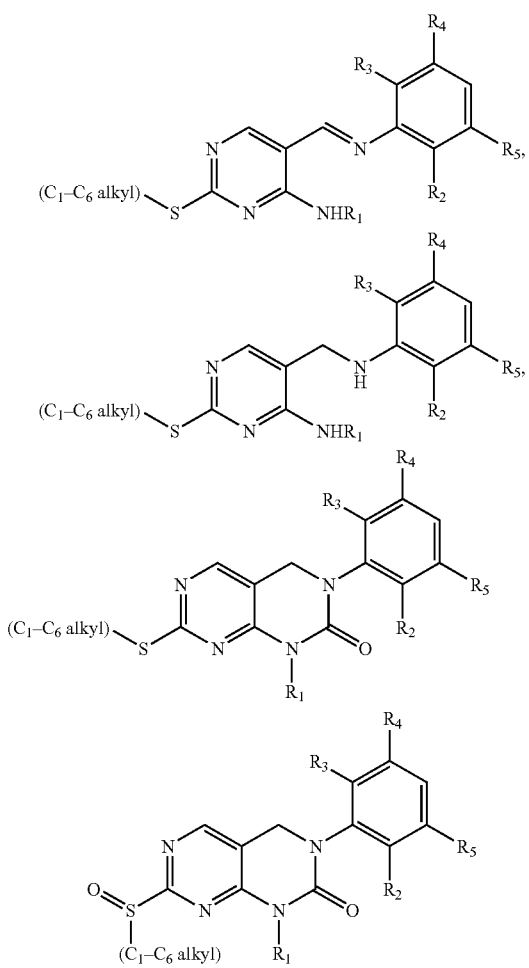

wherein $R_1$, $R_2$, $R_3$, $R_4$, and $R_5$ may be as defined in each instance herein.

Preparation of naphthiridone compounds of this invention can also be accomplished by methods known in the art, such as those described in WO 99/09030 (Barvian et al.). As seen in Scheme 2, 4,6-Diamino-3-pyridylcarboxaldehyde (1) can be reacted with an appropriate aryl acetonitrile (ArCOCN) to provide the corresponding 3-aryl-[1,6]napthyridine-2,7-diamine (2), also described in U.S. Pat. No. 5,620,981, after the manner reported by Hawes et al., J. Heterocycl. Chem., 1972:9,703. The 3-aryl-[1,6]napthyridine-2,7-diamine (2) may be converted to 3-aryl-7-fluoro-[1,6]napthyridine-2-one (3) by a diazotization reaction in 50% aqueous fluoroboric acid in a large excess (up to 8 equivalents) of solid sodium nitrite at low temperature (at or below −5° C.) for several days, after the manner previously described by Rewcastle et al., J. Med. Chem., 1996;39,1823. The corresponding $R_1$-substituted compounds (4) of this invention, wherein $R_1$ is as defined herein, may be produced by treatment of the 3-aryl-7-fluoro-[1,6]napthyridine-2-one (3) with an appropriate $R_1$-iodide, such as an appropriate alkyl iodide, in the presence of a base in a suitable dry, unreactive solvent, such as dimethylformamide, at from about 0° C. to about 20° C. A small amount of the corresponding 2-position —$OR_1$ compound may result from competing O-alkylation and can be removed by convention chromatography techniques. The resulting 7-Fluoro-1-R1-3-aryl-1H[1,6]naphthyridin-2-one compounds (4) may be treated with an appropriate aromatic or aliphatic amine ($R_6NH_2$) to yield the desired naphthiridone compounds of this invention. In the reaction Schemes 1–6, it will be understood that the listings of $R_6NH_2$ reactants and —$NHR_6$ substituents refers equally to all of the options of $NHR_{6a}R_{6b}$ reactants and —$NR_{6a}R_{6b}$ substituents described herein.

Scheme 2

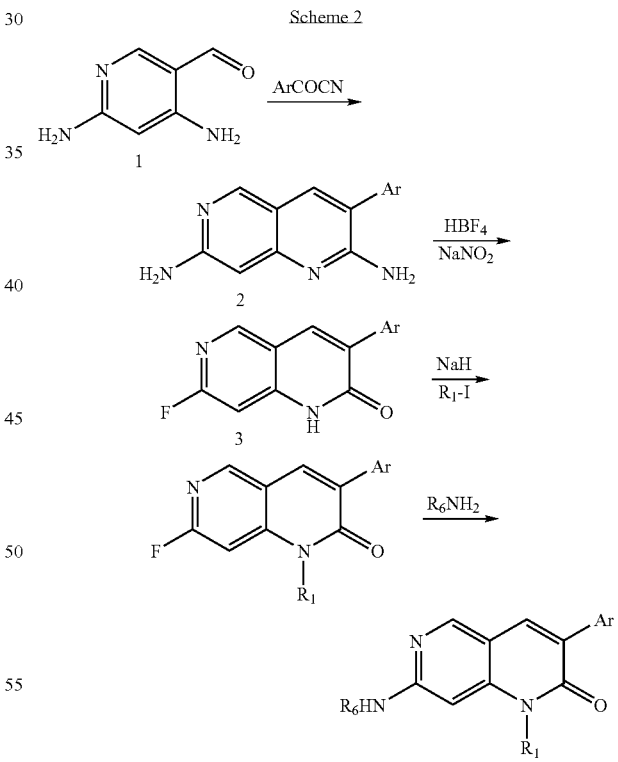

Pteridinone compounds of this invention may be prepared by methods known in the art, including those described in WO 01/19825 (Denny et al.). An example of these methods is the reaction of 2,4-Dichloro-5-nitro-pyrimidine (1) with an appropriate $R_1$-amine, preferably at reduced temperatures, to form 2-Chloro-5-nitro-pyrimidin-4-yl)-$R_1$-amine (2), wherein $R_1$ is as defined for the corresponding positional groups herein. Additional treatment with $R_6$-primary amine, preferably at ambient temperatures, provides the corresponding 5-nitro-2,4-diaminopyrimidine compound (3), wherein $R_6$ is as defined for the corresponding positional groups herein. The nitro compound (3) can then be reduced by conventional methods to the corresponding 2,4,5-triaminopyrimidine (4) through conventional means, such as catalytic hydrogenation. Treatment of the amine (4) with an appropriately substituted oxophenylacetic acid ester, preferably at elevated temperatures of from about 50° C. to about 150° C., produces the desired cyclized 2-substituted amino-6-phenyl-8H-pteridin-7-one (5).

This invention also comprises the synthetically useful compounds of the formulae:

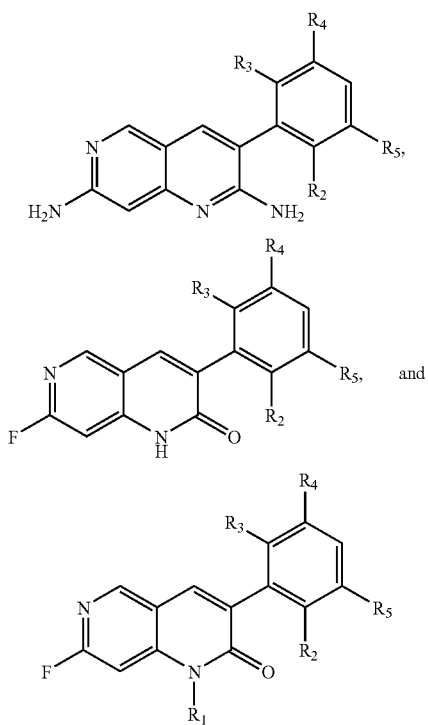

wherein $R_1$, $R_2$, $R_3$, $R_4$, and $R_5$ may be as defined in each instance herein.

Scheme 3

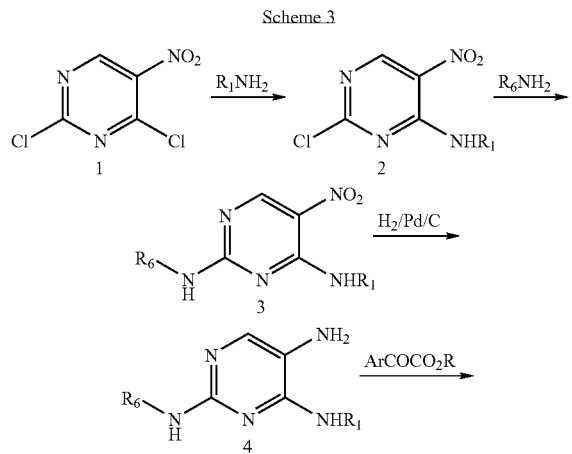

-continued

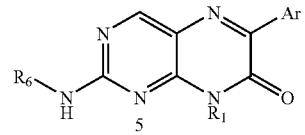

Synthetic routes to prepare pteridinone ureas (5), as defined herein, include the techniques described in WO 01/19825 (Denny et al.). As seen in Scheme 4, 2,4-Dichloro-5-nitro-pyrimidine (1) may be treated with ammonia to provide the corresponding 2-Chloro-5-nitro-pyrimidin-4yl-amine (2). Reduction of the nitro group, for instance by reaction with hydrogen in the presence of a catalyst such as palladium on carbon, and treatment with an $R_6$-substituted amine yields the N—$R_6$-pyrimidine-2,4,5-triamine (3). Cyclization to pteridine (4) is accomplished by reaction of the triamine (3) with an agent such as an aryl ketonitrile (ArCOCN). Subsequent treatment of the pteridine (4) with an appropriate isocyanate, wherein $R_7$ is as defined herein, in the presence of NaH provides the desired urea (5).

This invention further comprises compounds of the formulae:

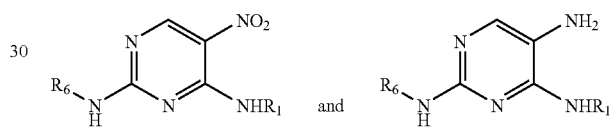

wherein $R_1$ and $R_6$ are as defined herein, which may be used in the synthesis of the pharmaceutically useful pteridinone compounds of this invention.

Scheme 4

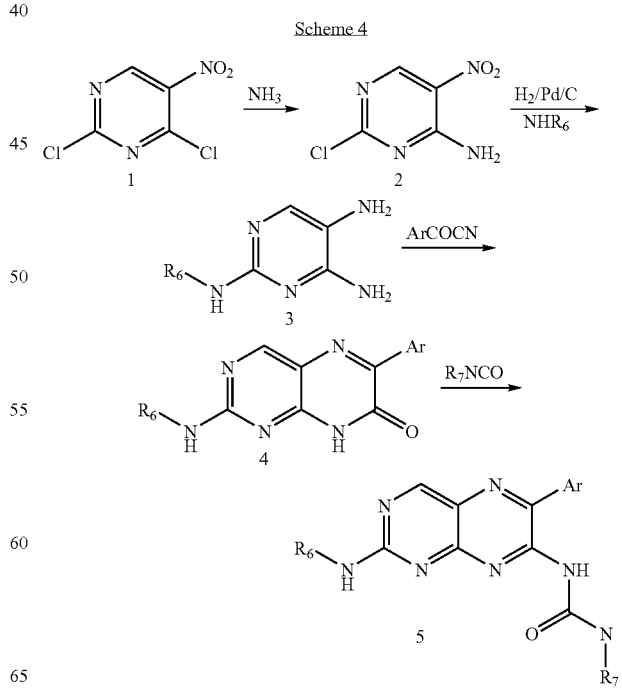

As depicted in Scheme 4, above, this invention additionally comprises triaminopyrimidine compounds of the formula:

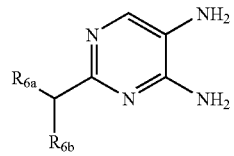

wherein $R_{6a}$ and $R_{6b}$ are as defined herein.

Pyridopyrimidine compounds of this invention can also be prepared by methods known in the art. Examples of references describing their synthesis include U.S. Pat. No. 5,733,913 (Blankley et al.), U.S. Pat. No. 5,733,914 (Blankley et al.), WO 02/12237 (Beylin et al.), and WO 9833798 (Boschelli et al.). Scheme 5, below, demonstrates a procedure for preparation of pyridopyrimidine compounds of this invention. As depicted, an appropriate 4-(substituted amino)-2-methylsulfanyl-pyrimidine-5-carboxaldehyde (1) (*J. Med. Chem.*, 1998;41(22):4365–4377 or *J. Med. Chem.*, 1998;41(17):3276–3292) can be treated with acetonitrile agent in the presence of a base and suitable solvent to afford the condensed 6-(aryl)-8-(substituted)-2-methylsulfanyl-8H-pyrido[2,3-d]pyrimidin-7-ylideneamine product (2). Product (2) can be acylated, followed by catalyzed hydrolysis, to the corresponding 7-keto compound (3). The methylthio group can then be oxidized to the respective sulfoxide (4), which is displaced to form the 4-aminopyridine or substituted 4-aminopyridine product (5). Additional reagents, conditions and solvents for these steps may be seen in WO 01/12238 (Hamby et al.).

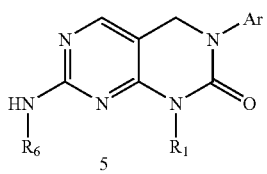

A further synthesis of pyridopyrimidone compounds of this invention can be accomplished by the alternate condensation route demonstrated in Scheme 6, In this method, the initial preparation of the 4-thioalkyl-7-keto compound (2) is accomplished by condensation of the 4-(substituted amino)-2-methylsulfanyl-pyrimidine-5-carboxaldehyde (1) with a substituted aryl acetic acid ester, such as a phenyl acetic acid alkyl ester, in the presence of a suitable base, such as 1,8-diazabicyclo[5.4.0]undec-7-ene. The reaction can be accomplished neat or in a solvent such as dimethylformamide or dimethyl sulfoxide.

This invention also comprises compounds of the formulae:

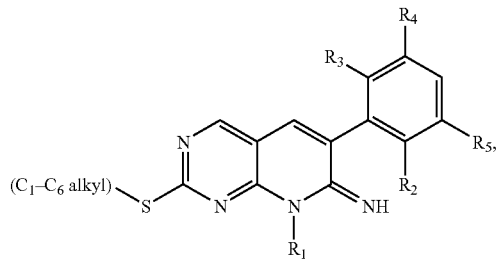

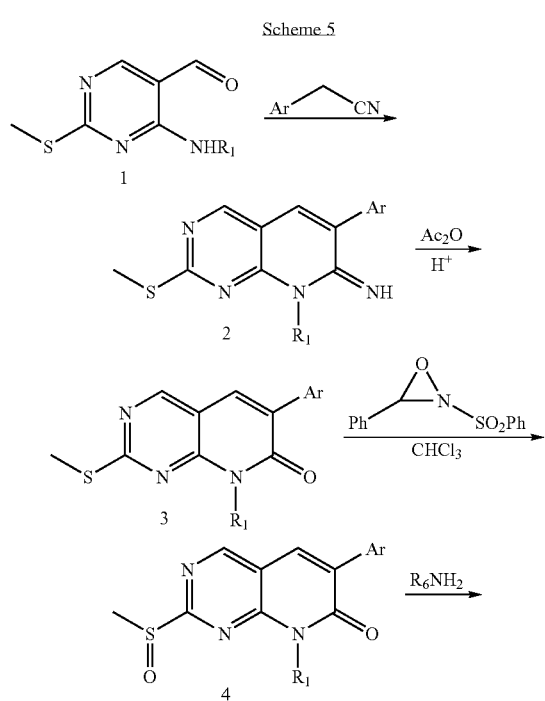

Scheme 5

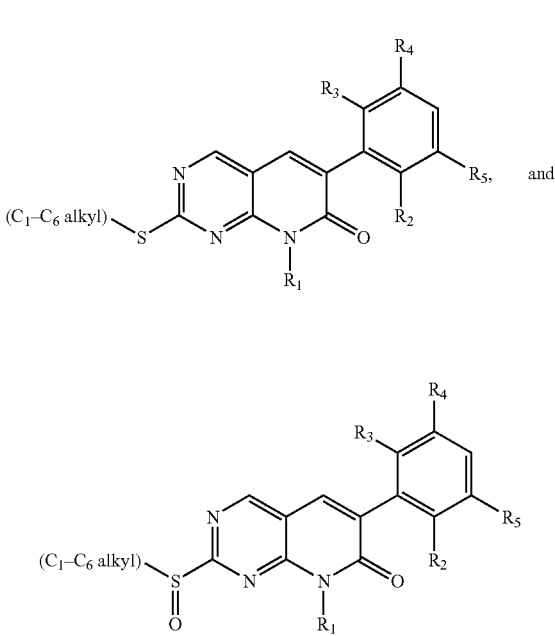

wherein the variables $R_1$, $R_2$, $R_3$, $R_4$, and $R_5$ may be as defined in each instance herein.

Scheme 6

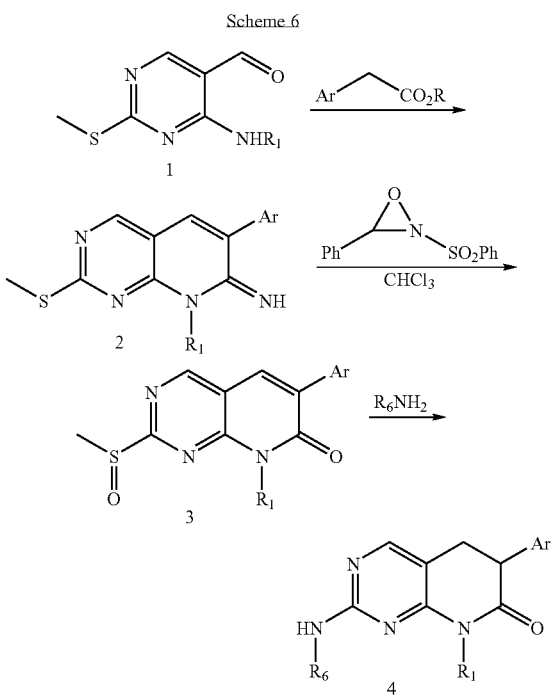

As noted in Scheme 6, this invention also comprises compounds of the formulae:

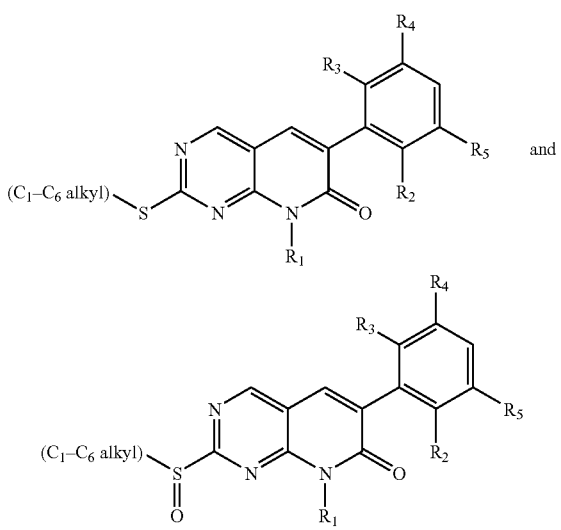

wherein the variables $R_1$, $R_2$, $R_3$, $R_4$, and $R_5$ may be as defined in each instance herein.

The following non-limiting descriptions also demonstrate methods for their synthesis.

1) Preparation of Anilines

Route A for preparation of 2,6-Difluoro-3,5-dimethoxyaniline 2,6-Difluoro-3,5-dimethoxyaniline can be prepared as follows:

Methyl 4-(benzylamino)-2,3,5,6-tetrafluorobenzoate

Methyl pentafluorobenzoate (41.4 g, 183 mmol) was treated with N-methylpyrrolidinone (36.0 g) and the solution stirred and cooled to 5° C. under a $N_2$ atmosphere. Benzylamine (19.8 g, 185 mmol) was added dropwise over 27 min. at 5° C.–20° C. The resulting thick yellow slurry was cooled to 2° C. over 25 min. and N,N-diisopropyl ethylamine (27.0 g, 209 mmol) was added over 30 min. at 3° C.–10° C. The mixture was allowed to warm to 18° C. and stirred for 2 hrs. It was then heated to 60° C. and stirred another 2 hs at 58° C.–67° C. The resulting solution was cooled to room temperature and stirred overnight. The mixture was treated with toluene (200 mL) and methyl tert-butyl ether (120 mL) and extracted with water (150 mL) followed by 10% aqueous acetic acid (2×50 mL). The organic layer was concentrated to a solid, which was recrystallized from toluene (45 mL) and heptane (50 mL). After cooling to −20° C., the crystals were collected, washed with heptane (2×25 mL) and vacuum dried at 35° C. to give methyl 4-(benzylamino)-2,3,5,6-tetrafluorobenzoate (49.3 g, 157 mmol): mp 96–97° C.

Methyl 4-(benzylamino)-3,5-difluoro-2,6-dimethoxybenzoate

Methyl 4-(benzylamino)-2,3,5,6-tetrafluorobenzoate (24.0 g, 76.6 mmol) was cooled to 5° C.–10° C. under a nitrogen atmosphere and a 25 weight % solution of sodium methoxide in methanol (53.5 mL, 234 mmol) was added dropwise over 5 minutes with continued cooling. The resulting mixture was stirred with ice bath cooling for another 10 minutes, the ice bath was removed and the mixture allowed to warm to 35° C.–40° C. It was recooled to room temperature and held for 4.5 hours before heating to 65° C.–70° C. where it was held for 3.5 hours. The mixture was cooled to room temperature and held overnight. Acetic acid (7.5 g) was added followed by methyl tert-butyl ether (250 mL) and water (100 mL). The lower aqueous layer was separated and the organic layer extracted with saturated, aqueous sodium bicarbonate solution (2×50 mL) followed by water (25 mL). The organic solution was concentrated under vacuum to give methyl 4-(benzylamino)-3,5-difluoro-2,6-dimethoxybenzoate as a yellow oil (24.5 g).

4-(Benzylamino)-3,5-difluoro-2,6-dimethoxybenzoic acid

Methyl 4-(benzylamino)-3,5-difluoro-2,6-dimethoxybenzoate (24.0 g) was dissolved in ethanol (75 mL) and the solution stirred and cooled to 10° C. under a nitrogen atmosphere. Sodium hydroxide, 50% aqueous solution (12.5 g, 156 mmol) was added dropwise over 10 minutes at 10° C.–15° C. followed by ethanol (10 mL). The solution was stirred at 15° C.–25° C. A thick precipitate formed. Stirring was continued for a total of 2 hours at 15° C.–25° C. The mixture was heated to 50° C.–55° C. where it was held for 1.5 hours. The mixture was allowed to cool to room temperature and held overnight. Water (100 mL) was added and the resulting solution cooled in an ice bath and acidified with 37% HCl (13.5 mL) to pH 2. The mixture was extracted with toluene (100 mL) and methyl tert-butyl ether (100 mL) and the organic extract washed with water (10 mL) and concentrated to an oil. This was triturated with toluene (20 mL) to give crystals which were collected and vacuum dried at 45° C. to give 4-(benzylamino)-3,5-difluoro-2,6-dimethoxybenzoic acid (19.4 g, 60 mmol): mp: 85° C.–86° C. (decomposition with gas evolution).

N-Benzyl-2,6-difluoro-3,5-dimethoxyaniline 4-(Benzylamino)-3,5-difluoro-2,6-dimethoxybenzoic acid (9.1 g, 28.1 mmol) was treated with chlorobenzene (45 mL) and the solution heated to reflux under nitrogen where it was maintained for 16 hours. The solution was cooled to room temperature and extracted with saturated, aqueous sodium bicarbonate solution (2×5 mL) followed by water. The organic layer was concentrated under reduced pressure to an oil that crystallized on standing. This was recrystallized from heptane (10 mL) and toluene (5 mL), the mixture cooled to −10° C., filtered and the crystals washed with heptane (10 mL) and vacuum dried at 35° C. to give N-benzyl-2,6-difluoro-3,5-dimethoxyaniline (7.4 g, 26.5 mmol). mp: 65° C.–66° C.

2,6-Difluoro-3,5-dimethoxyaniline

N-Benzyl-2,6-difluoro-3,5-dimethoxyaniline (6.0 g, 21.5 mmol) was dissolved in THF (40 mL) and the solution hydrogenated over 20% palladium hydroxide on carbon catalyst (0.6 g) at 20° C.–25° C. 48–50 psi hydrogen pressure for 16 hours. The mixture was filtered, the catalyst washed with THF (2×15 mL) and the combined filtrates concentrated to a solid. This was recrystallized from heptane (10 mL) and toluene (4.5 mL). The mixture was cooled to −10° C. before filtering. The crystals were washed with heptane (2×10 ML) and vacuum dried at 35° C. to give 2,6-difluoro-3,5-dimethoxyaniline as off-white needles (3.85 g, 20.4 mmol). mp: 78° C.–79° C.

Route B for the preparation of 2,6-Difluoro-3,5-dimethoxyaniline 2,6-Difluoro-3,5-dimethoxy benzoic acid methyl ester A solution of 336 g (1.71 mol) of methyl 3,5-dimethoxy benzoate in 0.84 L of acetonitrile was cooled down to 0° C. on an ice bath under nitrogen atmosphere. A suspension of 912 g (2.57 mol) of SelectFluor: 1-chloromethyl-4-fluoro-1,4-diazobicyclo[2.2.2] octane bis(tetrafluoroborate) in 16 L acetonitrile was added keeping the temperature close to 0° C. The reaction was stirred overnight warming up to room temperature. The next day, the reaction mixture was poured into 10 L of the sodium carbonate solution and extracted with 20 L of t-butylmethyl ether. The organic layer was washed with 3.75 L of brine, dried with sodium sulfate, filtered and evaporated. The crude mixture was separated by Biotage 150 column chromatography eluting with a gradient of heptane:EtOAc 30:1(36 L) to 25:1(36 L) to 20:1(54 L) to 15:1(54 L) to obtain 119.29 g (30% ) of the title compound. MS (APCI) (m+1)/z 233.1.

2,6-Difluoro-3,5-dimethoxy benzoic acid

A suspension of 115 g (0.49 mol) of 2,6-difluoro-3,5-dimethoxy benzoic acid methyl ester and 42.9 g (1.07 mol) of solid sodium hydroxide in 1.4 L of anhydrous ethanol was refluxed for 24 hours. The ethanol was concentrated in vacuo and the solid residue was dissolved in water and extracted two times with ethyl ether. The aqueous layer was acidified with concentrated hydrochloric acid and a white precipitate was filtered, washed with cold water and dried in vacuo to give 87.9 g (81%) of the title compound. MS (APCI) (m+1)/z 219.1.

(2,6-Difluoro-3,5-dimethoxy-phenyl)-carbamic acid tert-butyl ester

To a stirred mixture of 47.7 g (0.22 mol) of 2,6-difluoro-3,5-dimethoxy benzoic acid, 32 mL (0.22 mol) of triethylamine and 16.2 g (0.22 mol) of t-butanol in 500 mL of toluene, 48.2 mL (0.22 mol) of diphenylphosphoryl azide was added in one portion and the mixture was heated to 60° C.–70° C. After approximately 1 hour, the reaction was completed and the mixture was cooled down. The toluene was removed in vacuo. Then, ethyl acetate was added and the resulting solution was washed two times with saturated potassium hydrogen-phosphate solution, two times with saturated sodium bicarbonate solution, one time with brine, dried over sodium sulfate, filtered and evaporated. The crude product was purified by column chromatography: 1 kg of silica eluting with dichloromethane to give 45 g (71%) of the title compound.

2,6-Difluoro-3,5-dimethoxy-phenylamine

To 34.6 g (0.12 mol) of (2,6-difluoro-3,5-dimethoxy-phenyl)-carbamic acid tert-butyl ester, 120 mL of trifluoroacetic acid was added to give a homogeneous solution which was stirred at room temperature for 30 minutes. After 30 min., the reaction mixture was concentrated in vacuo. To the residue, a saturated solution of sodium bicarbonate was carefully added to pH 8. The resulting suspension was extracted twice with diethylether. Combined diethylether layers were washed once with brine, dried over sodium sulfate, filtered and evaporated to give 22 g (97%) of title compound. MS (APCI) (m+1)/z 190.1.

2-Fluoro-3,5-dimethoxy-benzoic acid methyl ester

A solution of 168 g (0.86 mol) of methyl 3,5-dimethoxy benzoate in 0.42 L of acetonitrile was cooled down to 0° C. on an ice bath under nitrogen atmosphere. A suspension of 456 g (1.3 mol) of SelectFluor: 1-chloromethyl-4-fluoro-1,4-diazobicyclo[2.2.2] octane bis(tetrafluoroborate) in 8 L acetonitrile was added keeping the temperature close to 0° C. The reaction was stirred overnight warming up to room temperature. The next day, the reaction mixture was poured into 5 L of the sodium carbonate solution and extracted with 20 L of t-butylmethyl ether. The organic layer was washed with 1.875 L of brine, dried with sodium sulfate, filtered and evaporated. The crude mixture was separated by Biotage column chromatography eluting with a gradient of heptane:EtOAc 30:1(18 L) to 25:1(18 L) to 20:1(27 L) to 15:1(27 L) to obtain 73.6 g (40% ) of the title compound. MS (APCI) (m+1)/z 215.1.

2-Fluoro-3,5-dimethoxy benzoic acid

A suspension of 66.7 g (0.27 mol) of 2-fluoro-3,5-dimethoxy-benzoic acid methyl ester and 27 g (0.675 mol) of solid sodium hydroxide in 815 mL of anhydrous ethanol was refluxed for 24 hours. The ethanol was concentrated in vacuo and the solid residue was dissolved in water and extracted two times with ethyl ether. The aqueous layer was acidified with concentrated hydrochloric acid and a white precipitate was filtered, washed with cold water and dried in vacuo to afford 53.9 g (86.5%) of the title compound. MS (APCI) (m+1)/z 201.0.

(2-Fluoro-3,5-dimethoxy-phenyl)-carbamic acid tert-butyl ester

To a stirred mixture of 54.5 g (0.27 mol) of 2-fluoro-3,5-dimethoxy benzoic acid, 38 mL (0.27 mol) of triethylamine and 20.1 g (0.27 mol) of t-butanol in 500 mL of toluene, 59.9 mL (0.27 mol) of diphenylphosphoryl azide was added in one portion and the mixture was heated to 60° C.–70° C. After approx. 1 hour, the reaction was completed and the mixture was cooled down. The toluene was removed in vacuo. Then, ethyl acetate was added and the resulting solution was washed two times with saturated potassium hydrogen-phosphate solution, two times with saturated sodium bicarbonate solution, one time with brine, dried over sodium sulfate, filtered and evaporated. The crude product was purified by column chromatography: 1.4 kg of silica eluting with dichloromethane to give 63.2 g (86%) of the title compound. MS (APCI) (m+1)/z 270.0.

2-Fluoro-3,5-dimethoxy-phenylamine

To 56.6 g (0.21 mol) of (2-fluoro-3,5-dimethoxy-phenyl)-carbamic acid tert-butyl ester, 184 mL of trifluoroacetic acid was added to give a homogeneous solution which was stirred at room temperature for 30 minutes. After 30 minutes, the reaction mixture was concentrated in vacuo. To the residue, a saturated solution of sodium bicarbonate was carefully added to pH 8. The resulting suspension was extracted two times with diethylether. The combined diethylether layers were washed one time with brine, dried over sodium sulfate, filtered and evaporated to give 34.1 g (95.5%) of title compound. MS (APCI) (m+1)/z 172.0.

1-Ethoxy-2,4-difluoro-benzene

Into a solution of 2,4-difluorophenol (69 g, 0.53 mol) and acetone (500 mL) was added 1.2 equivalents of potassium carbonate (89 g, 0.64 mol) followed by 1.3 equivalents of iodoethane (108 g, 0.69 mol). The reaction mixture is warmed to reflux for 4 hours then concentrated in vacuo. The residue was dissolved in ethyl acetate (500 mL), washed with a saturated aqueous solution of sodium chloride (3×200 mL), dried over $Na_2SO_4$, and concentrated in vacuo to give 75 g (905) of the title compound as yellow oil, which was used without further purification in the next step.

3-Ethoxy-2,6-difluoro-benzoic acid

A solution of 1-ethoxy-2,4-difluoro-benzene (16 g, 0.10 mol) in dry THF (170 mL) was cooled to −78° C. and lithium diisopropylamide (62 mL, 0.12 mol) was added dropwise. The reaction mixture was stirred at −78° C. for 1.5 hours and then $CO_2$ (from dry ice, dried through $H_2SO_4$) was introduced. After 1 hour, the reaction mixture was warmed to 0° C. and 6M HCl was added to adjust pH to 2–3. The solution was extracted with ethyl acetate (3×100 mL), extracted with 5% aq. NaOH (3×100 mL). The NaOH extracts are adjusted to pH 1 with HCl and the white solid separated is filtered, washed with water then dried in vacuum oven to give the title compound 3, as white solid. Yield: 16.2 g (80%), mp: 157° C.–158° C.

(3-Ethoxy-2,6-difluoro-phenyl)-carbamic acid tert-butyl ester

To a mixture of 3,6-difluoro-3-ethoxybenzoic acid (15.8 g, 78.2 mmol), triethyl amine (12.2 mL, 8.9 g, 86 mmol) and tert-butanol (8.3 mL, 6.4 g, 86 mmol) in toluene (250 mL) was added diphenylphosphorylazide (18 mL, 82.1 mmol). The reaction mixture was heated at 60° C.–70° C. for 2 hours. The reaction mixture was evaporated and the residue was dissolved in ethyl acetate (250 mL), washed with $KH_2PO_4$ (3×), aq. satd. $NaHCO_3$ (3×), brine (2×), dried over $Na_2SO_4$, filtered and evaporated under vacuum to give the title compound as white solid. The above solid was used directly in the next step without purification. Yield: 20.5 g, 96%

3-Ethoxy-2,6-difluoro-phenylamine

A solution of (3-ethoxy-2,6-difluoro-phenyl)-carbamic acid tert-butyl ester (135 g, 0.525 mol) in a mixture of dichloromethane and 10 equivalents trifluoroacetic acid (598 g, 5.25 mol) was stirred at room temperature for 1 hour and concentrated in vacuo. The pH of the residue was adjusted to pH 8 with a saturated aqueous solution of sodium bicarbonate. The organic layer was separated and the aqueous layer is extracted with ethyl acetate (3×250 mL). The organic extracts were combined, washed with a saturated aqueous solution of sodium chloride (2×), dried and concentrated in vacuo. Chromatography of the yellow residual liquid down silica gel using 25:1 hexane:ethyl acetate gave 65 g (66%) of the title compound as oil.

2) Preparation of Esters

Procedure A

General Procedure for the Parallel Synthesis of 4-Substituted-2-methylsulfanyl-pyrimidine-5-carboxylic acid ethyl esters (2)

Into an Argonaut Technologies' Quest 205 100 mL reactor was added 8.0 g (34.4 mmol) of 4-chloro-2-methylsulfanyl-pyrimidine-5-carboxylic acid ethyl ester in 70 mL of dry THF. To the reaction mixture was added 1.1 equivalents of triethylamine followed by a solution of 1.1 equivalents of amine ($R_1NH_2$) in 10 mL of dry THF. The reaction mixture was agitated overnight under a nitrogen atmosphere at room temperature. The THF solution was drained from the reaction vessel, and the residue was washed with THF. The THF solutions were combined, evaporated, and redissolved in 35 mL of ethyl acetate. The ethyl acetate solution was added back into the reaction vessel containing the residue, followed by 40 mL of 0.5 M NaOH. The reaction was agitated and the aqueous layer removed. The ethyl acetate solution was washed twice with 0.5 M NaOH and once with a saturated solution of sodium chloride. The ethyl acetate layer was dried with magnesium sulfate and concentrated in vacuo. The residue was stirred with pentane and evaporated to give the desired product.

4-Cyclopropylamino-2-methylsulfanyl-pyrimidine-5-carboxylic acid ethyl este

Using procedure A, 4-chloro-2-methylsulfanyl-pyrimidine-5-carboxylic acid ethyl ester and 2.16 g (37.8 mmol) of cyclopropylamine were reacted to give 7.80 g (90%) of the title compound as a solid: mp 41° C.–42° C. MS (APCI) (m+1)/z 254.0. Analysis calculated for $C_{11}H_{15}N_3SO_2$: C, 52.16; H, 5.97; N, 16.59. Found: C, 52.26; H, 5.82; N, 16.53.

3) Preparation of Alcohols

Procedure B

General Procedure for the Parallel Synthesis of 4-Substituted-2-methylamino-pyrimidin-5-yl)-methanols (4-Cyclopropylamino-2-methylamino-pyrimidin-5-yl)-methanol Into an Argonaut Technologies' Quest 205 100 mL reactor was added 1.5 equivalents of 1 M LAH in THF. To the LAH solution was added 3.90 g (15.4 mmol) of 4-cyclopropylamino-2-methylsulfanyl-pyrimidine-5-carboxylic acid ethyl ester prepared above. The reaction mixture was agitated overnight under a nitrogen atmosphere at room temperature. The reaction was quenched by sequential addition of 0.87 mL water, followed by 0.87 mL of 15% NaOH solution, and finally 2.61 mL of water. The reaction was filtered and the residue was washed with THF. The THF solutions were combined and concentrated in vacuo. The residue was stirred with pentane and evaporated to give 2.99 g (92%) of (4-cyclopropylamino-2-methylamino-pyrimidin-5-yl)-methanol as a solid: mp 139° C.–140° C. MS (APCI) (m+1)/z 212.0. Analysis calculated for $C_9H_{11}N_3SO \cdot 0.10 H_2O$: C, 50.73; H, 6.24; N, 19.72. Found: C, 50.68; H, 6.09; N, 19.36.

4) Preparation of Aldehydes

Procedure C

General Procedure for the Synthesis of 4-Substituted-2-methylsulfanyl-pyrimidine-5-carbaldehydes

To a solution of 4-substituted-2-methylamino-pyrimidin-5-yl)-methanol prepared above in 100 mL of $CHCl_3$ was added 9 equivalents of $MnO_2$. The reaction was stirred at room temperature overnight then filtered through Celite. The filter pad was washed with $CHCl_3$ and the filtrate was concentrated in vacuo. The residue was stirred with pentane and evaporated to give the desired product.

4-Cyclopropylamino-2-methylsulfanyl-pyrimidine-5-carbaldehyde

Using Procedure C, 2.88 g (13.6 mmol) of (4-cyclopropylamino-2-methylamino-pyrimidin-5-yl)-methanol gave 2.65 g (93%) of the title compound as a white solid: mp 69.5° C.–70° C. MS (APCI) (m+1)/z 210.1 Analysis calculated for $C_9H_{11}N_3SO$: C, 51.66; H, 5.30; N, 20.08. Found: C, 51.81; H, 5.21; N, 19.83.

5) Preparation of Imines

(5-[(2,6-Difluoro-3,5-dimethoxy-phenylimino)-methyl]-2-methylsulfanyl-pyrimidin-4-yl)-ethyl-amine

In a 500-mL round bottom flask, 3.00 g (15.86 mmol) of 2,6-difluoro-3,5-dimethoxy-phenylamine and 3.13 g (15.86 mmol) of 4-ethylamino-2-methylsulfanyl-pyrimidine-5-carbaldehyde in 150 mL of toluene with 1.11 g (4.76 mmol) of camphorsulfonic acid was fitted with a Dean Stark trap and heated at reflux. During the day, the toluene was drained 3 times from the finger, replenished with 100 mL of the solvent and continued heating at reflux under nitrogen atmosphere overnight. The toluene was concentrated in vacuo and dried to give 7.19 g (quantitative) of the title compound. No further purification was necessary. MS (APCI) (m+1)/z 369.1.

Procedure D

General Procedure for the Condensation of Anilines with Aldehydes (4)

Cyclopropyl-(5-[(2,6-difluoro-3,5-dimethoxy-phenylimino)-methyl]-2-methylsulfanyl-pyrimidin-4-yl)-amine

To a solution of the 7.00 g (33.4 mmol) of 4-cyclopropylamino-2-methylsulfanyl-pyrimidine-5-carbaldehyde in 500 mL of toluene was added 6.33 g 33.4 mmol, 1 equivalent) of 2,6-difluoro-3,5-dimethoxy-phenylamine and 1.94 g (8.36 mmol, 0.25 equivalents) of camphorsulfonic acid. The reaction was warmed to reflux and the formed water was removed with the aid of a Dean-Stark trap. After reacting for 48 hours, the reaction was concentrated in vacuo. The residue was stirred with ether and filtered. The filter pad was dissolved in dichloromethane, stirred with silica gel, and concentrated in vacuo. The residue was placed in the sample injection module of a Biotage FLASH 75 chromatographic apparatus. Chromatography of the crude material down a Biotage 500 g silica gel column with 2:1 hexane/ethyl acetate, then 1:1 hexane/ethyl acetate and finally 9:1 ethyl acetate/ethanol gave 8.92 g (70%) of title compound as a solid: mp 172° C.–174° C. MS (APCI) (m+1)/z 381.0 Analysis calculated for $C_{17}H_{18}F_2N_4SO_2$: C, 53.67; H, 4.77; N, 14.73. Found: C, 53.54; H, 4.58; N, 14.61.

Cyclopentyl-(5-[(2,6-difluoro-3,5-dimethoxy-phenylimino)-methyl]-2-methylsulfanyl-pyrimidin-4-yl)-amine

In a 1-L round bottom flask, 10.00 g (0.0528 mol) of 2,6-difluoro-3,5-dimethoxy-phenylamine and 12.42 g (0.0523 mol) of 4-cyclopentylamino-2-methylsulfanyl-pyrimidine-5-carbaldehyde in 500 mL of toluene with 3.65 g (0.0157 mol) of camphorsulfonic acid was fitted with a Dean Stark trap and heated at reflux. During the day, the toluene was drained three times from the finger and continued heating at reflux under nitrogen atmosphere overnight. The toluene was concentrated in vacuo and dried to give 25.30 g (quantitative) of the title compound. No further purification was necessary. MS (APCI) (m+1)/z 409.2.

Cyclopentyl-{5-[(3-ethoxy-2,6-difluoro-phenylimino)-methyl]-2-methylsulfanyl-pyrimidin-4-yl}-amine

To a solution of the 8.22 g (34.7 mmol) of 4-cyclopentylamino-2-methylsulfanyl-pyrimidine-5-carbaldehyde in 170 mL of toluene was added 6.00 g 34.7 mmol, 1 equivalent) of 3-ethoxy-2,6-difluoro-phenylamine and 2.01 g (8.66 mmol, 0.25 equivalents) of camphorsulfonic acid. The reaction was warmed to reflux and the formed water was removed with the aid of a Dean-Stark trap. After reacting for 48 hours, the reaction was concentrated in vacuo. The residue was dissolved in dichloromethane and neutralized with a saturated aqueous solution of sodium bicarbonate. The resulting emulsion was filtered through fiberglass filter paper. The methylene chloride layer was isolated from the filtrate, then washed first with a saturated aqueous solution of sodium bicarbonate, followed by a saturated aqueous solution of sodium chloride. The methylene chloride layer was dried with magnesium sulfate and concentrated in vacuo. The residue was dissolved in dichloromethane, stirred with silica gel, and concentrated in vacuo. The residue was placed in the sample injection module of a Biotage FLASH 75 chromatographic apparatus. Chromatography of the crude material on a Biotage 500 g silica gel column with 4:1 hexane/ethyl acetate gave 11.1 g (82%) of the title compound as a solid: mp 136° C.–141° C. MS (APCI) (m+1)/z 393.2 Analysis calculated for $C_{19}H_{22}F_2N_4SO$: C, 58.15; H, 5.65; N, 14.28. Found: C, 58.22; H, 5.68; N, 14.26.

6) Preparation of Amines—(Reduction of Imines)

(5-[(2,6-Difluoro-3,5-dimethoxy-phenylamino)-methyl]-2-methylsulfanyl-pyrimidin-4-yl)-ethyl-amine

A solution of 7.19 g (assume 15.86 mmol) of (5-[(2,6-difluoro-3,5-dimethoxy-phenylimino)-methyl]-2-methylsulfanyl-pyrimidin-4-yl)-ethyl-amine in 130 mL of anhydrous tetrahydrofuran was cooled to 0° C. using an ice/acetone bath. The cooled mixture was treated dropwise via syringe with 23.79 mL (23.79 mol) of 1 M solution of lithium aluminum hydride in tetrahydrofuran which resulted initially with vigorous bubbling. The resulting mixture continued to stir at 0° C. for 1 hour under nitrogen atmosphere. The ice bath was removed and the reaction mixture was allowed to warm up to room temperature and continued stirring at room temperature overnight. The reaction mixture was cooled to 0° C. using an ice/acetone bath and quenched by the slow addition of 23.79 mL of water, 23.79 mL of 15% sodium hydroxide and 47.58 mL of water. The salts were filtered over a bed of Celite and removed the tetrahydrofuran in vacuo. The residue was redissolved in dichloromethane and filtered again. The layers were separated and dried the organic layer over sodium sulfate, filtered and evaporated.

The crude product was purified using medium-pressure chromatography eluting with 2:1 hexanes/ethyl acetate to give 4.45 g (76%) of the title compound: mp 95° C.–99° C. MS (APCI) (m+1)/z 371.1.

Procedure E

General Procedure for the Reduction of Imines

Cyclopropyl-(5-[(2,6-difluoro-3,5-dimethoxy-phenylamino)-methyl]-2-methylsulfanyl-pyrimidin-4-yl)-amine A solution of in 8.61 g (22.6 mmol) of cyclopropyl-(5-[(2,6-difluoro-3,5-dimethoxy-phenylimino)-methyl]-2-methylsulfanyl-pyrimidin-4-yl)-amine in 400 mL of dry THF was cooled in an ice/water bath. To the cooled solution was added dropwise equivalent (22.6 mL, 22.6 mmol) of a 1 M LAH solution in THF. The reaction was stirred cold for 2 hours and then quenched by sequential addition of 0.4 mL water, followed by 1.6 mL of 15% NaOH solution, and finally 0.88 mL of water. The reaction was filtered through Celite and the filter pad was washed well with THF. The THF filtrate was concentrated in vacuo. The residue was dissolved in dichloromethane, washed with a saturated solution of NaCl, and concentrated in vacuo. Stirring the residue with diethyl ether and concentrating the suspension in vacuo gave 8.38 g (97%) of the title compound as a solid: mp 48° C.–50° C. MS (APCI) (m+1)/z 383.4 Analysis calculated for $C_{17}H_{20}F_2N_4SO_2$: C, 53.39; H, 5.27; N, 14.65. Found: C, 53.44; H, 5.29; N, 14.31.

Cyclopentyl-(5-[(2,6-difluoro-3,5-dimethoxy-phenylamino)-methyl]-2-methylsulfanyl-pyrimidin-4-yl)-amine A solution of 25.30 g (assume 0.0523 mol) of (5-[(2,6-difluoro-3,5-dimethoxy-phenylimino)-methyl]-2-methylsulfanyl-pyrimidin-4-yl)-ethyl-amine in 425 mL of anhydrous tetrahydrofuran was cooled to 0° C. using an ice/acetone bath. The cooled mixture was treated dropwise via syringe with 78.50 mL (0.0785 mol) 1 M solution of lithium aluminum hydride in tetrahydrofuran which resulted initially with vigorous bubbling. The resulting mixture continued to stir at 0° C. for 1 hour under nitrogen atmosphere. The ice bath was removed and the reaction mixture was allowed to warm up to room temperature and continued stirring at room temperature overnight. The reaction mixture was cooled to 0° C. using an ice/acetone bath and quenched by the slow addition of 78.50 mL of water, 78.50 mL of 15% sodium hydroxide and 157 mL of water. The salts were filtered over a bed of Celite and removed the tetrahydrofuran in vacuo. The residue was redissolved in dichloromethane and filtered again. The layers were separated and dried the organic layer over sodium sulfate, filtered and evaporated. The crude product was purified using medium-pressure chromatography eluting with a gradient of 2:1 to 1:1 hexanes/ethyl acetate to give 16.34 g (76%) of title compound. MS (APCI) (m+1)/z 411.1.

Cyclopentyl-{5-[(3-ethoxy-2,6-difluoro-phenylamino)-methyl]-2-methylsulfanyl-pyrimidin-4-yl}-amine A solution of 8.00 g (20.4 mmol) cyclopentyl-{5-[(3-ethoxy-2,6-difluoro-phenylimino)-methyl]-2-methylsulfanyl-pyrimidin-4-yl }-amine prepared above, in 200 mL dry THF, was cooled in an ice / water bath. To the cooled solution was added dropwise 1 equivalent (20.4 m, 20.4 mmol) of a 1 M LAH solution in THF. The reaction was stirred cold for 4.5 hours and then warmed to 50° C. for 3.5 hours. The reaction was cooled to room temperature, treated with another 0.5 equivalent (11.0 mL, 11.0 mmol) of 1 M LAH solution in THF, and stirred at room temperature overnight. The reaction was quenched by sequential addition of 1.3 mL water, followed by 5.2 mL of 15% NaOH solution, and finally 2.9 mL of water. The reaction was filtered through Celite and the filter pad was washed well with THF. The THF filtrate was concentrated in vacuo. The residue was dissolved in dichloromethane, washed with a saturated solution of NaCl, and concentrated in vacuo to give 8.03 g (100%) of the title compound as a waxy solid: MS (APCI) (m+1)/z 395.1. Analysis calculated for $C_{19}H_{24}F_2N_4SO$: C, 57.85; H, 6.13; N, 14.20. Found: C, 57.92; H, 6.19; N, 14.01.

7) Formation of Pyrimidine Pyrimidinones 3-(2,6-Difluoro-3,5-dimethoxy-phenyl)-1-ethyl-7-methylsulfanyl-3,4-dihydro-1H-pyrimido[4,5-d]pyrimidin-2-one A solution of 4.92 g (11.58 mmol) of (5-[(2,6-difluoro-3,5-dimethoxy-phenylamino)-methyl]-2-methylsulfanyl-pyrimidin-4-yl)-ethyl-amine in 85 mL of anhydrous tetrahydrofuran was cooled to 0° C. using an ice/acetone bath. The reaction mixture was treated with 1.16 g (28.95 mmol) of sodium hydride and continued stirring at 0° C. for 30 minutes. After 30 minutes, 5.63 g (34.74 mmol) of 1,1'-carbonyldiimidazole was added and continued to stir at 0° C. for an additional 30 minutes. After 1 hour, the ice bath was removed and the reaction mixture was allowed to warm up to room temperature. The reaction mixture heated at reflux overnight under nitrogen atmosphere. Evaporated the tetrahydrofuran and partitioned the residue between dichloromethane and water. The aqueous layer was extracted one time with 250 mL dichloromethane. The dichloromethane extracts were combined, dried over sodium sulfate, filtered and evaporated. The crude product was purified using medium-pressure chromatography eluting with 2:1 hexanes/ethyl acetate to give 4.23 g (92%) of the title compound: mp 165° C.–168° C. MS (APCI) (m+1)/z 397.1.

Procedure F

1-Cyclopropyl-3-(2,6-difluoro-3,5-dimethoxy-phenyl)-7-methylsulfanyl-3,4-dihydro-1H-pyrimido[4,5-d]pyrimidin-2-one A solution of 7.66 g (20.0 mmol) of cyclopropyl-(5-[(2,6-difluoro-3,5-dimethoxy-phenylamino)-methyl]-2-methylsulfanyl-pyrimidin-4-yl)-amine in 150 mL of dry THF was cooled to 0° C. To this solution was added 2.00 g (50.1 mmol, 2.5 equivalents) of NaH as a 60% oil suspension. The reaction was stirred for 0.5 hour, the ice bath was removed, and the reaction was stirred for another 0.5 hour. To the reaction was added 9.74 g (60.1 mmol, 3.0 equivalents) of CDI. After 0.5 hour the reaction was warmed to reflux for 24 hous.r The reaction was concentrated in vacuo and the residue was partitioned between dichloromethane and a saturated solution of ammonium chloride. The dichloromethane layer was washed again with ammonium chloride and then once with a saturated solution of NaCl, dried, and concentrated in vacuo. The residue was stirred with diethyl ether and the suspension filtered to give 7.73 g (93%) of the title compound as a solid: mp 173° C.–176° C. MS (APCI) (m+1)/z 409.1 Analysis calculated for $C_{18}H18F_2N_4SO_3$: C, 52.93; H, 4.44; N, 13.72. Found: C, 52.74; H, 4.34; N, 13.80.

1-Cyclopentyl-3-(2,6-difluoro-3,5-dimethoxy-phenyl)-7-methylsulfanyl-3,4-dihydro-1H-pyrimido[4,5-d]pyrimidin-2-one A solution of 16.33 g (0.0398 mol) of cyclopentyl-(5-[(2,6-difluoro-3,5-dimethoxy-phenylamino)-methyl]-2-methylsulfanyl-pyrimidin-4-yl)-amine in 288 mL of anhydrous tetrahydrofuran was cooled to 0° C. using an ice/acetone bath. The reaction mixture was treated with 3.98 g (0.0995 mol) of sodium hydride and continued stirring at 0° C. for 30 minutes. After 30 minutes, 19.35 g (0.019 mol) 1,1'-carbonyldiimidazole was added and continued to stir at 0° C. for an additional 30 minutes. After 1 hour, the ice bath was removed and the reaction mixture was allowed to warm up to room temperature. The reaction mixture heated at reflux overnight under nitrogen atmosphere. Evaporated the tetrahydrofuran and partitioned the residue between dichloromethane and water. The aqueous layer was extracted one time with 500 mL dichloromethane. The dichloromethane extracts were combined, dried over sodium sulfate, filtered and evaporated. There was a portion of the crude material that did not dissolve in the eluent. Filtered the solid and dried in the housevac oven overnight to give the title compound, 6.80 g of crop 1. The remaining crude material was purified using medium pressure-chromatography, eluting with a gradient of 2:1 hexanes/ethyl acetate to 1:1 hexanes/ethyl acetate to give the title compound as a white solid, 8.74 g of crop 2. Combined the crops to give a total of 15.54 g (90%) of the title compound. MS (APCI) (m+1)/z 437.1.

1-Cyclopentyl-3-(3-ethoxy-2,6-difluoro-phenyl)-7-methylsulfanyl-3,4-dihydro-1H-pyrimido[4,5-d]pyrimidin-2-one A solution of 1.00 g (2.53 mmol) of cyclopentyl-{5-[(3-ethoxy-2,6-difluoro-phenylamino)-methyl]-2-methylsulfanyl-pyrimidin-4-yl}-amine in 20 mL of dry THF was cooled to 0C. To this solution was added 0.25 g (6.33 mmol, 2.5 equivalents) of NaH as a 60% oil suspension. The reaction was stirred for 0.5 hour, the ice bath was removed, and the reaction was stirred for another 0.5 hour. To the reaction was added 1.24 g (7.60 mmol, 3.0 equivalents) of CDI. After 0.5 hour the reaction was warmed to reflux for 24 hours. The reaction was concentrated in vacuo and the residue was partitioned between dichloromethane and a saturated solution of ammonium chloride. The dichloromethane layer was washed again with ammonium chloride and then once with a saturated solution of NaCl, dried, and concentrated in vacuo. The crude material was eluted onto a Biotage 90 g silica gel column that had been pre-equilibrated with 3:1 hexane/ethyl acetate using the same solvent mixture. Fractions of pure product were combined and concentrated in vacuo to give 0.86 g (81%) of the title compound as a foam: mp 45° C. dec. MS (APCI) (m+1)/z 421.2 Analysis calculated for $C_{20}H_{22}F_2N_4SO_2$: C, 57.13; H, 5.27; N, 13.32. Found: C, 57.12; H, 5.08; N, 13.21.

8) Formation of Sulfoxides 3-(2,6-Difluoro-3,5-dimethoxy-phenyl)-1-ethyl-7-methylsulfinyl-3,4-dihydro-1H-pyrimido[4,5-d]pyrimidin-2-one A solution of 4.23 g (10.67 mmol) of 3-(2,6-difluoro-3,5-dimethoxy-phenyl)-1-ethyl-7-methylsulfanyl-3,4-dihydro-1H-pyrimido[4,5-d]pyrimidin-2-one in 90 mL of chloroform was treated with 3.35 g (12.80 mmol) of 3-phenyl-2-(phenylsulfonyl)-oxaziridine and stirred at room temp. under $N_2$ atmosphere overnight. Crude product was purified by medium-pressure chromatography eluting with straight ethyl acetate and a gradient of 1% to 3% MeOH in chloroform to give 4.45 g (quantitative) title compound. MS (APCI) (m+1)/z 413.1.

Procedure H

General Procedure for the Synthesis of Sulfoxides

1-Cyclopropyl-3-(2,6-difluoro-3,5-dimethoxy-phenyl)-7-methanesulfinyl-3,4-dihydro-1H-pyrimido[4,5-d]pyrimidin-2-one 0.64 g (1.57 mmol) of 1-cyclopropyl-3-(2,6-difluoro-3,5-dimethoxy-phenyl)-7-methylsulfanyl-3,4-dihydro-1H-pyrimido[4,5-d]pyrimidin-2-one in 20 mL of $CHCl_3$ was reacted with (±)-trans-2-benzenesulfonyl-3-phenyl-oxaziridine. The reaction was stirred overnight at room temperature and then concentrated in vacuo. The reaction was placed directly on a Biotage 90 g silica gel column. Chromatography, eluting with 9:1 ethyl acetate/ethanol, gave 0.66 g (99%) of the title compound as a solid: mp 198.5° C.–199.5° C. MS (APCI) (m+1)/z 425.0Analysis calculated for $C_{18}H_{18}F_2N_4SO_4$: C, 50.94; H, 4.27; N, 13.20. Found: C, 51.13; H, 4.13; N, 12.98.

1-Cyclopentyl-3-(2,6-difluoro-3,5-dimethoxy-phenyl)-7-methylsulfanyl-3,4-dihydro-1H-pyrimido[4,5-d]pyrimidin-2-one A solution of 15.53 g (0.0356 mol) of 1-cyclopentyl-3-(2,6-difluoro-3,5-dimethoxy-phenyl)-7-methylsulfanyl-3,4-dihydro-1H-pyrimido[4,5-d]pyrimidin-2-one in 295 mL of chloroform was treated with 11.16 g (0.0427 mol) of 3-phenyl-2-(phenylsulfonyl)-oxaziridine and stirred at room temperature under nitrogen atmosphere overnight. The reaction mixture was evaporated in vacuo to approximately 30 mL of volume. The crude product was purified using medium-pressure chromatography eluting with a gradient of straight ethyl acetate to 9:0.5:0.25 ethyl acetate/methanol/triethylamine to give 15.54 g (96%) of the title compound: mp 167° C.–169° C. MS (APCI) (m+1)/z 453.1.

3-(3-Ethoxy-2,6-difluoro-phenyl)-1-(1-ethyl-propyl)-7-methanesulfinyl-3,4-dihydro-1H-pyrimido[4,5-d]pyrimidin-2-one Using procedure H, 0.82 g (1.95 mmol) of 1-Cyclopentyl-3-(3-ethoxy-2,6-difluoro-phenyl)-7-methylsulfanyl-3,4-dihydro-1H-pyrimido[4,5-d]pyrimidin-2-one in 15 mL of $CHCl_3$ was reacted with (±)-trans-2-benzenesulfonyl-3-phenyl-oxaziridine. In this instance the reaction was run for 6 hours and the crude residue was placed directly on a Biotage 90 g silica gel column. Chromatography, eluting with ethyl acetate, gave 0.79 g (94%) of the title compound as a solid: mp 57° C. dec. MS (APCI) (m+1)/z 437.1 Analysis calculated for $C_{20}H_{22}F_2N_4SO_3$: C, 55.04; H, 5.08; N, 12.84. Found: C, 54.91; H, 5.10; N, 12.54.

10) Synthesis of Amine Side Chains (4S,5R)-2,2,5-Trimethyl-[1,3]dioxolane-4-carboxylic Acid Benzylamide A flask was charged with 70 mL dry tetrahydrofuran, 3.17 g (17.7 mmol) (4S,5R)-2,2,5-trimethyl[1,3]dioxolane-4-carbonyl chloride, and the solution was cooled in a 0° C. bath. To this solution, 3.48 mL (31.9 mmol) benzyl amine was slowly added, and a precipitate formed immediately. The reaction mixture was stirred for 1 hour at 0° C. and 1 hour at room temperature. The reaction mixture was filtered through Celite to remove salts, and the tetrahydrofuran was removed under reduced pressure giving 4.41 g (100%) of the title compound as a yellow oil. No further purification was necessary. MS (APCI) (m+1)/z 250.1.

(2S,3R)-N-Benzyl-2,3-dihydroxy-butyramide

A flask was charged with 4.23 g (17.0 mmol) (4S,5R)-2,2,5-trimethyl-[1,3]dioxolane-4-carboxylic acid benzylamide, 30 mL acetonitrile, and 17 mL 0.5 M aqueous hydrochloric acid solution. This mixture was stirred overnight at room temperature. The solution was made neutral by the addition of 1 M aqueous sodium hydroxide solution. The solvent was removed under reduced pressure, and the crude residue was dried in a vacuum oven. The dry, crude material was purified by column chromatography (20:1 dichloromethane/methanol) to give 3.03 g (85%) of the title compound as a white solid. MS (APCI) (m+1)/z 210.1.

(2R,3R)-1-Benzylamino-butane-2,3-diol

A flask was charged with 3.03 g (14.5 mmol) (2S,3R)-N-benzyl-2,3-dihydroxy-butyramide, 60 mL dry THF, and the mixture was cooled to 0° C. under a nitrogen atmosphere. To this solution, 1.65 g (43.5 mmol) lithium aluminum hydride powder was added in small portions. The mixture was stirred at 0° C. for 1 hour, allowed to warm to room temperature, and then heated at reflux overnight. The reaction mixture was then cooled to 0° C. and quenched by the slow addition of 1.65 mL water, 1.65 mL 15% aqueous sodium hydroxide solution, and 4.95 mL water, sequentially. The solids were filtered off, and the solvent was removed under reduced pressure. The crude material was purified by column chromatography (1:1 dichloromethane/ methanol) to give 1.41 g (50%) of the title compound as a white solid. MS (APCI) (m+1)/z 196.1.

(2R,3R)-1-Amino-butane-2,3-diol

A pressure safe flask was charged with 1.41 g (7.22 mmol) (2R,3R)-1-benzylamino-butane-2,3-diol and 30 mL methanol and palladium on carbon catalyst. This solution was stirred overnight under an atmosphere of hydrogen. The catalyst was removed by filtration through Celite, and the solvent was removed under reduced pressure giving 0.726 g (96%) of the title compound as a yellow oil which crystallized on standing. MS (APCI) (m+1)/z 106.1.

9) Formation of Final Products—Displacement of Sulfoxides and Derivatives

Procedure J

General Procedure for Parallel Synthesis of 1-Substituted-7-[4-(2-diethylamino-ethoxy)-phenylamino]-3-(3,5-dimethoxy-phenyl)-3,4-dihydro-1H-pyrimido[4,5-d]pyrimidin-2-ones Into an Argonaut Technologies' Quest 205 100 mL reactor was added the sulfoxide (20) prepared above. To the reaction was added 2 equivalents of 4-(2-diethylamino-ethoxy)-phenylamine dissolved in 30 mL of dry CH$_3$CN followed by 3 equivalents of trifluoroacetic acid. The reaction mixture was agitated at 65° C. for 37 hours under a nitrogen atmosphere. The reaction was drained from the reaction vessel, evaporated, and redissolved in 50 mL of dichloromethane. The dichloromethane solution was added back into the reaction vessel followed by 30 mL of a saturated solution of sodium bicarbonate. The reaction was agitated and the dichloromethane removed. The dichloromethane solution was washed again with a saturated solution of sodium bicarbonate and then with a saturated solution of sodium chloride. The dichloromethane layer was dried with magnesium sulfate and concentrated in vacuo. The residue was suspended in 20 mL of diethyl ether. To the suspension was added a solution of 2 equivalents of triethylamine in 5 mL of diethyl ether followed by a solution of 1.1 equivalents of di-tert-butyl dicarbonate in 5 mL of diethyl ether. The reaction was agitated at room temperature for 4 hours. The reaction was cooled to 0° C. and diluted with 30 mL of hexane. The suspension was filtered. The filter pad was washed with 1:1 diethyl ether/hexane, and dried at 45° C. overnight in vacuo to give desired product.

Procedure K

General Procedure for the Reaction of Substituted Alkylamines with Sulfoxides

To a sulfoxide prepared above was added a solution of 3 equivalents of amine in dry dioxane. The reaction was warmed to 75° C. for 24 hours, then concentrated in vacuo. The residue was dissolved in dichloromethane. The dichloromethane solution was extracted twice with a saturated solution of sodium bicarbonate then once with a saturated solution of sodium chloride, dried with magnesium sulfate, and concentrated in vacuo. The crude product was chromatographed using a Biotage Quad 3 chromatographic apparatus with a 90 g silica gel column and the appropriate solvent systems. Pure fractions were combined and concentrated in vacuo. The residue was stirred with ether and concentrated in vacuo to give the desired product.

Procedure L

General Procedure for the Reaction of Substituted Alkylamines with Sulfoxides

To a sulfoxide prepared above was added a solution of 3 equivalents of amine and 1.1 equivalents of camphorsulfonic acid in dry dioxane. The reaction was warmed to 75° C. for 24 hours, then concentrated in vacuo. The residue was dissolved in dichloromethane. The dichloromethane solution was extracted twice with a saturated solution of sodium bicarbonate then once with a saturated solution of sodium chloride, dried with magnesium sulfate, and concentrated in vacuo. The crude product was chromatographed using a Biotage Quad 3 chromatographic apparatus with a 90 g silica gel column and the appropriate solvent systems. Pure fractions were combined and concentrated in vacuo. The residue was stirred with ether and concentrated in vacuo to give the desired product.

This invention will be further understood by the following non-limiting examples.

EXAMPLE 1

1-Cyclopentyl-7-(4-diethylamino-butylamino)-3-(2,6-difluoro-3-hydroxy-5-methoxy phenyl)-3,4-dihydro-1H-pyrimido[4,5-d]pyrimidin-2-one To a solution of sodium ethylthiolate [generated from sodium hydride (200 mg, 8.32 mmol) and ethanethiol (616 µL, 8.32 mmol) in dimethylformamide (20 mL)], 1-Cyclopentyl-7-(4-diethylamino-butylamino)-3-(2,6-difluoro-3,5-dimethoxy-phenyl)-3,4-dihydro-1H-pyrimido[4,5-d]pyrimidin-2-one in dimethylformamide (8 mL) was added. The resulting solution was then stirred at 75° C. for 90 minutes. The solvent was removed under reduced pressure to afford a light brown oil. Dichloromethane (100 mL) and water (20 mL) were added. The bilayer thus afforded was then stirred vigorously while 4 N hydrochloric acid was added. Enough hydrochloric acid was added until the aqueous layer reached pH=5. The layers were separated; the aqueous layer was extracted with dichloromethane (2×80 mL). The organic layers were combined and set aside. Saturated aqueous sodium chloride (20 mL) was to the aqueous layers and was extracted with ethyl acetate (2×80 mL). The organic layers were combined, dried (magnesium sulfate), filtered, and concentrated under reduced pressure. To the yellow oil (794 mg) thus afforded, hexanes were added to remove non-polar impurities. The supernatant was removed, and the remaining residue was placed in vacuo. The oil was purified via reverse phase HPLC to give the title compound (289 mg, 54%) as a clear amber gum: MS (APCI) 519.2, 520.2.

EXAMPLE 2

1-Cyclopentyl-7-(4-diethylamino-butylamino)-3-(2, 6-difluoro-3,5-dimethoxy-phenyl)-3,4-dihydro-1H-pyrimido[4,5-d]pyrimidin-2-one In a 1-L round bottom flask, 8.00 g (17.78 mmol) of 1-cyclopentyl-3-(2,6-difluoro-3,5-dimethoxy-phenyl)-7-methylsulfinyl-3,4-dihydro-1H-pyrimido[4,5-d]pyrimidin-2-one in 260 mL of dioxane was treated with 5.10 g (35.36 mmol) of 4-diethylamino-butylamine and heated at reflux for 10 hours under nitrogen atmosphere. The dioxane was evaporated in vacuo. The crude product was purified using medium-pressure chromatography eluting with a gradient of 9:0.5:0.25 to 9:1:0.5 ethyl acetate/methanol/triethylamine to give 8.14 g (86%) of the title compound as a pure partially crystalline solid. A 50 mg portion of the solid was recrystallized with 25% ethanol in hexanes to give 35 mg of title compound as pure crystalline solid: mp 132° C.–133° C. MS (APCI) (m+1)/z 533.3.

EXAMPLE 3

(S,S)-1-Cyclopentyl-3-(2,6-difluoro-3,5-dimethoxy-phenyl)-7-[(5-hydroxymethyl-2-phenyl-[1,3]dioxolan-4-ylmethyl)-amino]-3,4-dihydro-1H-pyrimido[4,5-d]pyrimidin-2-one (S,S)-1-Cyclopentyl-3-(2,6-difluoro-3,5-dimethoxy-phenyl)-7-[(5-hydroxymethyl-2-phenyl-[1,3]dioxolan-4-ylmethyl)-amino]-3,4-dihydro-1H-pyrimido[4,5-d]pyrimidin-2-one was prepared as in Example 3 using 0.5 g (1.1 mmol) 1-Cyclopentyl-3-(2-fluoro-3,5-dimethoxy-phenyl)-7-methanesulfinyl-3,4-dihydro-1H-pyrimido[4,5-d]pyrimidin-2-one and 0.69 g (3.3 mmol) (S,S)-(5-Aminomethyl-2-phenyl [1,3]dioxolan-4-yl)-methanol. The product was purified by column chromatograph via 5:1 dichloromethane/methanol. This gave 0.59 g (89%) of (S,S)-1-Cyclopentyl-3-(2,6-difluoro-3,5-dimethoxy-phenyl)-7-[(5-hydroxymethyl-2-phenyl-[1,3]dioxolan-4-ylmethyl)-amino]-3,4-dihydro-1H-pyrimido[4,5-d]pyrimidin-2-one as a white solid: MS (APCI) m/z 598.2, 599.3.

EXAMPLE 4

(S,S)-1-Cyclopentyl-3-(2,6-difluoro-3,5-dimethoxy-phenyl)-7-(2,3,4-trihydroxy-butylamino)-3,4-dihydro-1H-pyrimido[4,5-d]pyrimidin-2-one (S,S)-1-Cyclopentyl-3-(2,6-difluoro-3,5-dimethoxy-phenyl)-7-[(5-hydroxymethyl-2-phenyl-[1,3]dioxolan-4-ylmethyl)-amino]-3,4-dihydro-1H-pyrimido[4,5-d]pyrimidin-2-one (0.57 g, 0.95 mmol) was dissolved in 90 mL methanol containing 12 mL 10% HCl acid. The mixture was stirred at room temperature for 9 hours. Adjusted pH=12 by adding 1 M NaOH. Stripped the solvent. The residue was dissolved in methanol. Insoluble NaCl was removed by filtration. The filtrate was evaporated to dryness and the residue was purified by column chromatography (5:1 dichloromethane/methanol) to give 0.275 g (57%) (S,S)-1-cyclopentyl-3-(2, 6-difluoro-3,5-dimethoxy-phenyl)-7-(2,3,4-trihydroxy-butylamino)-3,4-dihydro-1H-pyrimido[4,5-d]pyrimidin-2-one as white solid: mp=160° C (dec.); MS (APCI) m/z 510.1, 511.1.

EXAMPLE 5

1-Cyclopentyl-3-(2,6-difluoro-3,5-dimethoxy-phenyl)-7-(4-hydroxy-cyclohexylamino)-3,4-dihydro-1H-pyrimido[4,5-d]pyrimidin-2-one To a solution of 0.511 g (1.13 mmol) of 1-cyclopentyl-3-(2,6-difluoro-3,5-dimethoxy-phenyl)-7-methylsulfinyl-3,4-dihydro-1H-pyrimido[4,5-d]pyrimidin-2-one was added 0.39 g (3.39 mmol) of trans-4-aminocyclohexanol. The resulting mixture was heated at 1 10° C. oil bath temperature for 2 days under $N_2$ atmosphere. The dioxane was evaporated. The crude product was purified by medium-pressure chromatography eluting with 20:1 dichloromethane/methanol to give 0.50 g (88%) of title compound: mp 208° C.–212° C. (dec). MS (APCI) (m+1)/z 504.2.

EXAMPLE 6

1-Cyclopentyl-3-(2,6-difluoro-3,5-dimethoxy-phenyl)-7-(2-hydroxy-1-hydroxymethyl-ethylamino)-3, 4-dihydro-1H-pyrimido[4,5-d]pyrimidin-2-one 1-Cyclopentyl-3-(2,6-difluoro-3,5-dimethoxy-phenyl)-7-(2-hydroxy-1-hydroxymethyl-ethylamino)-3,4-dihydro-1H-pyrimido[4,5-d]pyrimidin-2-one was prepared as described in Example 5 using 0.50 g (1.11 mmol) of 1-cyclopentyl-3-(2,6-difluoro-3,5-dimethoxy-phenyl)-7-methylsulfinyl-3, 4-dihydro-1H-pyrimido[4,5-d]pyrimidin-2-one and 0.30 g (3.32 mmol) of serinol. The crude product was purified using medium-pressure chromatography eluting with 20:1 dichloromethane/methanol to give 0.38 g (72%) of the title compound: mp 172° C.–174° C. MS (APCI) (m+1)/z 480.1.

EXAMPLE 7

7-(3-Amino-2-hydroxy-propylamino)-1-cyclopentyl-3-(2,6-difluoro-3,5-dimethoxy-phenyl)-3,4-dihydro-1H-pyrimido[4,5-d]pyrimidin-2-one To a solution of 0.50 g (1.11 mmol) of 1-cyclopentyl-3-(2,6-difluoro-3,5–5 dimethoxy-phenyl)-7-methylsulfinyl-3, 4-dihydro-1H-pyrimido[4,5-d]pyrimidin-2-one was added 0.31 g (3.32 mmol) of 1,3-diamino-2-hydroxypropane. The resulting mixture was heated at an oil bath temperature of 95° C. for 18 hours under nitrogen atmosphere. The dioxane was evaporated. The crude product was purified using medium-pressure chromatography eluting with 30:6:1 dichloromethane/ methanol/triethylamine to give 0.273 g (52%) of the title compound: mp 167° C. (dec). MS (APCI) (m+1)/z 479.2.

EXAMPLE 8

1-Cyclopentyl-3-(2,6-difluoro-3,5-dimethoxy-phenyl)-7-[2-(2-hydroxy-ethoxy)-ethylamino]-3,4-dihydro-1H-pyrimido[4,5-d]pyrimidin-2-one 1-Cyclopentyl-3-(2,6-difluoro-3,5-dimethoxy-phenyl)-7-[2-(2-hydroxy-ethoxy)-ethylamino]-3,4-dihydro-1H-pyrimido[4,5-d]pyrimidin-2-one was prepared as described in Example 7 using 0.50 g (1.11 mmol) of 1-cyclopentyl-3-(2,6-difluoro-3,5-dimethoxy-phenyl)-7-methylsulfinyl-3,4-dihydro-1H-pyrimido[4,5-d]pyrimidin-2-one and 0.33 mL (3.32 mmol) of 2-(2-aminoethoxy)ethanol. The crude product was purified using medium-pressure chromatography eluting with 20:1 dichloromethane/methanol to give 0.50 g (92%) of the title compound: mp 160° C.–163° C. MS (APCI) (m+1)/z 494.3.

EXAMPLE 9

1-Cyclopropyl-7-(4-diethylamino-butylamino)-3-(2,6-difluoro-3,5-dimethoxy-phenyl)-3,4-dihydro-1H-pyrimido[4,5-d]pyrimidin-2-one Using Procedure K, 0.63 g (1.48 mmol) of 1-cyclopropyl-3-(2,6-difluoro-3,5-dimethoxy-phenyl)-7-methanesulfinyl-3,4-dihydro-1H-pyrimido[4,5-d]pyrimidin-2-one and 4-(diethylamino)butylamine in 20 mL of dioxane were reacted. Chromatography with 9:1:0.5 ethyl acetate/ethanol/triethylamine gave 0.62 g (83%) of the title compound as a solid: mp 139° C.–141° C. MS (APCI) (m+1)/z 505.2. Analysis calculated for $C_{25}H_{34}N_6F_2O_3$: C, 59.51; H, 6.79; N, 16.66. Found: C, 59.56; H, 6.77; N, 16.49.

EXAMPLE 10

7-(4-Diethylamino-butylamino)-3-(2,6-difluoro-3,5-dimethoxy-phenyl)-1-ethyl-3,4-dihydro-1H-pyrimido[4,5-d]pyrimidin-2-one 7-(4-Diethylamino-butylamino)-3-(2,6-difluoro-3,5-dimethoxy-phenyl)-1-ethyl-3,4-dihydro-1H-pyrimido[4,5-d]pyrimidin-2-one was prepared as described in Example 3 using 0.46 g (1.11 mmol) of 3-(2,6-difluoro-3,5-dimethoxy-phenyl)-1-ethyl-7-methylsulfinyl-3,4-dihydro-1H-pyrimido[4,5-d]pyrimidin-2-one and 0.32 g (2.22 mmol) of 4-diethylamino-butylamine. The crude product was purified using a gradient of 9:1 ethyl acetate/methanol to 9:0.25:0.25 to 9:0.5:0.25 ethyl acetate/methanol/triethylamine to give 0.4833 g (83%) of the title compound: mp 140° C.–141° C. MS (APCI) (m+1)/z 493.2.

EXAMPLE 11

3-(2,6-Difluoro-3,5-dimethoxy-phenyl)-1-ethyl-7-(2-hydroxy-1-hydroxymethyl-ethylamino)-3,4-dihydro-1H-pyrimido[4,5-d]pyrimidin-2-one 3-(2,6-Difluoro-3,5-dimethoxy-phenyl)-1-ethyl-7-(2-hydroxy-1-hydroxymethyl-ethylamino)-3,4-dihydro-1H-pyrimido[4,5-d]pyrimidin-2-one was prepared as described in Example 5 using 0.5 g (1.21 mmol) of 3-(2,6-difluoro-3,5-dimethoxy-phenyl)-1-ethyl-7-methylsulfinyl-3,4-dihydro-1H-pyrimido[4,5-d]pyrimidin-2-one and 0.33 g (3.64 mmol) of serinol. The crude product was purified using medium-pressure chromatography eluting with 20:1 dichloromethane/methanol to give 0.51 g (96%) of the title compound: mp 168° C.–172° C. MS (APCI) (m+1)/z 440.1

EXAMPLE 12

3-(2,6-Difluoro-3,5-dimethoxy-phenyl)-1-ethyl-7-(4-hydroxy-cyclohexylamino)-3,4-dihydro-1H-pyrimido[4,5-d]pyrimidin-2-one 3-(2,6-Difluoro-3,5-dimethoxy-phenyl)-1-ethyl-7-(4-hydroxy-cyclohexylamino)-3,4-dihydro-1H-pyrimido[4,5-d]pyrimidin-2-one was prepared as described in Example 5 using 0.5 g (1.21 mmol) of 3-(2,6-difluoro-3,5-dimethoxy-phenyl)-1-ethyl-7-methylsulfinyl-3,4-dihydro-1H-pyrimido[4,5-d]pyrimidin-2-one and 0.42 g (3.64 mmol) of trans-4-aminocyclohexanol. The crude product was purified using medium-pressure chromatography eluting with 20:1 dichloromethane/methanol to give 0.50 g (89%) of the title compound: mp 198° C.–202° C. MS (APCI) (m+1)/z 464.1.

EXAMPLE 13

1-Cyclopentyl-3-(2,6-difluoro-3,5-dimethoxy-phenyl)-7-(2,3-dihydroxy-butylamino)-3,4-dihydro-1H-pyrimido[4,5-d]pyrimidin-2-one 1-Cyclopentyl-3-(2,6-difluoro-3,5-dimethoxy-phenyl)-7-(2,3-dihydroxy-butylamino)-3,4-dihydro-1H-pyrimido[4,5-d]pyrimidin-2-one was prepared as described in Example 7 using 0.49 g (1.08 mmol) of 1-cyclopentyl-3-(2,6-difluoro-3,5-dimethoxy-phenyl)-7-methylsulfinyl-3,4-dihydro-1H-pyrimido[4,5-d]pyrimidin-2-one and 0.28 g (2.66 mmol) of (2R,3R)-1-amino-butane-2,3-diol. The crude product was purified using medium-pressure chromatography eluting with 20:1 dichloromethane/methanol to give 0.50 g (94%) of the title compound: mp 195° C.–196° C. (dec). MS (APCI) (m+1)/z 494.2.

EXAMPLE 14

1-Cyclopentyl-3-(2,6-difluoro-3,5-dimethoxy-phenyl)-7-(2,3-dihydroxy-propylamino)-3,4-dihydro-1H-pyrimido[4,5-d]pyrimidin-2-one 1-Cyclopentyl-3-(2,6-difluoro-3,5-dimethoxy-phenyl)-7-(2,3-dihydroxy-propylamino)-3,4-dihydro-1H-pyrimido[4,5-d]pyrimidin-2-one was prepared as described in Example 7 using 0.50 g (1.11 mmol) of 1-cyclopentyl-3-(2,6-difluoro-3,5-dimethoxy-phenyl)-7-methylsulfinyl-3,4-dihydro-1H-pyrimido[4,5-d]pyrimidin-2-one and 0.30 g (3.32 mmol) R-(+)-3-amino-1,2-propanediol. The crude product was purified using medium-pressure chromatography eluting with 9:1:0.5 ethyl acetate/methanol/triethylamine to give 0.42 g (78%) of the title compound: mp 118° C.–122° C. MS (APCI) M+1)/z 480.2.

EXAMPLE 15

7-(4-Amino-2,3-dihydroxy-butylamino)-1-cyclopentyl-3-(2,6-difluoro-3,5-dimethoxy-phenyl)-3,4-dihydro-1H-pyrimido[4,5-d]pyrimidin-2-one 7-(4-Amino-2,3-dihydroxy-butylamino)-1-cyclopentyl-3-(2,6-difluoro-3,5-dimethoxy-phenyl)-3,4-dihydro-1H-pyrimido[4,5-d]pyrimidin-2-one was prepared as in Example 2 using 0.5 g (1.1 mmol) 1-cyclopentyl-3-(2-fluoro-3,5-dimethoxy-phenyl)-7-methanesulfinyl-3,4-dihydro-1H-pyrimido[4,5-d]pyrimidin-2-one and 0.397 g (3.3 mmol) 1,4-Diamino-butane-2,3-diol. The final product was purified by column chromatography (40:6:1 dichloromethane/methanol/sat. aqueous ammonium hydroxide solution) giving 0.18 g (32%) of the final product: mp 158° C. (dec.); MS (APCI) m/z 509.1, 510.1.

EXAMPLE 16

1-Cyclopentyl-3-(2-fluoro-3,5-dimethoxy-phenyl)-7-([S,S]-2,3,4-trihydroxy-butylamino)-3,4-dihydro-1H-pyrimido[4,5-d]pyrimidin-2-one 1-Cyclopentyl-3-(2-fluoro-3,5-dimethoxy-phenyl)-7-([S,S]-2,3,4-trihydroxy-butylamino)-3,4-dihydro-1H-pyrimido[4,5-d]pyrimidin-2-one was prepared as in Example 2 using 0.40 g (0.92 mmol) 1-cyclopentyl-3-(2-fluoro-3,5-dimethoxy-phenyl)-7-methanesulfinyl-3,4-dihydro-1H-pyrimido[4,5-d]pyrimidin-2-one and 0.33 g (2.76 mmol) (S,S)-4-amino-1,2,3-butanetriol. The final product was purified by column chromatography (20:1 dichloromethane/methanol) to get 0.05 g (11%) as a white solid: mp 86° C.–88° C.; MS (APCI) m/z 492.2, 493.2.

EXAMPLE 17

3-(2,6-Difluoro-3,5-dimethoxy-phenyl)-1-ethyl-7-[2-(2-hydroxy-ethoxy)-ethylamino]-3,4-dihydro-1H-pyrimido[4,5-d]pyrimidin-2-one 3-(2,6-Difluoro-3,5-dimethoxy-phenyl)-1-ethyl-7-[2-(2-hydroxy-ethoxy)-ethylamino]-3,4-dihydro-1H-pyrimido[4,5-d]pyrimidin-2-one was prepared as described in Example 2 using 0.50 g (1.21 mmol) of 3-(2,6-difluoro-3,5-dimethoxy-phenyl)-1-ethyl-7-methylsulfinyl-3,4-dihydro-1H-pyrimido[4,5-d]pyrimidin-2-one and 0.36 mL (3.64 mmol) of 2-(2-aminoethoxy)ethanol. The crude product was purified using medium-pressure chromatography eluting with 20:1 dichloromethane/methanol to give 0.50 g (91%) of the title compound: mp 159° C.–160° C. MS (APCI) (m+1)/z 454.1.

EXAMPLE 18

7-(4-Amino-2,3-dihydroxy-butylamino)-3-(2,6-difluoro-3,5-dimethoxy-phenyl)-1-ethyl-3,4-dihydro-1H-pyrimido[4,5-d]pyrimidin-2-one 7-(4-Amino-2,3-dihydroxy-butylamino)-3-(2,6-difluoro-3,5-dimethoxy-phenyl)-1-ethyl-3,4-dihydro-1H-pyrimido[4,5-d]pyrimidin-2-one was prepared as in Example 2 using 0.5 g (1.2 mmol) 3-(2,6-difluoro-3,5-dimethoxy-phenyl)-1-ethyl-7-methanesulfinyl-3,4-dihydro-1H-pyrimido[4,5-d]pyrimidin-2-one and 0.433 g (3.6 mmol) (S,S)-1,4-diamino-butane-2,3-diol. The final product was purified by column chromatography (40:6:1 dichloromethane/methanol/sat. aqueous ammonium hydroxide solution) which gave 0.24 g (43%) of the final product as a white solid: mp 115° C. (dec.); MS (APCI) m/z 469.1, 470.2.

EXAMPLE 19

7-{3-[Bis-(2-hydroxy-ethyl)-amino]-propylamino}-3-(2,6-difluoro-3,5-dimethoxy-phenyl)-1-ethyl-3,4-dihydro-1H-pyrimido[4,5-d]pyrimidin-2-one 3-(2,6-Difluoro-3,5-dimethoxy-phenyl)-1-ethyl-7-methylsulfinyl-3,4-dihydro-1H-pyrimido[4,5-d]pyrimidin-2-one was prepared using 0.50 g (1.21 mmol) of 3-(2,6-difluoro-3,5-dimethoxy-phenyl)-1-ethyl-7-methylsulfinyl-3,4-dihydro-1H-pyrimido[4,5-d]pyrimidin-2-one and 0.59 g (3.64 mmol) of N-(3-amino-propyl)diethanolamine. The crude product was purified using medium-pressure chromatography eluting with a gradient of 9:1 ethyl acetate/methanol to 9:1:0.25 to 9:1:0.5 ethyl acetate/methanol/triethylamine to give 0.43 g (69%) of the title compound: mp 128° C.–129° C. MS (APCI) (m+1)/z 511.2.

EXAMPLE 20

1-Cyclopentyl-3-(2,6-difluoro-3,5-dimethoxy-phenyl)-7-(2,3-dihydroxy-propylamino)-3,4-dihydro-1H-pyrimido[4,5-d]pyrimidin-2-one 1-Cyclopentyl-3-(2,6-difluoro-3,5-dimethoxy-phenyl)-7-(2,3-dihydroxy-propylamino)-3,4-dihydro-1H-pyrimido[4,5-d]pyrimidin-2-one was prepared as described in Example 2 using 1.00 g (2.21 mmol) of 1-cyclopentyl-3-(2,6-difluoro-3,5-dimethoxy-phenyl)-7-methylsulfinyl-3,4-dihydro-1H-pyrimido[4,5-d]pyrimidin-2-one and 0.60 g (6.63 mmol) of S-(−)-3-amino-1,2-propanediol. The crude product was purified using medium-pressure chromatography eluting with 9:1:0.5 ethyl acetate/methanol/triethylamine to give 0.98 g (92%) of the title compound: mp 179° C.–182° C. MS (APCI) (m+1)/z 480.2.

EXAMPLE 21

3-(2,6-Difluoro-3,5-dimethoxy-phenyl)-7-(2,3-dihydroxy-butylamino)-1-ethyl-3,4-dihydro-1H-pyrimido[4,5-d]pyrimidin-2-one 3-(2,6-Difluoro-3,5-dimethoxy-phenyl)-7-(2,3-dihydroxy-butylamino)-1-ethyl-3,4-dihydro-1H-pyrimido[4,5-d]pyrimidin-2-one was prepared as described in Example 7 using 0.40 g (0.97 mmol) of 3-(2,6-difluoro-3,5-dimethoxy-phenyl)-1-ethyl-7-methylsulfinyl-3,4-dihydro-1H-pyrimido[4,5-d]pyrimidin-2-one and 0.245 g (2.33 mmol) of (2R,3R)-1-amino-butane-2,3-diol. The crude product was purified using medium-pressure chromatography eluting with 20:1 dichloromethane/methanol to give 0.40 g (91%) of title compound: mp 171° C.–173° C. MS (APCI) (m+1)/z 454.2.

EXAMPLE 22

Ethyl-4-[3-(2,6-difluoro-3,5-dimethoxy-phenyl)-7-methylamino-2-oxo-3,4-dihydro-2H-pyrimido[4,5-d]pyrimidin-1-yl]-cyclohexanecarboxylate The title compound was prepared as follows:

a) 5-[2,6-Difluoro-3,5-dimethoxy-phenylamino)-methyl]-2-methylsulfanyl-pyrimidin-4-ylamine A mixture of 4-Amino-2-methylsulfanyl-pyrimidine-5-carbaldehyde (2.45 g, 14.5 mmol), 2,6-difluoro-3,5-dimethoxyaniline (2.75 g, 14.5 mmol), and camphorsulfonic acid (1.01 g, 4.35 mmol) in toluene (80 mL) was heated at reflux for 18 hours (note: the flask was equipped with a Dean-Stark trap). The solvent was removed under reduced pressure to afford a yellow solid. The crude product was sufficiently pure, so it was taken on to the next step. To a suspension of the crude imine (~4.93 g) in tetrahydrofuran (60 mL) at 0° C., lithium aluminum hydride (820 mg, 21.6 mmol) was added in several portions. Caution, gas evolution! The resulting yellow suspension was then stirred at 0° C. for 1 hour, whereupon a green solution was afforded. Water (1 mL), 15% aqueous sodium hydroxide (1 mL), and water (3 mL) were added sequentially. Care is advised during this quenching protocol. The resulting mixture was then stirred at 0° C. for 10 minutes. The suspension was then filtered over a pad of Celite, and the Celite was rinsed with dichloromethane. The combined filtrates were concentrated under reduced to give a thick oil. Recrystallization was accomplished with a solvent mixture of dichloro-methane:hexanes:methanol (17:8.5:1, 312 mL) to give 1.85 g of the desired aniline. The mother liquor was concentrated and recrystallized with the same solvent mixture to give an additional 0.48 g of product. The second mother liquor was concentrated and recrystallized to afford 0.84 g. The precipitates were combined to give 3.17 g (64%, for 2 steps) of the title compound: MS (APCI) 343.1, 344.1.

b) 3-(2,6-Difluoro-3,5-dimethoxy-phenyl)-7-methylsulfanyl-3,4-dihydro-1H-pyrimido[4,5-d]pyrimidin-2-one To a 0° C. suspension of sodium hydride [861 mg (1.44 g of 60%), 35.9 mmol] in dimethylformamide (20 mL) was added 5-[2,6-Difluoro-3,5-dimethoxy-phenylamino)-methyl]-2-methylsulfanyl-pyrimidin-4-ylamine (3.07 g, 8.97 mmol) in dimethyl-formamide (24 mL). The resulting heterogeneous mixture was stirred at 0° C. for 5 minutes and then at room temperature for 90 minutes. The mixture was cooled to 0° C. and carbonyldiimidazole (5.09 g, 31.4 mmol) in dimethylformamide (15 mL) was added cautiously (gas evolution!). The resulting orange solution was stirred at room temperature for 3 days. Saturated aqueous ammonium chloride (10 mL) was added to the orange solution at 0° C., and the mixture was concentrated under reduced pressure. The suspension thus afforded was partitioned between dichloromethane (250 mL) and saturated ammonium chloride (50 mL). The layers were separated; the organic layer was washed with water (3×50 mL), dried (magnesium sulfate), filtered, and concentrated under reduced pressure to give a yellow solid. The solid was then triturated with a mixture of diethyl ether:dichloromethane (4:1, 50 mL) and then filtered to afford 2.35 g (71%) of title compound as an off-white solid: MS (APCI) 369.0, 370.1.

c) Ethyl-4-[3-(2,6-difluoro-3,5-dimethoxy-phenyl)-7-methylsulfanyl-2-oxo-3,4-dihydro-2H-pyrimido[4,5-d]pyrimidin-1-yl]-cyclohexanecarboxylate To a 250-mL dry, round-bottomed flask was added 3-(2,6-Difluoro-3,5-dimethoxy-phenyl)-7-methylsulfanyl-2-oxo-3,4-dihydro-2H-pyrimido[4,5-d]pyrimidine (1.5 g, 4.08 mmol), ethyl-4-hydroxycyclohexanecarboxylate (2.11 g, 12.23 mmol), triphenylphosphine (3.21 g, 12.23 mmol), and tetrahydrofuran (50 mL), and the solution was blanketed with a nitrogen atmosphere. The solution was then cooled to 0° C., and diisopropylazodicarboxylate (2.41 mL, 12.23 mmol) was added dropwise. The solution was then warmed to room temperature and stirred overnight. The crude mixture was then concentrated in vacuo and taken up in dichloromethane, washed with water, dried over sodium sulfate, and concentrated. The crude was purified by flash silica chromatography eluting with 3:2 hexane/ethyl acetate to yield the title compound (1.17 g, 55% yield): LRMS: 523.2 (M+H).

d) Ethyl-4-[3-(2,6-difluoro-3,5-dimethoxy-phenyl)-7-methylsulfinyl-2-oxo-3,4-dihydro-2H-pyrimido[4,5-d]pyrimidin-1-yl]-cyclohexanecarboxylate To a solution of Ethyl-4-[3-(2,6-difluoro-3,5-dimethoxy-phenyl)-7-methylsulfanyl-2-oxo-3,4-dihydro-2H-pyrimido[4,5-d]pyrimidin-1-yl]-cyclohexanecarboxylate (1.17 g, 2.24 mmol) in chloroform (15 mL) was added trans-2-(phenylsulfonyl)-3-phenyloxaziridine (644 mg, 2.47 mmol). The solution was stirred at room temperature for 16 hrs, then concentrated in vacuo. The crude material was purified by flash silica chromatography eluting with 9:1 ethyl acetate/ethanol to give title compound (820 mg, 68% yield): LRMS: 539.1 (M+1).

e) Ethyl-4-[3-(2,6-difluoro-3,5-dimethoxy-phenyl)-7-methylamino-2-oxo-3,4-dihydro-2H-pyrimido[4,5-d]pyrimidin-1-yl]-cyclohexanecarboxylate To a 100-mL round-bottomed flask was added Ethyl-4-[3-(2,6-difluoro-3,5-dimethoxy-phenyl)-7-methylsulfinyl-2-oxo-3,4-dihydro-2H-pyrimido[4,5-d]pyrimidin-1-yl]-cyclohexanecarboxylate (820 mg, 1.52 mmol), dioxane(60 mL), then a 2 M solution of methylamine in tetrahydrofuran (7.6 mL, 15.2 mmol), and the solution was heated to 60° C. under an atmosphere of nitrogen for 5 hours. The solution was then concentrated in vacuo, and reacted further without purification: LRMS: 506.2 (M+H).

EXAMPLE 23

4-[3-(2,6-Difluoro-3,5-dimethoxy-phenyl)-7-methylamino-2-oxo-3,4-dihydro-2H-pyrimido[4,5-d]pyrimidin-1-yl]-cyclohexanecarboxylic Acid To a 250-mL round-bottomed flask was added Ethyl-4-[3-(2,6-difluoro-3,5-dimethoxy-phenyl)-7-methylamino-2-oxo-3,4-dihydro-2H-pyrimido[4,5-d]pyrimidin-1-yl]-cyclohexanecarboxylate (crude 1.5 mmol), methanol (70 mL), water (20 mL), and sodium hydroxide (600 mg, 15 mmol), and the mixture was heated to 50° C. for 3 days. The crude reaction solution was then concentrated to less than 10 mL in vacuo, and then the volume was increased to 50 mL with water. The pH was then adjusted to 4 with 6 M hydrochloric acid, and the resulting white precipitate was collected by filtration and dried in vacuo overnight to deliver the title compound (460 mg, 63% yield for 2 steps) as a white solid: mp 148° C., LRMS: 478.2 (M+H).

EXAMPLE 24

7-Amino-3-(2,6-difluoro-3,5-dimethoxy-phenyl)-1-piperidin-4-yl-3,4-dihydro-1H-pyrimido[4,5-d]pyrimidin-2-one; compound with trifluoroacetic acid The title compound was prepared as follows:

a) 4-[3-(2,6-Difluoro-3,5-dimethoxy-phenyl)-7-methylsulfinyl-2-oxo-3,4-dihydro-2H-pyrimido[4,5-d]pyrimidin-1-yl]-piperidine-1-carboxylic acid tert-butyl este To a suspension of 3-(2,6-Difluoro-3,5-dimethoxy-phenyl)-7-methylsulfanyl-3,4-dihydro-1H-pyrimido[4,5-d]pyrimidin-2-one (2.24 g, 6.08 mmol), tert-Butyl-4-hydroxy-1-piperidinecarboxylate (3.66 g, 18.2 mmol), and triphenylphosphine (4.77 g, 18,2 mmol) in tetrahydrofuran (50 mL) at 0° C., diethyl azodicarboxylate (3.17 g, 18.2 mmol) was added dropwise. The resulting yellow suspension was then stirred at room temperature. Within 1 hour a yellow solution was afforded which was stirred at room temperature for 40 hours. The solvent was removed under reduced pressure to give a thick yellow oil (8.96 g). Attempts to purify the desired product from triphenylphosphine oxide and the reduced diethyl azodicarboxylate reagent failed, so the crude product was taken to the next step [note: by $^1$H NMR the thick oil consisted of reduced diethyl azodicarboxylate:triphenylphosphine oxide:desired Mitsunobu product (3.2:2.58:1)]. The crude product (~2.73 g, based on $^1$H NMR integration) was dissolved in chloroform (65 mL), and the solution thus afforded was cooled to 0° C., and Davis' oxaziridine (1.55 g, 5.94 mmol) was added in several portions. The solution was then stirred at room temperature for 20 hours; mass spec showed starting material, so an additional portion of the oxaziridine (430 mg) was added, and stirring of the reaction continued for 4 additional hours. The solution was concentrated under reduced pressure to a volume of ~15 mL. The sample was then purified using flash chromatography eluting with ethyl acetate and then dichloromethane/methanol (40:1). 2.93 g of a white solid were afforded. By $^1$H NMR the solid was a mixture of desired product/reduced diethyl azodicarboxylate/triphenylphosphine oxide(14:2.9: 1). The solid was repurified using flash chromatography method first eluting with ethyl acetate and then dichloromethane/methanol (50: 1) to afford 2.02 g (59% for two steps) of the title compound as a white foam: MS (APCI) 468.2, 469.2.

b) 4-[7-Amino-3-(2,6-difluoro-3,5-dimethoxy-phenyl)-2-oxo-3,4-dihydro-2H-pyrimido[4,5-d]pyrimidin-1-yl]-piperidine-1-carboxylic acid tert-butyl ester 4-[3-(2,6-Difluoro-3,5-dimethoxy-phenyl)-7-methylsulfinyl-2-oxo-3,4-dihydro-2H-pyrimido[4,5-d]pyrimidin-1-yl]-piperidine-1-carboxylic acid tert-butyl ester (419 mg, 0.738 mmol) and liquid ammonia (20 mL) in dioxane (20 mL) were stirred in a sealed tube at room temperature for 24 hours. The solvent was removed under reduced pressure. The resulting residue was purified via flash chromatography eluting with a gradient of ethyl acetate:hexanes (2:1 to 5:1) to give 312 mg (81%) of the title compound: MS (APCI) 421.1, 465.2, 521.2.

c) 7-Amino-3-(2,6-difluoro-3,5-dimethoxy-phenyl)-1-piperidin-4-yl-3,4-dihydro-1H-pyrimido[4,5-d]pyrimidin-2-one; compound with trifluoroacetic acid To a solution of 4-[7-Amino-3-(2,6-difluoro-3,5-dimethoxy-phenyl)-2-oxo-3,4-dihydro-2H-pyrimido[4,5-d]pyrimidin-1-yl]-piperidine-1-carboxylic acid tert-butyl ester (295 mg, 0.567 mmol) in dichloromethane (5 mL) at 0° C. trifluoroacetic acid (647 μL) was added. The resulting solution was stirred at room temperature for 5 hours. The solution was then concentrated under reduced pressure. The resulting residue was concentrated with toluene (2×50 mL) to give a thick oil. Dichloromethane (2 mL) was added to the oil to produce a white precipitate. To accelerate precipitation diethyl ether (10 mL) was added. The mixture was then filtered to deliver 338 mg (92%) of the title compound as a white powder: mp 200° C.–220° C. (decomposition); MS (APCI) 421.1, 422.2.

EXAMPLE 25

1-Cyclopentyl-3-(2-fluoro-3,5-dimethoxy-phenyl)-7-(2-hydroxy-1-hydroxymethyl-ethylamino)-3,4-dihydro-1H-pyrimido[4,5-d]pyrimidin-2-one 1-Cyclopentyl-3-(2-fluoro-3,5-dimethoxy-phenyl)-7-(2-hydroxy-1-hydroxymethyl-ethylamino)-3,4-dihydro-1H-pyrimido[4,5-d]pyrimidin-2-one was prepared as in Example 2 using 0.4 g (0.92 mmol) 1-cyclopentyl-3-(2-fluoro-3,5-dimethoxy-phenyl)-7-methanesulfinyl-3,4-dihydro-1H-pyrimido[4,5-d]pyrimidin-2-one and 0.25 g (2.76 mmol) serinol. The final product was purified by column chromatography (20:1 dichloromethane/methanol). This gave 0.29 g (68%) of 1-cyclopentyl-3-(2-fluoro-3,5-dimethoxy-phenyl)-7-(2-hydroxy-1-hydroxymethyl-ethylamino)-3,4-dihydro-1H-pyrimido[4,5-d]pyrimidin-2-one as a white solid: mp 194° C.–195° C.; MS (APCI) m/z 462.2, 463.2.

EXAMPLE 26

1-Ethyl-3-(2-fluoro-3,5-dimethoxy-phenyl)-7-(4-hydroxy-butylamino)-3,4-dihydro-1H-pyrimido[4,5-d]pyrimidin-2-one 1-Ethyl-3-(2-fluoro-3,5-dimethoxy-phenyl)-7-(4-hydroxy-butylamino)-3,4-dihydro-1H-pyrimido[4,5-d]pyrimidin-2-one was prepared as in Example 2 using 0.4 g (1.01 mmol) 1-ethyl-3-(2-fluoro-3,5-dimethoxy-phenyl)-7-methanesulfinyl-3,4-dihydro-1H-pyrimido[4,5-d]pyrimidin-2-one and 0.27 g (3.03 mmol) 4-amino-butan-1-ol. The final product was purified by column chromatography (20:1 dichloromethane/methanol). This gave 0.375 g (88%) of 1-ethyl-3-(2-fluoro-3,5-dimethoxy-phenyl)-7-(4-hydroxy-butylamino)-3,4-dihydro-1H-pyrimido[4,5-d]pyrimidin-2-one as a white solid: mp 129° C.–131° C.; MS (APCI) m+1/z 420.

EXAMPLE 27

(S)-1-Cyclopentyl-7-(2,3-dihydroxy-propylamino)-3-(2-fluoro-3,5-dimethoxy-phenyl)-3,4-dihydro-1H-pyrimido[4,5-d]pyrimidin-2-one (S)-1-Cyclopentyl-7-(2,3-dihydroxy-propylamino)-3-(2-fluoro-3,5-dimethoxy-phenyl)-3,4-dihydro-1H-pyrimido[4,5-d]pyrimidin-2-one was prepared as in Example 2 using 0.4 g (0.92 mmol) 1-cyclopentyl-3-(2-fluoro-3,5-dimethoxy-phenyl)-7-methanesulfinyl-3,4-dihydro-1H-pyrimido[4,5-d]pyrimidin-2-one and 0.252 g (2.76 mmol) (S)-3-amino-1,2-propanediol. This gave 0.268 g (63%) of (S)-1-cyclopentyl-7-(2,3-dihydroxy-propylamino)-3-(2-fluoro-3,5-dimethoxy-phenyl)-3,4-dihydro-1H-pyrimido[4,5-d]pyrimidin-2-one as a white solid: mp 92° C.–94° C.; MS (APCI) m/z 462.2, 463.2.

EXAMPLE 28

1-Ethyl-3-(2-fluoro-3,5-dimethoxy-phenyl)-7-(4-hydroxy-cyclohexylamino)-3,4-dihydro-1H-pyrimido[4,5-d]pyrimidin-2-one A flask was charged with 0.312 g (0.79 mmol) of 1-Ethyl-3-(2-fluoro-3,5-dimethoxy-phenyl)-7-methanesulfinyl-3,4-dihydro-1H-pyrimido[4,5-d]pyrimidin-2-one, 15 mL dioxane, and 0.273 g (2.37 mmol) of trans-4-

Aminocyclohexanol, and the mixture was heated 48 hours at 95° C. The dioxane was removed under reduced pressure, and the crude residue was purified directly via column chromatography (20:1 dichloromethane/methanol). This procedure gave 0.215 g (66%) of 1-Ethyl-3-(2-fluoro-3,5-dimethoxy-phenyl)-7-(4-hydroxy-cyclohexylamino)-3,4-dihydro-1H-pyrimido[4,5-d]pyrimidin-2-one as a white solid: mp=198° C.–204° C.; MS (APCI) m+1/z 462.

EXAMPLE 29

4-[3-(2,6-Difluoro-3,5-dimethoxy-phenyl)-7-methylamino-2-oxo-3,4-dihydro-2H-pyrimido[4,5-d]pyrimidin-1-yl]-piperidine-1-carboxylic acid tert-butyl ester 4-[3-(2,6-Difluoro-3,5-dimethoxy-phenyl)-7-methylamino-2-oxo-3,4-dihydro-2H-pyrimido[4,5-d]pyrimidin-1-yl]-piperidine-1-carboxylic acid tert-butyl ester was synthesized in a same manner as 4-[3-(2,6-dichloro-3,5-dimethoxy-phenyl)-7-methylamino-2-oxo-3,4-dihydro-2H-pyrimido[4,5-d]pyrimidin-1-yl]-piperidine-1-carboxylic/ acid tert-butyl ester. However, 4-[3-(2,6-difluoro-3,5-dimethoxy-phenyl)-7-methansulfinyl-2-oxo-3,4-dihydro-2H-pyrimido[4,5-d]pyrimidin-1-yl-piperidine-1-carboxylic acid tert-butyl ester (535 mg, 0.943 mmol) and 40% aqueous methylamine (407 µL, 4.72 mmol) were used to afford the title compound (442 mg, 88%) as a white solid: MS (APCI) 435.1, 479.1, 535.2.

EXAMPLE 30

3-(2,6-Difluoro-3,5-dimethoxy-phenyl)-7-methylamino-1-piperidin-4-yl-3,4-dihydro-1H-pyrimido[4,5-d]pyrimidin-2-one; compound with trifluoroacetic acid 3-(2,6-Difluoro-3,5-dimethoxy-phenyl)-7-methylamino-1-piperidin-4-yl-3,4-dihydro-1H-pyrimido[4,5-d]pyrimidin-2-one; compound with trifluoroacetic acid was synthesized in the same manner as 3-(2,6-dichloro-3,5-dimethoxy-phenyl)-7-methylamino-1-piperidin-4-yl-3,4-dihydro-1H-pyrimido[4,5-d]pyrimidin-2-one, compound with trifluoroacetic acid; however, 4-[3-(2,6-difluoro-3,5-dimethoxy-phenyl)-7-methylamino-2-oxo-3,4-dihydro-2H-pyrimido[4,5-d]pyrimidin-1-yl]-piperidine-1-carboxylic acid tert-butyl ester (411 mg, 0.187 mmol) and trifluoroacetic acid (878 µL) were used to deliver the title compound (482 mg) as a white solid: HPLC=88% pure; mp 135° C.–140° C.; MS (APCI) 435.1, 436.1.

EXAMPLE 31

3-(2,6-Difluoro-3,5-dimethoxy-phenyl)-7-(2,3-dihydroxy-propylamino)-1-ethyl-3,4-dihydro-1H-pyrimido[4,5-d]pyrimidin-2-one 3-(2,6-Difluoro-3,5-dimethoxy-phenyl)-7-(2,3-dihydroxy-propylamino)-1-ethyl-3,4-dihydro-1H-pyrimido[4,5-d]pyrimidin-2-one was prepared as described in Example 7 using 0.48 g (1.16 mmol) of 3-(2,6-difluoro-3,5-dimethoxy-phenyl)-1-ethyl-7-methylsulfinyl-3,4-dihydro-1H-pyrimido[4,5-d]pyrimidin-2-one and 0.32 g (3.49 mmol) of R-(+)-3-amino-1,2-propanediol. The crude product was purified by medium-pressure chromatography eluting with 20:1 dichloromethane/methanol to give 0.346 g (68%) of title compound: mp 148° C.–152° C. MS (APCI) (m+1)/z 440.1.

EXAMPLE 32

1-Cyclopentyl-7-(4-diethylamino-butylamino)-3-(3-ethoxy-2,6-difluoro-phenyl)-3,4-dihydro-1H-pyrimido[4,5-d]pyrimidin-2-one Using Procedure K, described above, 0.74 g (1.69 mmol) of 3-(3-ethoxy-2,6-difluoro-phenyl)-1-(1-ethyl-propyl)-7-methanesulfinyl-3,4-dihydro-1H-pyrimido[4,5-d]pyrimidin-2-one and 4-(diethylamino)butylamine in 20 mL of dioxane were reacted. Chromatography with 9:1:0.5 ethyl acetate/ethanol/ triethylamine gave 0.75 g (86%) of the title compound as a solid: mp 129° C.–130° C. 130° C. MS (APCI) (m+1)/z 5127.47. Analysis calculated for $C_{27}H_{38}N_6F_2O_2$: C, 62.77; H, 7.41; N, 16.27.Found: C, 62.79; H, 7.35; N, 16.10.

EXAMPLE 33

(R)-1-Cyclopentyl-7-(2,3-dihydroxy-propylamino)-3-(2-fluoro-3,5-dimethoxy-phenyl)-3,4-dihydro-1H-pyrimido[4,5-d]pyrimidin-2-one R)-1-Cyclopentyl-7-(2,3-dihydroxy-propylamino)-3-(2-fluoro-3,5-dimethoxy-phenyl)-3,4-dihydro-1H-pyrimido[4,5-d]pyrimidin-2-one was prepared as in Example 2 using 0.4 g (0.92 mmol) 1-cyclopentyl-3-(2-fluoro-3,5-dimethoxy-phenyl)-7-methanesulfinyl-3,4-dihydro-1H-pyrimido[4,5-d]pyrimidin-2-one and 0.252 g (2.76 mmol) (R)-3-amino-1, 2-propanediol. The final product was purified by column chromatography (20:1 dichloromethane/methanol). This gave 0.290 g (68%) of (R)-1-cyclopentyl-7-(2,3-dihydroxy-propylamino)-3-(2-fluoro-3,5-dimethoxy-phenyl)-3,4-dihydro-1H-pyrimido[4,5-d]pyrimidin-2-one as a white solid: mp 89° C.–91° C.; MS (APCI) m/z 462.2, 463.2.

EXAMPLE 34

1-Ethyl-3-(2-fluoro-3,5-dimethoxy-phenyl)-7-[2-(2-hydroxy-ethoxy)-ethylamino]-3,4-dihydro-1H-pyrimido[4,5-d]pyrimidin-2-one 1-Ethyl-3-(2-fluoro-3,5-dimethoxy-phenyl)-7-[2-(2-hydroxy-ethoxy)-ethylamino]-3,4-dihydro-1H-pyrimido[4,5-d]pyrimidin-2-one was prepared as in Example 2 using 0.350 g (0.887 mmol) 1-ethyl-3-(2-fluoro-3,5-dimethoxy-phenyl)-7-methanesulfinyl-3,4-dihydro-1H-pyrimido[4,5-d]pyrimidin-2-one and 0.267 mL (2.66 mmol) 2-(2-amino-ethoxy)-ethanol. The final product was purified by column chromatography (20:1 dichloromethane/methanol). This gave 0.331 g (86%) of 1-ethyl-3-(2-fluoro-3,5-dimethoxy-phenyl)-7-[2-(2-hydroxy-ethoxy)-ethylamino]-3,4-dihydro-1H-pyrimido[4,5-d]pyrimidin-2-one as a white solid: mp 143° C.–146° C.; MS (APCI) m+1/z 436.

EXAMPLE 35

1-Cyclopentyl-3-(2-fluoro-3,5-dimethoxy-phenyl)-7-(trans-4-hydroxy-cyclohexylamino)-3,4-dihydro-1H-pyrimido[4,5-d]pyrimidin-2-one 1-Cyclopentyl-3-(2-fluoro-3,5-dimethoxy-phenyl)-7-(trans-4-hydroxy-cyclohexylamino)-3,4-dihydro-1H-pyrimido[4,5-d]pyrimidin-2-one was prepared as in Example 2 using 0.5 g (1.15 mmol) 1-cyclopentyl-3-(2-fluoro-3,5-dimethoxy-phenyl)-7-methanesulfinyl-3,4-dihydro-1H-pyrimido[4,5-d]pyrimidin-2-one and 0.389 g (3.45 mmol)

trans-4-hydroxy-cyclohexylamine. The final product was purified by column chromatography (20:1 dichloromethane/methanol). This gave 0.320 g (57%) of 1-cyclopentyl-3-(2-fluoro-3,5-dimethoxy-phenyl)-7-(trans-4-hydroxy-cyclohexylamino)-3,4-dihydro-1H-pyrimido[4,5-d]pyrimidin-2-one as a white solid: mp 108° C.–110° C.; MS (APCI) m/z 486.2, 487.2.

Additional non-limiting examples of pyrimido[4,5-d]pyrimidin-2-one compounds within the scope of this invention include:

1-Cyclopentyl-7-(4-diethylamino-butylamino)-3-(2,6-difluoro-3-hydroxy-5-methoxy phenyl)-3,4-dihydro-1H-pyrimido[4,5-d]pyrimidin-2-one;

1-Cyclopentyl-7-(4-diethylamino-butylamino)-3-(2,6-difluoro-3,5-dimethoxy phenyl)-3,4-dihydro-1H-pyrimido[4,5-d]pyrimidin-2-one;

1-Cyclopentyl-7-(4-diethylamino-butylamino)-3-(2,6-difluoro-3-methoxy-5-ethoxy phenyl)-3,4-dihydro-1H-pyrimido[4,5-d]pyrimidin-2-one;

1-Cyclopentyl-7-(4-diethylamino-butylamino)-3-(2,6-difluoro-3-hydroxy-5-ethoxy phenyl)-3,4-dihydro-1H-pyrimido[4,5-d]pyrimidin-2-one;

1-Cyclopentyl-7-(4-diethylamino-butylamino)-3-(2,6-difluoro-3-methoxy-phenyl)-3,4-dihydro-1H-pyrimido[4,5-d]pyrimidin-2-one;

1-Cyclopentyl-7-(4-diethylamino-butylamino)-3-(2,6-difluoro-3-ethoxy-phenyl)-3,4-dihydro-1H-pyrimido[4,5-d]pyrimidin-2-one;

1-Cyclopentyl-7-(4-diethylamino-butylamino)-3-(2,6-difluoro-3-hydroxy-phenyl)-3,4-dihydro-1H-pyrimido[4,5-d]pyrimidin-2-one;

1-Cyclopropyl-7-(4-diethylamino-butylamino)-3-(2,6-difluoro-3-hydroxy-5-methoxy phenyl)-3,4-dihydro-1H-pyrimido[4,5-d]pyrimidin-2-one;

1-Cyclopropyl-7-(4-diethylamino-butylamino)-3-(2,6-difluoro-3,5-dimethoxy phenyl)-3,4-dihydro-1H-pyrimido[4,5-d]pyrimidin-2-one;

1-Cyclopropyl-7-(4-diethylamino-butylamino)-3-(2,6-difluoro-3-methoxy-5-ethoxy phenyl)-3,4-dihydro-1H-pyrimido[4,5-d]pyrimidin-2-one;

1-Cyclopropyl-7-(4-diethylamino-butylamino)-3-(2,6-difluoro-3-hydroxy-5-ethoxy phenyl)-3,4-dihydro-1H-pyrimido[4,5-d]pyrimidin-2-one;

1-Cyclopropyl-7-(4-diethylamino-butylamino)-3-(2,6-difluoro-3-methoxy-phenyl)-3,4-dihydro-1H-pyrimido[4,5-d]pyrimidin-2-one;

1-Cyclopropyl-7-(4-diethylamino-butylamino)-3-(2,6-difluoro-3-ethoxy-phenyl)-3,4-dihydro-1H-pyrimido[4,5-d]pyrimidin-2-one;

1-Cyclopropyl-7-(4-diethylamino-butylamino)-3-(2,6-difluoro-3-hydroxy-phenyl)-3,4-dihydro-1H-pyrimido[4,5-d]pyrimidin-2-one;

1-Ethyl-7-(4-diethylamino-butylamino)-3-(2,6-difluoro-3-hydroxy-5-methoxy phenyl)-3,4-dihydro-1H-pyrimido[4,5-d]pyrimidin-2-one;

1-Ethyl-7-(4-diethylamino-butylamino)-3-(2,6-difluoro-3,5-dimethoxy phenyl)-3,4-dihydro-1H-pyrimido[4,5-d]pyrimidin-2-one;

1-Ethyl-7-(4-diethylamino-butylamino)-3-(2,6-difluoro-3-methoxy-5-ethoxy phenyl)-3,4-dihydro-1H-pyrimido[4,5-d]pyrimidin-2-one;

1-Ethyl-7-(4-diethylamino-butylamino)-3-(2,6-difluoro-3-hydroxy-5-ethoxy phenyl)-3,4-dihydro-1H-pyrimido[4,5-d]pyrimidin-2-one;

1-Ethyl-7-(4-diethylamino-butylamino)-3-(2,6-difluoro-3-methoxy-phenyl)-3,4-dihydro-1H-pyrimido[4,5-d]pyrimidin-2-one;

1-Ethyl-7-(4-diethylamino-butylamino)-3-(2,6-difluoro-3-ethoxy-phenyl)-3,4-dihydro-1H-pyrimido[4,5-d]pyrimidin-2-one;

1-Ethyl-7-(4-diethylamino-butylamino)-3-(2,6-difluoro-3-hydroxy-phenyl)-3,4-dihydro-1H-pyrimido[4,5-d]pyrimidin-2-one;

1-Cyclopentyl-7-(4-diethylamino-butylamino)-3-(2-fluoro-3-hydroxy-5-methoxy phenyl)-3,4-dihydro-1H-pyrimido[4,5-d]pyrimidin-2-one;

1-Cyclopentyl-7-(4-diethylamino-butylamino)-3-(2-fluoro-3,5-dimethoxy phenyl)-3,4-dihydro-1H-pyrimido[4,5-d]pyrimidin-2-one;

1-Cyclopentyl-7-(4-diethylamino-butylamino)-3-(2-fluoro-3-methoxy-5-ethoxy phenyl)-3,4-dihydro-1H-pyrimido[4,5-d]pyrimidin-2-one;

1-Cyclopentyl-7-(4-diethylamino-butylamino)-3-(2-fluoro-3-hydroxy-5-ethoxy phenyl)-3,4-dihydro-1H-pyrimido[4,5-d]pyrimidin-2-one;

1-Cyclopentyl-7-(4-diethylamino-butylamino)-3-(2-fluoro-3-methoxy-phenyl)-3,4-dihydro-1H-pyrimido[4,5-d]pyrimidin-2-one;

1-Cyclopentyl-7-(4-diethylamino-butylamino)-3-(2-fluoro-3-ethoxy-phenyl)-3,4-dihydro-1H-pyrimido[4,5-d]pyrimidin-2-one;

1-Cyclopentyl-7-(4-diethylamino-butylamino)-3-(2-difluoro-3-hydroxy-phenyl)-3,4-dihydro-1H-pyrimido[4,5-d]pyrimidin-2-one;

1-Cyclopropyl-7-(4-diethylamino-butylamino)-3-(2-fluoro-3-hydroxy-5-methoxy phenyl)-3,4-dihydro-1H-pyrimido[4,5-d]pyrimidin-2-one;

1-Cyclopropyl-7-(4-diethylamino-butylamino)-3-(2-fluoro-3,5-dimethoxy phenyl)-3,4-dihydro-1H-pyrimido[4,5-d]pyrimidin-2-one;

1-Cyclopropyl-7-(4-diethylamino-butylamino)-3-(2-fluoro-3-methoxy-5-ethoxy phenyl)-3,4-dihydro-1H-pyrimido[4,5-d]pyrimidin-2-one;

1-Cyclopropyl-7-(4-diethylamino-butylamino)-3-(2-fluoro-3-hydroxy-5-ethoxy phenyl)-3,4-dihydro-1H-pyrimido[4,5-d]pyrimidin-2-one;

1-Cyclopropyl-7-(4-diethylamino-butylamino)-3-(2-fluoro-3-methoxy-phenyl)-3,4-dihydro-1H-pyrimido[4,5-d]pyrimidin-2-one;

1-Cyclopropyl-7-(4-diethylamino-butylamino)-3-(2-fluoro-3-ethoxy-phenyl)-3,4-dihydro-1H-pyrimido[4,5-d]pyrimidin-2-one;

1-Cyclopropyl-7-(4-diethylamino-butylamino)-3-(2-difluoro-3-hydroxy-phenyl)-3,4-dihydro-1H-pyrimido[4,5-d]pyrimidin-2-one;

1-Ethyl-7-(4-diethylamino-butylamino)-3-(2-fluoro-3-hydroxy-5-methoxy phenyl)-3,4-dihydro-1H-pyrimido[4,5-d]pyrimidin-2-one;

1-Ethyl-7-(4-diethylamino-butylamino)-3-(2-fluoro-3,5-dimethoxy phenyl)-3,4-dihydro-1H-pyrimido[4,5-d]pyrimidin-2-one;

1-Ethyl-7-(4-diethylamino-butylamino)-3-(2-fluoro-3-methoxy-5-ethoxy phenyl)-3,4-dihydro-1H-pyrimido[4,5-d]pyrimidin-2-one;

1-Ethyl-7-(4-diethylamino-butylamino)-3-(2-fluoro-3-hydroxy-5-ethoxy phenyl)-3,4-dihydro-1H-pyrimido[4,5-d]pyrimidin-2-one;

1-Ethyl-7-(4-diethylamino-butylamino)-3-(2-fluoro-3-methoxy-phenyl)-3,4-dihydro-1H-pyrimido[4,5-d]pyrimidin-2-one;

1-Ethyl-7-(4-diethylamino-butylamino)-3-(2-fluoro-3-ethoxy-phenyl)-3,4-dihydro-1H-pyrimido[4,5-d]pyrimidin-2-one;

1-Ethyl-7-(4-diethylamino-butylamino)-3-(2-difluoro-3-hydroxy-phenyl)-3,4-dihydro-1H-pyrimido[4,5-d]pyrimidin-2-one;

1-Cyclopentyl-7-(4-diethylamino-butylamino)-3-(2-fluoro-6-chloro-3-hydroxy-5-methoxy phenyl)-3,4-dihydro-1H-pyrimido[4,5-d]pyrimidin-2-one;

1-Cyclopentyl-7-(4-diethylamino-butylamino)-3-(2-fluoro-6-chloro-3,5-dimethoxy phenyl)-3,4-dihydro-1H-pyrimido[4,5-d]pyrimidin-2-one;

1-Cyclopentyl-7-(4-diethylamino-butylamino)-3-(2-fluoro-6-chloro-3-methoxy-5-ethoxy phenyl)-3,4-dihydro-1H-pyrimido[4,5-d]pyrimidin-2-one;

1-Cyclopentyl-7-(4-diethylamino-butylamino)-3-(2-fluoro-6-chloro-3-hydroxy-5-ethoxy phenyl)-3,4-dihydro-1H-pyrimido[4,5-d]pyrimidin-2-one;

1-Cyclopentyl-7-(4-diethylamino-butylamino)-3-(2-fluoro-6-chloro-3-methoxy-phenyl)-3,4-dihydro-1H-pyrimido[4,5-d]pyrimidin-2-one;

1-Cyclopentyl-7-(4-diethylamino-butylamino)-3-(2-fluoro-6-chloro-3-ethoxy-phenyl)-3,4-dihydro-1H-pyrimido[4,5-d]pyrimidin-2-one;

1-Cyclopentyl-7-(4-diethylamino-butylamino)-3-(2-difluoro-6-chloro-3-hydroxy-phenyl)-3,4-dihydro-1H-pyrimido[4,5-d]pyrimidin-2-one;

1-Cyclopropyl-7-(4-diethylamino-butylamino)-3-(2-fluoro-6-chloro-3-hydroxy-5-methoxy phenyl)-3,4-dihydro-1H-pyrimido[4,5-d]pyrimidin-2-one;

1-Cyclopropyl-7-(4-diethylamino-butylamino)-3-(2-fluoro-6-chloro-3,5-dimethoxy phenyl)-3,4-dihydro-1H-pyrimido[4,5-d]pyrimidin-2-one;

1-Cyclopropyl-7-(4-diethylamino-butylamino)-3-(2-fluoro-6-chloro-3-methoxy-5-ethoxy phenyl)-3,4-dihydro-1H-pyrimido[4,5-d]pyrimidin-2-one;

1-Cyclopropyl-7-(4-diethylamino-butylamino)-3-(2-fluoro-6-chloro-3-hydroxy-5-ethoxy phenyl)-3,4-dihydro-1H-pyrimido[4,5-d]pyrimidin-2-one;

1-Cyclopropyl-7-(4-diethylamino-butylamino)-3-(2-fluoro-6-chloro-3-methoxy-phenyl)-3,4-dihydro-1H-pyrimido[4,5-d]pyrimidin-2-one;

1-Cyclopropyl-7-(4-diethylamino-butylamino)-3-(2-fluoro-6-chloro-3-ethoxy-phenyl)-3,4-dihydro-1H-pyrimido[4,5-d]pyrimidin-2-one;

1-Cyclopropyl-7-(4-diethylamino-butylamino)-3-(2-difluoro-6-chloro-3-hydroxy-phenyl)-3,4-dihydro-1H-pyrimido[4,5-d]pyrimidin-2-one;

1-Ethyl-7-(4-diethylamino-butylamino)-3-(2-fluoro-6-chloro-3-hydroxy-5-methoxy phenyl)-3,4-dihydro-1H-pyrimido[4,5-d]pyrimidin-2-one;

1-Ethyl-7-(4-diethylamino-butylamino)-3-(2-fluoro-6-chloro-3,5-dimethoxy phenyl)-3,4-dihydro-1H-pyrimido[4,5-d]pyrimidin-2-one;

1-Ethyl-7-(4-diethylamino-butylamino)-3-(2-fluoro-6-chloro-3-methoxy-5-ethoxy phenyl)-3,4-dihydro-1H-pyrimido[4,5-d]pyrimidin-2-one;

1-Ethyl-7-(4-diethylamino-butylamino)-3-(2-fluoro-6-chloro-3-hydroxy-5-ethoxy phenyl)-3,4-dihydro-1H-pyrimido[4,5-d]pyrimidin-2-one;

1-Ethyl-7-(4-diethylamino-butylamino)-3-(2-fluoro-6-chloro-3-methoxy-phenyl)-3,4-dihydro-1H-pyrimido[4,5-d]pyrimidin-2-one;

1-Ethyl-7-(4-diethylamino-butylamino)-3-(2-fluoro-6-chloro-3-ethoxy-phenyl)-3,4-dihydro-1H-pyrimido[4,5-d]pyrimidin-2-one;

1-Ethyl-7-(4-diethylamino-butylamino)-3-(2-difluoro-6-chloro-3-hydroxy-phenyl)-3,4-dihydro-1H-pyrimido[4,5-d]pyrimidin-2-one;

1-Cyclopentyl-7-(4-hydroxy-cyclohexylamino)-3-(2,6-difluoro-3-hydroxy-5-methoxy phenyl)-3,4-dihydro-1H-pyrimido[4,5-d]pyrimidin-2-one;

1-Cyclopentyl-7-(4-hydroxy-cyclohexylamino)-3-(2,6-difluoro-3,5-dimethoxy phenyl)-3,4-dihydro-1H-pyrimido[4,5-d]pyrimidin-2-one;

1-Cyclopentyl-7-(4-hydroxy-cyclohexylamino)-3-(2,6-difluoro-3-methoxy-5-ethoxy phenyl)-3,4-dihydro-1H-pyrimido[4,5-d]pyrimidin-2-one;

1-Cyclopentyl-7-(4-hydroxy-cyclohexylamino)-3-(2,6-difluoro-3-hydroxy-5-ethoxy phenyl)-3,4-dihydro-1H-pyrimido[4,5-d]pyrimidin-2-one;

1-Cyclopentyl-7-(4-hydroxy-cyclohexylamino)-3-(2,6-difluoro-3-methoxy-phenyl)-3,4-dihydro-1H-pyrimido[4,5-d]pyrimidin-2-one;

1-Cyclopentyl-7-(4-hydroxy-cyclohexylamino)-3-(2,6-difluoro-3-ethoxy-phenyl)-3,4-dihydro-1H-pyrimido[4,5-d]pyrimidin-2-one;

1-Cyclopentyl-7-(4-hydroxy-cyclohexylamino)-3-(2,6-difluoro-3-hydroxy-phenyl)-3,4-dihydro-1H-pyrimido[4,5-d]pyrimidin-2-one;

1-Cyclopropyl-7-(4-hydroxy-cyclohexylamino)-3-(2,6-difluoro-3-hydroxy-5-methoxy phenyl)-3,4-dihydro-1H-pyrimido[4,5-d]pyrimidin-2-one;

1-Cyclopropyl-7-(4-hydroxy-cyclohexylamino)-3-(2,6-difluoro-3,5-dimethoxy phenyl)-3,4-dihydro-1H-pyrimido[4,5-d]pyrimidin-2-one;

1-Cyclopropyl-7-(4-hydroxy-cyclohexylamino)-3-(2,6-difluoro-3-methoxy-5-ethoxy phenyl)-3,4-dihydro-1H-pyrimido[4,5-d]pyrimidin-2-one;

1-Cyclopropyl-7-(4-hydroxy-cyclohexylamino)-3-(2,6-difluoro-3-hydroxy-5-ethoxy phenyl)-3,4-dihydro-1H-pyrimido[4,5-d]pyrimidin-2-one;

1-Cyclopropyl-7-(4-hydroxy-cyclohexylamino)-3-(2,6-difluoro-3-methoxy-phenyl)-3,4-dihydro-1H-pyrimido[4,5-d]pyrimidin-2-one;

1-Cyclopropyl-7-(4-hydroxy-cyclohexylamino)-3-(2,6-difluoro-3-ethoxy-phenyl)-3,4-dihydro-1H-pyrimido[4,5-d]pyrimidin-2-one;

1-Cyclopropyl-7-(4-hydroxy-cyclohexylamino)-3-(2,6-difluoro-3-hydroxy-phenyl)-3,4-dihydro-1H-pyrimido[4,5-d]pyrimidin-2-one;

1-Ethyl-7-(4-hydroxy-cyclohexylamino)-3-(2,6-difluoro-3-hydroxy-5-methoxy phenyl)-3,4-dihydro-1H-pyrimido[4,5-d]pyrimidin-2-one;

1-Ethyl-7-(4-hydroxy-cyclohexylamino)-3-(2,6-difluoro-3,5-dimethoxy phenyl)-3,4-dihydro-1H-pyrimido[4,5-d]pyrimidin-2-one;

1-Ethyl-7-(4-hydroxy-cyclohexylamino)-3-(2,6-difluoro-3-methoxy-5-ethoxy phenyl)-3,4-dihydro-1H-pyrimido[4,5-d]pyrimidin-2-one;

1-Ethyl-7-(4-hydroxy-cyclohexylamino)-3-(2,6-difluoro-3-hydroxy-5-ethoxy phenyl)-3,4-dihydro-1H-pyrimido[4,5-d]pyrimidin-2-one;

1-Ethyl-7-(4-hydroxy-cyclohexylamino)-3-(2,6-difluoro-3-methoxy-phenyl)-3,4-dihydro-1H-pyrimido[4,5-d]pyrimidin-2-one;

1-Ethyl-7-(4-hydroxy-cyclohexylamino)-3-(2,6-difluoro-3-ethoxy-phenyl)-3,4-dihydro-1H-pyrimido[4,5-d]pyrimidin-2-one;

1-Ethyl-7-(4-hydroxy-cyclohexylamino)-3-(2,6-difluoro-3-hydroxy-phenyl)-3,4-dihydro-1H-pyrimido[4,5-d]pyrimidin-2-one;

1-Cyclopentyl-7-(4-hydroxy-cyclohexylamino)-3-(2-fluoro-3-hydroxy-5-methoxy phenyl)-3,4-dihydro-1H-pyrimido[4,5-d]pyrimidin-2-one;

1-Cyclopentyl-7-(4-hydroxy-cyclohexylamino)-3-(2-fluoro-3,5-dimethoxy phenyl)-3,4-dihydro-1H-pyrimido[4,5-d]pyrimidin-2-one;

1-Cyclopentyl-7-(4-hydroxy-cyclohexylamino)-3-(2-fluoro-3-methoxy-5-ethoxy phenyl)-3,4-dihydro-1H-pyrimido[4,5-d]pyrimidin-2-one;

1-Cyclopentyl-7-(4-hydroxy-cyclohexylamino)-3-(2-fluoro-3-hydroxy-5-ethoxy phenyl)-3,4-dihydro-1H-pyrimido[4,5-d]pyrimidin-2-one;

1-Cyclopentyl-7-(4-hydroxy-cyclohexylamino)-3-(2-fluoro-3-methoxy-phenyl)-3,4-dihydro-1H-pyrimido[4,5-d]pyrimidin-2-one;

1-Cyclopentyl-7-(4-hydroxy-cyclohexylamino)-3-(2-fluoro-3-ethoxy-phenyl)-3,4-dihydro-1H-pyrimido[4,5-d]pyrimidin-2-one;

1-Cyclopentyl-7-(4-hydroxy-cyclohexylamino)-3-(2-difluoro-3-hydroxy-phenyl)-3,4-dihydro-1H-pyrimido[4,5-d]pyrimidin-2-one;

1-Cyclopropyl-7-(4-hydroxy-cyclohexylamino)-3-(2-fluoro-3-hydroxy-5-methoxy phenyl)-3,4-dihydro-1H-pyrimido[4,5-d]pyrimidin-2-one;

1-Cyclopropyl-7-(4-hydroxy-cyclohexylamino)-3-(2-fluoro-3,5-dimethoxy phenyl)-3,4-dihydro-1H-pyrimido[4,5-d]pyrimidin-2-one;

1-Cyclopropyl-7-(4-hydroxy-cyclohexylamino)-3-(2-fluoro-3-methoxy-5-ethoxy phenyl)-3,4-dihydro-1H-pyrimido[4,5-d]pyrimidin-2-one;

1-Cyclopropyl-7-(4-hydroxy-cyclohexylamino)-3-(2-fluoro-3-hydroxy-5-ethoxy phenyl)-3,4-dihydro-1H-pyrimido[4,5-d]pyrimidin-2-one;

1-Cyclopropyl-7-(4-hydroxy-cyclohexylamino)-3-(2-fluoro-3-methoxy-phenyl)-3,4-dihydro-1H-pyrimido[4,5-d]pyrimidin-2-one;

1-Cyclopropyl-7-(4-hydroxy-cyclohexylamino)-3-(2-fluoro-3-ethoxy-phenyl)-3,4-dihydro-1H-pyrimido[4,5-d]pyrimidin-2-one;

1-Cyclopropyl-7-(4-hydroxy-cyclohexylamino)-3-(2-difluoro-3-hydroxy-phenyl)-3,4-dihydro-1H-pyrimido[4,5-d]pyrimidin-2-one;

1-Ethyl-7-(4-hydroxy-cyclohexylamino)-3-(2-fluoro-3-hydroxy-5-methoxy phenyl)-3,4-dihydro-1H-pyrimido[4,5-d]pyrimidin-2-one;

1-Ethyl-7-(4-hydroxy-cyclohexylamino)-3-(2-fluoro-3,5-dimethoxy phenyl)-3,4-dihydro-1H-pyrimido[4,5-d]pyrimidin-2-one;

1-Ethyl-7-(4-hydroxy-cyclohexylamino)-3-(2-fluoro-3-methoxy-5-ethoxy phenyl)-3,4-dihydro-1H-pyrimido[4,5-d]pyrimidin-2-one;

1-Ethyl-7-(4-hydroxy-cyclohexylamino)-3-(2-fluoro-3-hydroxy-5-ethoxy phenyl)-3,4-dihydro-1H-pyrimido[4,5-d]pyrimidin-2-one;

1-Ethyl-7-(4-hydroxy-cyclohexylamino)-3-(2-fluoro-3-methoxy-phenyl)-3,4-dihydro-1H-pyrimido[4,5-d]pyrimidin-2-one;

1-Ethyl-7-(4-hydroxy-cyclohexylamino)-3-(2-fluoro-3-ethoxy-phenyl)-3,4-dihydro-1H-pyrimido[4,5-d]pyrimidin-2-one;

1-Ethyl-7-(4-hydroxy-cyclohexylamino)-3-(2-difluoro-3-hydroxy-phenyl)-3,4-dihydro-1H-pyrimido[4,5-d]pyrimidin-2-one;

1-Cyclopentyl-7-(4-hydroxy-cyclohexylamino)-3-(2-fluoro-6-chloro-3-hydroxy-5-methoxy phenyl)-3,4-dihydro-1H-pyrimido[4,5-d]pyrimidin-2-one;

1-Cyclopentyl-7-(4-hydroxy-cyclohexylamino)-3-(2-fluoro-6-chloro-3,5-dimethoxy phenyl)-3,4-dihydro-1H-pyrimido[4,5-d]pyrimidin-2-one;

1-Cyclopentyl-7-(4-hydroxy-cyclohexylamino)-3-(2-fluoro-6-chloro-3-methoxy-5-ethoxy phenyl)-3,4-dihydro-1H-pyrimido[4,5-d]pyrimidin-2-one;

1-Cyclopentyl-7-(4-hydroxy-cyclohexylamino)-3-(2-fluoro-6-chloro-3-hydroxy-5-ethoxy phenyl)-3,4-dihydro-1H-pyrimido[4,5-d]pyrimidin-2-one;

1-Cyclopentyl-7-(4-hydroxy-cyclohexylamino)-3-(2-fluoro-6-chloro-3-methoxy-phenyl)-3,4-dihydro-1H-pyrimido[4,5-d]pyrimidin-2-one;

1-Cyclopentyl-7-(4-hydroxy-cyclohexylamino)-3-(2-fluoro-6-chloro-3-ethoxy-phenyl)-3,4-dihydro-1H-pyrimido[4,5-d]pyrimidin-2-one;

1-Cyclopentyl-7-(4-hydroxy-cyclohexylamino)-3-(2-difluoro-6-chloro-3-hydroxy-phenyl)-3,4-dihydro-1H-pyrimido[4,5-d]pyrimidin-2-one;

1-Cyclopropyl-7-(4-hydroxy-cyclohexylamino)-3-(2-fluoro-6-chloro-3-hydroxy-5-methoxy phenyl)-3,4-dihydro-1H-pyrimido[4,5-d]pyrimidin-2-one;

1-Cyclopropyl-7-(4-hydroxy-cyclohexylamino)-3-(2-fluoro-6-chloro-3,5-dimethoxy phenyl)-3,4-dihydro-1H-pyrimido[4,5-d]pyrimidin-2-one;

1-Cyclopropyl-7-(4-hydroxy-cyclohexylamino)-3-(2-fluoro-6-chloro-3-methoxy-5-ethoxy phenyl)-3,4-dihydro-1H-pyrimido[4,5-d]pyrimidin-2-one;

1-Cyclopropyl-7-(4-hydroxy-cyclohexylamino)-3-(2-fluoro-6-chloro-3-hydroxy-5-ethoxy phenyl)-3,4-dihydro-1H-pyrimido[4,5-d]pyrimidin-2-one;

1-Cyclopropyl-7-(4-hydroxy-cyclohexylamino)-3-(2-fluoro-6-chloro-3-methoxy-phenyl)-3,4-dihydro-1H-pyrimido[4,5-d]pyrimidin-2-one;

1-Cyclopropyl-7-(4-hydroxy-cyclohexylamino)-3-(2-fluoro-6-chloro-3-ethoxy-phenyl)-3,4-dihydro-1H-pyrimido[4,5-d]pyrimidin-2-one;

1-Cyclopropyl-7-(4-hydroxy-cyclohexylamino)-3-(2-difluoro-6-chloro-3-hydroxy-phenyl)-3,4-dihydro-1H-pyrimido[4,5-d]pyrimidin-2-one;

1-Ethyl-7-(4-hydroxy-cyclohexylamino)-3-(2-fluoro-6-chloro-3-hydroxy-5-methoxy phenyl)-3,4-dihydro-1H-pyrimido[4,5-d]pyrimidin-2-one;

1-Ethyl-7-(4-hydroxy-cyclohexylamino)-3-(2-fluoro-6-chloro-3,5-dimethoxy phenyl)-3,4-dihydro-1H-pyrimido[4,5-d]pyrimidin-2-one;

1-Ethyl-7-(4-hydroxy-cyclohexylamino)-3-(2-fluoro-6-chloro-3-methoxy-5-ethoxy phenyl)-3,4-dihydro-1H-pyrimido[4,5-d]pyrimidin-2-one;

1-Ethyl-7-(4-hydroxy-cyclohexylamino)-3-(2-fluoro-6-chloro-3-hydroxy-5-ethoxy phenyl)-3,4-dihydro-1H-pyrimido[4,5-d]pyrimidin-2-one;

1-Ethyl-7-(4-hydroxy-cyclohexylamino)-3-(2-fluoro-6-chloro-3-methoxy-phenyl)-3,4-dihydro-1H-pyrimido[4,5-d]pyrimidin-2-one;

1-Ethyl-7-(4-hydroxy-cyclohexylamino)-3-(2-fluoro-6-chloro-3-ethoxy-phenyl)-3,4-dihydro-1H-pyrimido[4,5-d]pyrimidin-2-one;

1-Ethyl-7-(4-hydroxy-cyclohexylamino)-3-(2-difluoro-6-chloro-3-hydroxy-phenyl)-3,4-dihydro-1H-pyrimido[4,5-d]pyrimidin-2-one;

1-Cyclopentyl-7-(4-dimethylamino-cyclohexylamino)-3-(2,6-difluoro-3-hydroxy-5-methoxy phenyl)-3,4-dihydro-1H-pyrimido[4,5-d]pyrimidin-2-one;

1-Cyclopentyl-7-(4-dimethylamino-cyclohexylamino)-3-(2,6-difluoro-3,5-dimethoxy phenyl)-3,4-dihydro-1H-pyrimido[4,5-d]pyrimidin-2-one;

1-Cyclopentyl-7-(4-dimethylamino-cyclohexylamino)-3-(2,6-difluoro-3-methoxy-5-ethoxy phenyl)-3,4-dihydro-1H-pyrimido[4,5-d]pyrimidin-2-one;

1-Cyclopentyl-7-(4-dimethylamino-cyclohexylamino)-3-(2,6-difluoro-3-hydroxy-5-ethoxy phenyl)-3,4-dihydro-1H-pyrimido[4,5-d]pyrimidin-2-one;

1-Cyclopentyl-7-(4-dimethylamino-cyclohexylamino)-3-(2,6-difluoro-3-methoxy-phenyl)-3,4-dihydro-1H-pyrimido[4,5-d]pyrimidin-2-one;

1-Cyclopentyl-7-(4-dimethylamino-cyclohexylamino)-3-(2,6-difluoro-3-ethoxy-phenyl)-3,4-dihydro-1H-pyrimido[4,5-d]pyrimidin-2-one;

1-Cyclopentyl-7-(4-dimethylamino-cyclohexylamino)-3-(2,6-difluoro-3-hydroxy-phenyl)-3,4-dihydro-1H-pyrimido[4,5-d]pyrimidin-2-one;

1-Cyclopropyl-7-(4-dimethylamino-cyclohexylamino)-3-(2,6-difluoro-3-hydroxy-5-methoxy phenyl)-3,4-dihydro-1H-pyrimido[4,5-d]pyrimidin-2-one;

1-Cyclopropyl-7-(4-dimethylamino-cyclohexylamino)-3-(2,6-difluoro-3,5-dimethoxy phenyl)-3,4-dihydro-1H-pyrimido[4,5-d]pyrimidin-2-one;

1-Cyclopropyl-7-(4-dimethylamino-cyclohexylamino)-3-(2,6-difluoro-3-methoxy-5-ethoxy phenyl)-3,4-dihydro-1H-pyrimido[4,5-d]pyrimidin-2-one;

1-Cyclopropyl-7-(4-dimethylamino-cyclohexylamino)-3-(2,6-difluoro-3-hydroxy-5-ethoxy phenyl)-3,4-dihydro-1H-pyrimido[4,5-d]pyrimidin-2-one;

1-Cyclopropyl-7-(4-dimethylamino-cyclohexylamino)-3-(2,6-difluoro-3-methoxy-phenyl)-3,4-dihydro-1H-pyrimido[4,5-d]pyrimidin-2-one;

1-Cyclopropyl-7-(4-dimethylamino-cyclohexylamino)-3-(2,6-difluoro-3-ethoxy-phenyl)-3,4-dihydro-1H-pyrimido[4,5-d]pyrimidin-2-one;

1-Cyclopropyl-7-(4-dimethylamino-cyclohexylamino)-3-(2,6-difluoro-3-hydroxy-phenyl)-3,4-dihydro-1H-pyrimido[4,5-d]pyrimidin-2-one;

1-Ethyl-7-(4-dimethylamino-cyclohexylamino)-3-(2,6-difluoro-3-hydroxy-5-methoxy phenyl)-3,4-dihydro-1H-pyrimido[4,5-d]pyrimidin-2-one;

1-Ethyl-7-(4-dimethylamino-cyclohexylamino)-3-(2,6-difluoro-3,5-dimethoxy phenyl)-3,4-dihydro-1H-pyrimido[4,5-d]pyrimidin-2-one;

1-Ethyl-7-(4-dimethylamino-cyclohexylamino)-3-(2,6-difluoro-3-methoxy-5-ethoxy phenyl)-3,4-dihydro-1H-pyrimido[4,5-d]pyrimidin-2-one;

1-Ethyl-7-(4-dimethylamino-cyclohexylamino)-3-(2,6-difluoro-3-hydroxy-5-ethoxy phenyl)-3,4-dihydro-1H-pyrimido[4,5-d]pyrimidin-2-one;

1-Ethyl-7-(4-dimethylamino-cyclohexylamino)-3-(2,6-difluoro-3-methoxy-phenyl)-3,4-dihydro-1H-pyrimido[4,5-d]pyrimidin-2-one;

1-Ethyl-7-(4-dimethylamino-cyclohexylamino)-3-(2,6-difluoro-3-ethoxy-phenyl)-3,4-dihydro-1H-pyrimido[4,5-d]pyrimidin-2-one;

1-Ethyl-7-(4-dimethylamino-cyclohexylamino)-3-(2,6-difluoro-3-hydroxy-phenyl)-3,4-dihydro-1H-pyrimido[4,5-d]pyrimidin-2-one;

1-Cyclopentyl-7-(4-dimethylamino-cyclohexylamino)-3-(2-fluoro-3-hydroxy-5-methoxy phenyl)-3,4-dihydro-1H-pyrimido[4,5-d]pyrimidin-2-one;

1-Cyclopentyl-7-(4-dimethylamino-cyclohexylamino)-3-(2-fluoro-3,5-dimethoxy phenyl)-3,4-dihydro-1H-pyrimido[4,5-d]pyrimidin-2-one;

1-Cyclopentyl-7-(4-dimethylamino-cyclohexylamino)-3-(2-fluoro-3-methoxy-5-ethoxy phenyl)-3,4-dihydro-1H-pyrimido[4,5-d]pyrimidin-2-one;

1-Cyclopentyl-7-(4-dimethylamino-cyclohexylamino)-3-(2-fluoro-3-hydroxy-5-ethoxy phenyl)-3,4-dihydro-1H-pyrimido[4,5-d]pyrimidin-2-one;

1-Cyclopentyl-7-(4-dimethylamino-cyclohexylamino)-3-(2-fluoro-3-methoxy-phenyl)-3,4-dihydro-1H-pyrimido[4,5-d]pyrimidin-2-one;

1-Cyclopentyl-7-(4-dimethylamino-cyclohexylamino)-3-(2-fluoro-3-ethoxy-phenyl)-3,4-dihydro-1H-pyrimido[4,5-d]pyrimidin-2-one;

1-Cyclopentyl-7-(4-dimethylamino-cyclohexylamino)-3-(2-difluoro-3-hydroxy-phenyl)-3,4-dihydro-1H-pyrimido[4,5-d]pyrimidin-2-one;

1-Cyclopropyl-7-(4-dimethylamino-cyclohexylamino)-3-(2-fluoro-3-hydroxy-5-methoxy phenyl)-3,4-dihydro-1H-pyrimido[4,5-d]pyrimidin-2-one;

1-Cyclopropyl-7-(4-dimethylamino-cyclohexylamino)-3-(2-fluoro-3,5-dimethoxy phenyl)-3,4-dihydro-1H-pyrimido[4,5-d]pyrimidin-2-one;

1-Cyclopropyl-7-(4-dimethylamino-cyclohexylamino)-3-(2-fluoro-3-methoxy-5-ethoxy phenyl)-3,4-dihydro-1H-pyrimido[4,5-d]pyrimidin-2-one;

1-Cyclopropyl-7-(4-dimethylamino-cyclohexylamino)-3-(2-fluoro-3-hydroxy-5-ethoxy phenyl)-3,4-dihydro-1H-pyrimido[4,5-d]pyrimidin-2-one;

1-Cyclopropyl-7-(4-dimethylamino-cyclohexylamino)-3-(2-fluoro-3-methoxy-phenyl)-3,4-dihydro-1H-pyrimido[4,5-d]pyrimidin-2-one;

1-Cyclopropyl-7-(4-dimethylamino-cyclohexylamino)-3-(2-fluoro-3-ethoxy-phenyl)-3,4-dihydro-1H-pyrimido[4,5-d]pyrimidin-2-one;

1-Cyclopropyl-7-(4-dimethylamino-cyclohexylamino)-3-(2-difluoro-3-hydroxy-phenyl)-3,4-dihydro-1H-pyrimido[4,5-d]pyrimidin-2-one;

1-Ethyl-7-(4-dimethylamino-cyclohexylamino)-3-(2-fluoro-3-hydroxy-5-methoxy phenyl)-3,4-dihydro-1H-pyrimido[4,5-d]pyrimidin-2-one;

1-Ethyl-7-(4-dimethylamino-cyclohexylamino)-3-(2-fluoro-3,5-dimethoxy phenyl)-3,4-dihydro-1H-pyrimido[4,5-d]pyrimidin-2-one;

1-Ethyl-7-(4-dimethylamino-cyclohexylamino)-3-(2-fluoro-3-methoxy-5-ethoxy phenyl)-3,4-dihydro-1H-pyrimido[4,5-d]pyrimidin-2-one;

1-Ethyl-7-(4-dimethylamino-cyclohexylamino)-3-(2-fluoro-3-hydroxy-5-ethoxy phenyl)-3,4-dihydro-1H-pyrimido[4,5-d]pyrimidin-2-one;

1-Ethyl-7-(4-dimethylamino-cyclohexylamino)-3-(2-fluoro-3-methoxy-phenyl)-3,4-dihydro-1H-pyrimido[4,5-d]pyrimidin-2-one;

1-Ethyl-7-(4-dimethylamino-cyclohexylamino)-3-(2-fluoro-3-ethoxy-phenyl)-3,4-dihydro-1H-pyrimido[4,5-d]pyrimidin-2-one;

1-Ethyl-7-(4-dimethylamino-cyclohexylamino)-3-(2-difluoro-3-hydoxy-phenyl)-3,4-dihydro-1H-pyrimido[4,5-d]pyrimidin-2-one;

1-Cyclopentyl-7-(4-dimethylamino-cyclohexylamino)-3-(2-fluoro-6-chloro-3-hydroxy-5-methoxy phenyl)-3,4-dihydro-1H-pyrimido[4,5-d]pyrimidin-2-one;

1-Cyclopentyl-7-(4-dimethylamino-cyclohexylamino)-3-(2-fluoro-6-chloro-3,5-dimethoxy phenyl)-3,4-dihydro-1H-pyrimido[4,5-d]pyrimidin-2-one;

1-Cyclopentyl-7-(4-dimethylamino-cyclohexylamino)-3-(2-fluoro-6-chloro-3-methoxy-5-ethoxy phenyl)-3,4-dihydro-1H-pyrimido[4,5-d]pyrimidin-2-one;

1-Cyclopentyl-7-(4-dimethylamino-cyclohexylamino)-3-(2-fluoro-6-chloro-3-hydroxy-5-ethoxy phenyl)-3,4-dihydro-1H-pyrimido[4,5-d]pyrimidin-2-one;

1-Cyclopentyl-7-(4-dimethylamino-cyclohexylamino)-3-(2-fluoro-6-chloro-3-methoxy-phenyl)-3,4-dihydro-1H-pyrimido[4,5-d]pyrimidin-2-one;

1-Cyclopentyl-7-(4-dimethylamino-cyclohexylamino)-3-(2-fluoro-6-chloro-3-ethoxy-phenyl)-3,4-dihydro-1H-pyrimido[4,5-d]pyrimidin-2-one;

1-Cyclopentyl-7-(4-dimethylamino-cyclohexylamino)-3-(2-difluoro-6-chloro-3-hydoxy-phenyl)-3,4-dihydro-1H-pyrimido[4,5-d]pyrimidin-2-one;

1-Cyclopropyl-7-(4-dimethylamino-cyclohexylamino)-3-(2-fluoro-6-chloro-3-hydroxy-5-methoxy phenyl)-3,4-dihydro-1H-pyrimido[4,5-d]pyrimidin-2-one;

1-Cyclopropyl-7-(4-dimethylamino-cyclohexylamino)-3-(2-fluoro-6-chloro-3,5-dimethoxy phenyl)-3,4-dihydro-1H-pyrimido[4,5-d]pyrimidin-2-one;

1-Cyclopropyl-7-(4-dimethylamino-cyclohexylamino)-3-(2-fluoro-6-chloro-3-methoxy-5-ethoxy phenyl)-3,4-dihydro-1H-pyrimido[4,5-d]pyrimidin-2-one;

1-Cyclopropyl-7-(4-dimethylamino-cyclohexylamino)-3-(2-fluoro-6-chloro-3-hydroxy-5-ethoxy phenyl)-3,4-dihydro-1H-pyrimido[4,5-d]pyrimidin-2-one;

1-Cyclopropyl-7-(4-dimethylamino-cyclohexylamino)-3-(2-fluoro-6-chloro-3-methoxy-phenyl)-3,4-dihydro-1H-pyrimido[4,5-d]pyrimidin-2-one;

1-Cyclopropyl-7-(4-dimethylamino-cyclohexylamino)-3-(2-fluoro-6-chloro-3-ethoxy-phenyl)-3,4-dihydro-1H-pyrimido[4,5-d]pyrimidin-2-one;

1-Cyclopropyl-7-(4-dimethylamino-cyclohexylamino)-3-(2-difluoro-6-chloro-3-hydoxy-phenyl)-3,4-dihydro-1H-pyrimido[4,5-d]pyrimidin-2-one;

1-Ethyl-7-(4-dimethylamino-cyclohexylamino)-3-(2-fluoro-6-chloro-3-hydroxy-5-methoxy phenyl)-3,4-dihydro-1H-pyrimido[4,5-d]pyrimidin-2-one;

1-Ethyl-7-(4-dimethylamino-cyclohexylamino)-3-(2-fluoro-6-chloro-3,5-dimethoxy phenyl)-3,4-dihydro-1H-pyrimido[4,5-d]pyrimidin-2-one;

1-Ethyl-7-(4-dimethylamino-cyclohexylamino)-3-(2-fluoro-6-chloro-3-methoxy-5-ethoxy phenyl)-3,4-dihydro-1H-pyrimido[4,5-d]pyrimidin-2-one;

1-Ethyl-7-(4-dimethylamino-cyclohexylamino)-3-(2-fluoro-6-chloro-3-hydroxy-5-ethoxy phenyl)-3,4-dihydro-1H-pyrimido[4,5-d]pyrimidin-2-one;

1-Ethyl-7-(4-dimethylamino-cyclohexylamino)-3-(2-fluoro-6-chloro-3-methoxy-phenyl)-3,4-dihydro-1H-pyrimido[4,5-d]pyrimidin-2-one;

1-Ethyl-7-(4-dimethylamino-cyclohexylamino)-3-(2-fluoro-6-chloro-3-ethoxy-phenyl)-3,4-dihydro-1H-pyrimido[4,5-d]pyrimidin-2-one;

1-Ethyl-7-(4-dimethylamino-cyclohexylamino)-3-(2-difluoro-6-chloro-3-hydroxy-phenyl)-3,4-dihydro-1H-pyrimido[4,5-d]pyrimidin-2-one;

1-Cyclopentyl-7-[5-(4-methyl-piperazin-1-yl)-pentylamino]-3-(2,6-difluoro-3-hydroxy-5-methoxy phenyl)-3,4-dihydro-1H-pyrimido[4,5-d]pyrimidin-2-one;

1-Cyclopentyl-7-[5-(4-methyl-piperazin-1-yl)-pentylamino]-3-(2,6-difluoro-3,5-dimethoxy phenyl)-3,4-dihydro-1H-pyrimido[4,5-d]pyrimidin-2-one;

1-Cyclopentyl-7-[5-(4-methyl-piperazin-1-yl)-pentylamino]-3-(2,6-difluoro-3-methoxy-5-ethoxy phenyl)-3,4-dihydro-1H-pyrimido[4,5-d]pyrimidin-2-one;

1-Cyclopentyl-7-[5-(4-methyl-piperazin-1-yl)-pentylamino]-3-(2,6-difluoro-3-hydroxy-5-ethoxy phenyl)-3,4-dihydro-1H-pyrimido[4,5-d]pyrimidin-2-one;

1-Cyclopentyl-7-[5-(4-methyl-piperazin-1-yl)-pentylamino]-3-(2,6-difluoro-3-methoxy-phenyl)-3,4-dihydro-1H-pyrimido[4,5-d]pyrimidin-2-one;

1-Cyclopentyl-7-[5-(4-methyl-piperazin-1-yl)-pentylamino]-3-(2,6-difluoro-3-ethoxy-phenyl)-3,4-dihydro-1H-pyrimido[4,5-d]pyrimidin-2-one;

1-Cyclopentyl-7-[5-(4-methyl-piperazin-1-yl)-pentylamino]-3-(2,6-difluoro-3-hydoxy-phenyl)-3,4-dihydro-1H-pyrimido[4,5-d]pyrimidin-2-one;

1-Cyclopropyl-7-[5-(4-methyl-piperazin-1-yl)-pentylamino]-3-(2,6-difluoro-3-hydroxy-5-methoxy phenyl)-3,4-dihydro-1H-pyrimido[4,5-d]pyrimidin-2-one;

1-Cyclopropyl-7-[5-(4-methyl-piperazin-1-yl)-pentylamino]-3-(2,6-difluoro-3,5-dimethoxy phenyl)-3,4-dihydro-1H-pyrimido[4,5-d]pyrimidin-2-one;

1-Cyclopropyl-7-[5-(4-methyl-piperazin-1-yl)-pentylamino]-3-(2,6-difluoro-3-methoxy-5-ethoxy phenyl)-3,4-dihydro-1H-pyrimido[4,5-d]pyrimidin-2-one;

1-Cyclopropyl-7-[5-(4-methyl-piperazin-1-yl)-pentylamino]-3-(2,6-difluoro-3-hydroxy-5-ethoxy phenyl)-3,4-dihydro-1H-pyrimido[4,5-d]pyrimidin-2-one;

1-Cyclopropyl-7-[5-(4-methyl-piperazin-1-yl)-pentylamino]-3-(2,6-difluoro-3-methoxy-phenyl)-3,4-dihydro-1H-pyrimido[4,5-d]pyrimidin-2-one;

1-Cyclopropyl-7-[5-(4-methyl-piperazin-1-yl)-pentylamino]-3-(2,6-difluoro-3-ethoxy-phenyl)-3,4-dihydro-1H-pyrimido[4,5-d]pyrimidin-2-one;

1-Cyclopropyl-7-[5-(4-methyl-piperazin-1-yl)-pentylamino]-3-(2,6-difluoro-3-hydoxy-phenyl)-3,4-dihydro-1H-pyrimido[4,5-d]pyrimidin-2-one;

1-Ethyl-7-[5-(4-methyl-piperazin-1-yl)-pentylamino]-3-(2,6-difluoro-3-hydroxy-5-methoxy phenyl)-3,4-dihydro-1H-pyrimido[4,5-d]pyrimidin-2-one;

1-Ethyl-7-[5-(4-methyl-piperazin-1-yl)-pentylamino]-3-(2,6-difluoro-3,5-dimethoxy phenyl)-3,4-dihydro-1H-pyrimido[4,5-d]pyrimidin-2-one;

1-Ethyl-7-[5-(4-methyl-piperazin-1-yl)-pentylamino]-3-(2,6-difluoro-3-methoxy-5-ethoxy phenyl)-3,4-dihydro-1H-pyrimido[4,5-d]pyrimidin-2-one;

1-Ethyl-7-[5-(4-methyl-piperazin-1-yl)-pentylamino]-3-(2,6-difluoro-3-hydroxy-5-ethoxy phenyl)-3,4-dihydro-1H-pyrimido[4,5-d]pyrimidin-2-one;

1-Ethyl-7-[5-(4-methyl-piperazin-1-yl)-pentylamino]-3-(2,6-difluoro-3-methoxy-phenyl)-3,4-dihydro-1H-pyrimido[4,5-d]pyrimidin-2-one;

1-Ethyl-7-[5-(4-methyl-piperazin-1-yl)-pentylamino]-3-(2,6-difluoro-3-ethoxy-phenyl)-3,4-dihydro-1H-pyrimido[4,5-d]pyrimidin-2-one;

1-Ethyl-7-[5-(4-methyl-piperazin-1-yl)-pentylamino]-3-(2,6-difluoro-3-hydroxy-phenyl)-3,4-dihydro-1H-pyrimido[4,5-d]pyrimidin-2-one;

1-Cyclopentyl-7-[5-(4-methyl-piperazin-1-yl)-pentylamino]-3-(2-fluoro-6-chloro-3-hydroxy-5-methoxy phenyl)-3,4-dihydro-1H-pyrimido[4,5-d]pyrimidin-2-one;

1-Cyclopentyl-7-[5-(4-methyl-piperazin-1-yl)-pentylamino]-3-(2-fluoro-6-chloro-3,5-dimethoxy phenyl)-3,4-dihydro-1H-pyrimido[4,5-d]pyrimidin-2-one;

1-Cyclopentyl-7-[5-(4-methyl-piperazin-1-yl)-pentylamino]-3-(2-fluoro-6-chloro-3-methoxy-5-ethoxy phenyl)-3,4-dihydro-1H-pyrimido[4,5-d]pyrimidin-2-one;

1-Cyclopentyl-7-[5-(4-methyl-piperazin-1-yl)-pentylamino]-3-(2-fluoro-6-chloro-3-hydroxy-5-ethoxy phenyl)-3,4-dihydro-1H-pyrimido[4,5-d]pyrimidin-2-one;

1-Cyclopentyl-7-[5-(4-methyl-piperazin-1-yl)-pentylamino]-3-(2-fluoro-6-chloro-3-methoxy-phenyl)-3,4-dihydro-1H-pyrimido[4,5-d]pyrimidin-2-one;

1-Cyclopentyl-7-[5-(4-methyl-piperazin-1-yl)-pentylamino]-3-(2-fluoro-6-chloro-3-ethoxy-phenyl)-3,4-dihydro-1H-pyrimido[4,5-d]pyrimidin-2-one;

1-Cyclopentyl-7-[5-(4-methyl-piperazin-1-yl)-pentylamino]-3-(2-difluoro-6-chloro-3-hydoxy-phenyl)-3,4-dihydro-1H-pyrimido[4,5-d]pyrimidin-2-one;

1-Cyclopropyl-7-[5-(4-methyl-piperazin-1-yl)-pentylamino]-3-(2-fluoro-6-chloro-3-hydroxy-5-methoxy phenyl)-3,4-dihydro-1H-pyrimido[4,5-d]pyrimidin-2-one;

1-Cyclopropyl-7-[5-(4-methyl-piperazin-1-yl)-pentylamino]-3-(2-fluoro-6-chloro-3,5-dimethoxy phenyl)-3,4-dihydro-1H-pyrimido[4,5-d]pyrimidin-2-one;

1-Cyclopropyl-7-[5-(4-methyl-piperazin-1-yl)-pentylamino]-3-(2-fluoro-6-chloro-3-methoxy-5-ethoxy phenyl)-3,4-dihydro-1H-pyrimido[4,5-d]pyrimidin-2-one;

1-Cyclopropyl-7-[5-(4-methyl-piperazin-1-yl)-pentylamino]-3-(2-fluoro-6-chloro-3-hydroxy-5-ethoxy phenyl)-3,4-dihydro-1H-pyrimido[4,5-d]pyrimidin-2-one;

1-Cyclopropyl-7-[5-(4-methyl-piperazin-1-yl)-pentyl amino]-3-(2-fluoro-6-chloro-3-methoxy-phenyl)-3,4-dihydro-1H-pyrimido[4,5-d]pyrimidin-2-one;

1-Cyclopropyl-7-[5-(4-methyl-piperazin-1-yl)-pentylamino]-3-(2-fluoro-6-chloro-3-ethoxy-phenyl)-3,4-dihydro-1H-pyrimido[4,5-d]pyrimidin-2-one;

1-Cyclopropyl-7-[5-(4-methyl-piperazin-1-yl)-pentylamino]-3-(2-difluoro-6-chloro-3-hydoxy-phenyl)-3,4-dihydro-1H-pyrimido[4,5-d]pyrimidin-2-one;

1-Ethyl-7-[5-(4-methyl-piperazin-1-yl)-pentylamino]-3-(2-fluoro-6-chloro-3-hydroxy-5-methoxy phenyl)-3,4-dihydro-1H-pyrimido[4,5-d]pyrimidin-2-one;

1-Ethyl-7-[5-(4-methyl-piperazin-1-yl)-pentylamino]-3-(2-fluoro-6-chloro-3,5-dimethoxy phenyl)-3,4-dihydro-1H-pyrimido[4,5-d]pyrimidin-2-one;

1-Ethyl-7-[5-(4-methyl-piperazin-1-yl)-pentylamino]-3-(2-fluoro-6-chloro-3-methoxy-5-ethoxy phenyl)-3,4-dihydro-1H-pyrimido[4,5-d]pyrimidin-2-one;

1-Ethyl-7-[5-(4-methyl-piperazin-1-yl)-pentylamino]-3-(2-fluoro-6-chloro-3-hydroxy-5-ethoxy phenyl)-3,4-dihydro-1H-pyrimido[4,5-d]pyrimidin-2-one;

1-Ethyl-7-[5-(4-methyl-piperazin-1-yl)-pentylamino]-3-(2-fluoro-6-chloro-3-methoxy-phenyl)-3,4-dihydro-1H-pyrimido[4,5-d]pyrimidin-2-one;

1-Ethyl-7-[5-(4-methyl-piperazin-1-yl)-pentylamino]-3-(2-fluoro-6-chloro-3-ethoxy-phenyl)-3,4-dihydro-1H-pyrimido[4,5-d]pyrimidin-2-one;

1-Ethyl-7-[5-(4-methyl-piperazin-1-yl)-pentylamino]-3-(2-difluoro-6-chloro-3-hydoxy-phenyl)-3,4-dihydro-1H-pyrimido[4,5-d]pyrimidin-2-one;

1-Cyclopentyl-7-[5-(4-methyl-piperazin-1-yl)-pentylamino]-3-(2-fluoro-6-chloro-3-hydroxy-5-methoxy phenyl)-3,4-dihydro-1H-pyrimido[4,5-d]pyrimidin-2-one;

1-Cyclopentyl-7-[5-(4-methyl-piperazin-1-yl)-pentylamino]-3-(2-fluoro-6-chloro-3,5-dimethoxy phenyl)-3,4-dihydro-1H-pyrimido[4,5-d]pyrimidin-2-one;

1-Cyclopentyl-7-[5-(4-methyl-piperazin-1-yl)-pentylamino]-3-(2-fluoro-6-chloro-3-methoxy-5-ethoxy phenyl)-3,4-dihydro-1H-pyrimido[4,5-d]pyrimidin-2-one;

1-Cyclopentyl-7-[5-(4-methyl-piperazin-1-yl)-pentylamino]-3-(2-fluoro-6-chloro-3-hydroxy-5-ethoxy phenyl)-3,4-dihydro-1H-pyrimido[4,5-d]pyrimidin-2-one;

1-Cyclopentyl-7-[5-(4-methyl-piperazin-1-yl)-pentylamino]-3-(2-fluoro-6-chloro-3-methoxy-phenyl)-3,4-dihydro-1H-pyrimido[4,5-d]pyrimidin-2-one;

1-Cyclopentyl-7-[5-(4-methyl-piperazin-1-yl)-pentylamino]-3-(2-fluoro-6-chloro-3-ethoxy-phenyl)-3,4-dihydro-1H-pyrimido[4,5-d]pyrimidin-2-one;

1-Cyclopentyl-7-[5-(4-methyl-piperazin-1-yl)-pentylamino]-3-(2-difluoro-6-chloro-3-hydoxy-phenyl)-3,4-dihydro-1H-pyrimido[4,5-d]pyrimidin-2-one;

1-Cyclopropyl-7-[5-(4-methyl-piperazin-1-yl)-pentylamino]-3-(2-fluoro-6-chloro-3-hydroxy-5-methoxy phenyl)-3,4-dihydro-1H-pyrimido[4,5-d]pyrimidin-2-one;

1-Cyclopropyl-7-[5-(4-methyl-piperazin-1-yl)-pentylamino]-3-(2-fluoro-6-chloro-3,5-dimethoxy phenyl)-3,4-dihydro-1H-pyrimido[4,5-d]pyrimidin-2-one;

1-Cyclopropyl-7-[5-(4-methyl-piperazin-1-yl)-pentylamino]-3-(2-fluoro-6-chloro-3-methoxy-5-ethoxy phenyl)-3,4-dihydro-1H-pyrimido[4,5-d]pyrimidin-2-one;

1-Cyclopropyl-7-[5-(4-methyl-piperazin-1-yl)-pentylamino]-3-(2-fluoro-6-chloro-3-hydroxy-5-ethoxy phenyl)-3,4-dihydro-1H-pyrimido[4,5-d]pyrimidin-2-one;

1-Cyclopropyl-7-[5-(4-methyl-piperazin-1-yl)-pentylamino]-3-(2-fluoro-6-chloro-3-methoxy-phenyl)-3,4-dihydro-1H-pyrimido[4,5-d]pyrimidin-2-one;

1-Cyclopropyl-7-[5-(4-methyl-piperazin-1-yl)-pentylamino]-3-(2-fluoro-6-chloro-3-ethoxy-phenyl)-3,4-dihydro-1H-pyrimido[4,5-d]pyrimidin-2-one;

1-Cyclopropyl-7-[5-(4-methyl-piperazin-1-yl)-pentylamino]-3-(2-difluoro-6-chloro-3-hydroxy-phenyl)-3,4-dihydro-1H-pyrimido[4,5-d]pyrimidin-2-one;

1-Ethyl-7-[5-(4-methyl-piperazin-1-yl)-pentylamino]-3-(2-fluoro-6-chloro-3-hydroxy-5-methoxy phenyl)-3,4-dihydro-1H-pyrimido[4,5-d]pyrimidin-2-one;

1-Ethyl-7-[5-(4-methyl-piperazin-1-yl)-pentylamino]-3-(2-fluoro-6-chloro-3,5-dimethoxy phenyl)-3,4-dihydro-1H-pyrimido[4,5-d]pyrimidin-2-one;

1-Ethyl-7-[5-(4-methyl-piperazin-1-yl)-pentylamino]-3-(2-fluoro-6-chloro-3-methoxy-5-ethoxy phenyl)-3,4-dihydro-1H-pyrimido[4,5-d]pyrimidin-2-one;

1-Ethyl-7-[5-(4-methyl-piperazin-1-yl)-pentylamino]-3-(2-fluoro-6-chloro-3-hydroxy-5-ethoxy phenyl)-3,4-dihydro-1H-pyrimido[4,5-d]pyrimidin-2-one;

1-Ethyl-7-[5-(4-methyl-piperazin-1-yl)-pentylamino]-3-(2-fluoro-6-chloro-3-methoxy-phenyl)-3,4-dihydro-1H-pyrimido[4,5-d]pyrimidin-2-one;

1-Ethyl-7-[5-(4-methyl-piperazin-1-yl)-pentylamino]-3-(2-fluoro-6-chloro-3-ethoxy-phenyl)-3,4-dihydro-1H-pyrimido[4,5-d]pyrimidin-2-one;

1-Ethyl-7-[5-(4-methyl-piperazin-1-yl)-pentylamino]-3-(2-difluoro-6-chloro-3-hydroxy-phenyl)-3,4-dihydro-1H-pyrimido[4,5-d]pyrimidin-2-one;

4-[-3-(2,6-Difluoro-3-hydroxy-5-methoxy phenyl)-7-methylamino-2-oxo-3,4-dihydro-2H-pyrimido[4,5-d]pyrimidin-1-yl]-cyclohexanecarboxylic acid;

4-[-3-(2,6-Difluoro-3,5-dimethoxy phenyl)-7-methylamino-2-oxo-3,4-dihydro-2H-pyrimido[4,5-d]pyrimidin-1-yl]-cyclohexanecarboxylic acid;

4-[-3-(2,6-Difluoro-3-methoxy-5-ethoxy phenyl)-7-methylamino-2-oxo-3,4-dihydro-2H-pyrimido[4,5-d]pyrimidin-1-yl]-cyclohexanecarboxylic acid;

4-[-3-(2,6-Difluoro-3-hydroxy-5-ethoxy phenyl)-7-methylamino-2-oxo-3,4-dihydro-2H-pyrimido[4,5-d]pyrimidin-1-yl]-cyclohexanecarboxylic acid;

4-[-3-(2,6-Difluoro-3-methoxy-phenyl)-7-methylamino-2-oxo-3,4-dihydro-2H-pyrimido[4,5-d]pyrimidin-1-yl]-cyclohexanecarboxylic acid;

4-[-3-(2,6-Difluoro-3-ethoxy-phenyl)-7-methylamino-2-oxo-3,4-dihydro-2H-pyrimido[4,5-d]pyrimidin-1-yl]-cyclohexanecarboxylic acid;

4-[-3-(2,6-Difluoro-3-hydroxy-phenyl)-7-methylamino-2-oxo-3,4-dihydro-2H-pyrimido[4,5-d]pyrimidin-1-yl]-cyclohexanecarboxylic acid;

4-[-3-(2-Fluoro-3-hydroxy-5-methoxy phenyl)-7-methylamino-2-oxo-3,4-dihydro-2H-pyrimido[4,5-d]pyrimidin-1-yl]-cyclohexanecarboxylic acid;

4-[-3-(2-Fluoro-3,5-dimethoxy phenyl)-7-methylamino-2-oxo-3,4-dihydro-2H-pyrimido [4,5-d]pyrimidin-1-yl]-cyclohexanecarboxylic acid;

4-[-3-(2-Fluoro-3-methoxy-5-ethoxy phenyl)-7-methylamino-2-oxo-3,4-dihydro-2H-pyrimido[4,5-d]pyrimidin-1-yl]-cyclohexanecarboxylic acid;

4-[-3-(2-Fluoro-3-hydroxy-5-ethoxy phenyl)-7-methylamino-2-oxo-3,4-dihydro-2H-pyrimido[4,5-d]pyrimidin-1-yl]-cyclohexanecarboxylic acid;

4-[-3-(2-Fluoro-3-methoxy-phenyl)-7-methylamino-2-oxo-3,4-dihydro-2H-pyrimido[4,5-d]pyrimidin-1-yl]-cyclohexanecarboxylic acid;

4-[-3-(2-Fluoro-3-ethoxy-phenyl)-7-methylamino-2-oxo-3,4-dihydro-2H-pyrimido[4,5-d]pyrimidin-1-yl]-cyclohexanecarboxylic acid;

4-[-3-(2-Difluoro-3-hydroxy-phenyl)-7-methylamino-2-oxo-3,4-dihydro-2H-pyrimido[4,5-d]pyrimidin-1-yl]-cyclohexanecarboxylic acid;

4-[-3-(2-Fluoro-6-chloro-3-hydroxy-5-methoxy phenyl)-7-methylamino-2-oxo-3,4-dihydro-2H-pyrimido[4,5-d]pyrimidin-1-yl]-cyclohexanecarboxylic acid;

4-[-3-(2-Fluoro-6-chloro-3,5-dimethoxy phenyl)-7-methylamino-2-oxo-3,4-dihydro-2H-pyrimido[4,5-d]pyrimidin-1-yl]-cyclohexanecarboxylic acid;

4-[-3-(2-Fluoro-6-chloro-3-methoxy-5-ethoxy phenyl)-7-methylamino-2-oxo-3,4-dihydro-2H-pyrimido[4,5-d]pyrimidin-1-yl]-cyclohexanecarboxylic acid;

4-[-3-(2-Fluoro-6-chloro-3-hydroxy-5-ethoxy phenyl)-7-methylamino-2-oxo-3,4-dihydro-2H-pyrimido[4,5-d]pyrimidin-1-yl]-cyclohexanecarboxylic acid;

4-[-3-(2-Fluoro-6-chloro-3-methoxy-phenyl)-7-methylamino-2-oxo-3,4-dihydro-2H-pyrimido[4,5-d]pyrimidin-1-yl]-cyclohexanecarboxylic acid;

4-[-3-(2-Fluoro-6-chloro-3-ethoxy-phenyl)-7-methylamino-2-oxo-3,4-dihydro-2H-pyrimido[4,5-d]pyrimidin-1-yl]-cyclohexanecarboxylic acid;

4-[-3-(2-Difluoro-6-chloro-3-hydroxy-phenyl)-7-methylamino-2-oxo-3,4-dihydro-2H-pyrimido[4,5-d]pyrimidin-1-yl]-cyclohexanecarboxylic acid;

1-Cyclopentyl-7-(5-diisopropylamino-pentylamino)-3-(2,6-difluoro-3-hydroxy-5-methoxy phenyl)-3,4-dihydro-1H-pyrimido[4,5-d]pyrimidin-2-one;

1-Cyclopentyl-7-(5-diisopropylamino-pentylamino)-3-(2,6-difluoro-3,5-dimethoxy phenyl)-3,4-dihydro-1H-pyrimido[4,5-d]pyrimidin-2-one;

1-Cyclopentyl-7-(5-diisopropylamino-pentylamino)-3-(2,6-difluoro-3-methoxy-5-ethoxy phenyl)-3,4-dihydro-1H-pyrimido[4,5-d]pyrimidin-2-one;

1-Cyclopentyl-7-(5-diisopropylamino-pentylamino)-3-(2,6-difluoro-3-hydroxy-5-ethoxy phenyl)-3,4-dihydro-1H-pyrimido[4,5-d]pyrimidin-2-one;

1-Cyclopentyl-7-(5-diisopropylamino-pentylamino)-3-(2,6-difluoro-3-methoxy-phenyl)-3,4-dihydro-1H-pyrimido[4,5-d]pyrimidin-2-one;

1-Cyclopentyl-7-(5-diisopropylamino-pentylamino)-3-(2,6-difluoro-3-ethoxy-phenyl)-3,4-dihydro-1H-pyrimido[4,5-d]pyrimidin-2-one;

1-Cyclopentyl-7-(5-diisopropylamino-pentylamino)-3-(2,6-difluoro-3-hydroxy-phenyl)-3,4-dihydro-1H-pyrimido[4,5-d]pyrimidin-2-one;

1-Cyclopropyl-7-(5-diisopropylamino-pentylamino)-3-(2,6-difluoro-3-hydroxy-5-methoxy phenyl)-3,4-dihydro-1H-pyrimido[4,5-d]pyrimidin-2-one;

1-Cyclopropyl-7-(5-diisopropylamino-pentylamino)-3-(2,6-difluoro-3,5-dimethoxy phenyl)-3,4-dihydro-1H-pyrimido[4,5-d]pyrimidin-2-one;

1-Cyclopropyl-7-(5-diisopropylamino-pentylamino)-3-(2,6-difluoro-3-methoxy-5-ethoxy phenyl)-3,4-dihydro-1H-pyrimido[4,5-d]pyrimidin-2-one;

1-Cyclopropyl-7-(5-diisopropylamino-pentylamino)-3-(2,6-difluoro-3-hydroxy-5-ethoxy phenyl)-3,4-dihydro-1H-pyrimido[4,5-d]pyrimidin-2-one;

1-Cyclopropyl-7-(5-diisopropylamino-pentylamino)-3-(2,6-difluoro-3-methoxy-phenyl)-3,4-dihydro-1H-pyrimido[4,5-d]pyrimidin-2-one;

1-Cyclopropyl-7-(5-diisopropylamino-pentylamino)-3-(2,6-difluoro-3-ethoxy-phenyl)-3,4-dihydro-1H-pyrimido[4,5-d]pyrimidin-2-one;

1-Cyclopropyl-7-(5-diisopropylamino-pentylamino)-3-(2,6-difluoro-3-hydroxy-phenyl)-3,4-dihydro-1H-pyrimido[4,5-d]pyrimidin-2-one;

1-Ethyl-7-(5-diisopropylamino-pentylamino)-3-(2,6-difluoro-3-hydroxy-5-methoxy phenyl)-3,4-dihydro-1H-pyrimido[4,5-d]pyrimidin-2-one;

1-Ethyl-7-(5-diisopropylamino-pentylamino)-3-(2,6-difluoro-3,5-dimethoxy phenyl)-3,4-dihydro-1H-pyrimido[4,5-d]pyrimidin-2-one;

1-Ethyl-7-(5-diisopropylamino-pentylamino)-3-(2,6-difluoro-3-methoxy-5-ethoxy phenyl)-3,4-dihydro-1H-pyrimido[4,5-d]pyrimidin-2-one;

1-Ethyl-7-(5-diisopropylamino-pentylamino)-3-(2,6-difluoro-3-hydroxy-5-ethoxy phenyl)-3,4-dihydro-1H-pyrimido[4,5-d]pyrimidin-2-one;

1-Ethyl-7-(5-diisopropylamino-pentylamino)-3-(2,6-difluoro-3-methoxy-phenyl)-3,4-dihydro-1H-pyrimido[4,5-d]pyrimidin-2-one;

1-Ethyl-7-(5-diisopropylamino-pentylamino)-3-(2,6-difluoro-3-ethoxy-phenyl)-3,4-dihydro-1H-pyrimido[4,5-d]pyrimidin-2-one;

1-Ethyl-7-(5-diisopropylamino-pentylamino)-3-(2,6-difluoro-3-hydroxy-phenyl)-3,4-dihydro-1H-pyrimido[4,5-d]pyrimidin-2-one;

1-Cyclopentyl-7-(5-diisopropylamino-pentylamino)-3-(2-fluoro-3-hydroxy-5-methoxy phenyl)-3,4-dihydro-1H-pyrimido[4,5-d]pyrimidin-2-one;

1-Cyclopentyl-7-(5-diisopropylamino-pentylamino)-3-(2-fluoro-3,5-dimethoxy phenyl)-3,4-dihydro-1H-pyrimido[4,5-d]pyrimidin-2-one;

1-Cyclopentyl-7-(5-diisopropylamino-pentylamino)-3-(2-fluoro-3-methoxy-5-ethoxy phenyl)-3,4-dihydro-1H-pyrimido[4,5-d]pyrimidin-2-one;

1-Cyclopentyl-7-(5-diisopropylamino-pentylamino)-3-(2-fluoro-3-hydroxy-5-ethoxy phenyl)-3,4-dihydro-1H-pyrimido[4,5-d]pyrimidin-2-one;

1-Cyclopentyl-7-(5-diisopropylamino-pentylamino)-3-(2-fluoro-3-methoxy-phenyl)-3,4-dihydro-1H-pyrimido[4,5-d]pyrimidin-2-one;

1-Cyclopentyl-7-(5-diisopropylamino-pentylamino)-3-(2-fluoro-3-ethoxy-phenyl)-3,4-dihydro-1H-pyrimido[4,5-d]pyrimidin-2-one;

1-Cyclopentyl-7-(5-diisopropylamino-pentylamino)-3-(2-difluoro-3-hydroxy-phenyl)-3,4-dihydro-1H-pyrimido[4,5-d]pyrimidin-2-one;

1-Cyclopropyl-7-(5-diisopropylamino-pentylamino)-3-(2-fluoro-3-hydroxy-5-methoxy phenyl)-3,4-dihydro-1H-pyrimido[4,5-d]pyrimidin-2-one;

1-Cyclopropyl-7-(5-diisopropylamino-pentylamino)-3-(2-fluoro-3,5-dimethoxy phenyl)-3,4-dihydro-1H-pyrimido[4,5-d]pyrimidin-2-one;

1-Cyclopropyl-7-(5-diisopropylamino-pentylamino)-3-(2-fluoro-3-methoxy-5-ethoxy phenyl)-3,4-dihydro-1H-pyrimido[4,5-d]pyrimidin-2-one;

1-Cyclopropyl-7-(5-diisopropylamino-pentylamino)-3-(2-fluoro-3-hydroxy-5-ethoxy phenyl)-3,4-dihydro-1H-pyrimido[4,5-d]pyrimidin-2-one;

1-Cyclopropyl-7-(5-diisopropylamino-pentylamino)-3-(2-fluoro-3-methoxy-phenyl)-3,4-dihydro-1H-pyrimido[4,5-d]pyrimidin-2-one;

1-Cyclopropyl-7-(5-diisopropylamino-pentylamino)-3-(2-fluoro-3-ethoxy-phenyl)-3,4-dihydro-1H-pyrimido[4,5-d]pyrimidin-2-one;

1-Cyclopropyl-7-(5-diisopropylamino-pentylamino)-3-(2-difluoro-3-hydroxy-phenyl)-3,4-dihydro-1H-pyrimido[4,5-d]pyrimidin-2-one;

1-Ethyl-7-(5-diisopropylamino-pentylamino)-3-(2-fluoro-3-hydroxy-5-methoxy phenyl)-3,4-dihydro-1H-pyrimido[4,5-d]pyrimidin-2-one;

1-Ethyl-7-(5-diisopropylamino-pentylamino)-3-(2-fluoro-3,5-dimethoxy phenyl)-3,4-dihydro-1H-pyrimido[4,5-d]pyrimidin-2-one;

1-Ethyl-7-(5-diisopropylamino-pentylamino)-3-(2-fluoro-3-methoxy-5-ethoxy phenyl)-3,4-dihydro-1H-pyrimido[4,5-d]pyrimidin-2-one;

1-Ethyl-7-(5-diisopropylamino-pentylamino)-3-(2-fluoro-3-hydroxy-5-ethoxy phenyl)-3,4-dihydro-1H-pyrimido[4,5-d]pyrimidin-2-one;

1-Ethyl-7-(5-diisopropylamino-pentylamino)-3-(2-fluoro-3-methoxy-phenyl)-3,4-dihydro-1H-pyrimido[4,5-d]pyrimidin-2-one;

1-Ethyl-7-(5-diisopropylamino-pentylamino)-3-(2-fluoro-3-ethoxy-phenyl)-3,4-dihydro-1H-pyrimido[4,5-d]pyrimidin-2-one;

1-Ethyl-7-(5-diisopropylamino-pentylamino)-3-(2-difluoro-3-hydroxy-phenyl)-3,4-dihydro-1H-pyrimido[4,5-d]pyrimidin-2-one;

1-Cyclopentyl-7-(5-diisopropylamino-pentylamino)-3-(2-fluoro-6-chloro-3-hydroxy-5-methoxy phenyl)-3,4-dihydro-1H-pyrimido[4,5-d]pyrimidin-2-one;

1-Cyclopentyl-7-(5-diisopropylamino-pentylamino)-3-(2-fluoro-6-chloro-3,5-dimethoxy phenyl)-3,4-dihydro-1H-pyrimido[4,5-d]pyrimidin-2-one;

1-Cyclopentyl-7-(5-diisopropylamino-pentylamino)-3-(2-fluoro-6-chloro-3-methoxy-5-ethoxy phenyl)-3,4-dihydro-1H-pyrimido[4,5-d]pyrimidin-2-one;

1-Cyclopentyl-7-(5-diisopropylamino-pentylamino)-3-(2-fluoro-6-chloro-3-hydroxy-5-ethoxy phenyl)-3,4-dihydro-1H-pyrimido[4,5-d]pyrimidin-2-one;

1-Cyclopentyl-7-(5-diisopropylamino-pentylamino)-3-(2-fluoro-6-chloro-3-methoxy-phenyl)-3,4-dihydro-1H-pyrimido[4,5-d]pyrimidin-2-one;

1-Cyclopentyl-7-(5-diisopropylamino-pentylamino)-3-(2-fluoro-6-chloro-3-ethoxy-phenyl)-3,4-dihydro-1H-pyrimido[4,5-d]pyrimidin-2-one;

1-Cyclopentyl-7-(5-diisopropylamino-pentylamino)-3-(2-difluoro-6-chloro-3-hydoxy-phenyl)-3,4-dihydro-1H-pyrimido[4,5-d]pyrimidin-2-one;

1-Cyclopropyl-7-(5-diisopropylamino-pentylamino)-3-(2-fluoro-6-chloro-3-hydroxy-5-methoxy phenyl)-3,4-dihydro-1H-pyrimido[4,5-d]pyrimidin-2-one;

1-Cyclopropyl-7-(5-diisopropylamino-pentylamino)-3-(2-fluoro-6-chloro-3,5-dimethoxy phenyl)-3,4-dihydro-1H-pyrimido[4,5-d]pyrimidin-2-one;

1-Cyclopropyl-7-(5-diisopropylamino-pentylamino)-3-(2-fluoro-6-chloro-3-methoxy-5-ethoxy phenyl)-3,4-dihydro-1H-pyrimido[4,5-d]pyrimidin-2-one;

1-Cyclopropyl-7-(5-diisopropylamino-pentylamino)-3-(2-fluoro-6-chloro-3-hydroxy-5-ethoxy phenyl)-3,4-dihydro-1H-pyrimido[4,5-d]pyrimidin-2-one;

1-Cyclopropyl-7-(5-diisopropylamino-pentylamino)-3-(2-fluoro-6-chloro-3-methoxy-phenyl)-3,4-dihydro-1H-pyrimido[4,5-d]pyrimidin-2-one;

1-Cyclopropyl-7-(5-diisopropylamino-pentylamino)-3-(2-fluoro-6-chloro-3-ethoxy-phenyl)-3,4-dihydro-1H-pyrimido[4,5-d]pyrimidin-2-one;

1-Cyclopropyl-7-(5-diisopropylamino-pentylamino)-3-(2-difluoro-6-chloro-3-hydoxy-phenyl)-3,4-dihydro-1H-pyrimido[4,5-d]pyrimidin-2-one;

1-Ethyl-7-(5-diisopropylamino-pentylamino)-3-(2-fluoro-6-chloro-3-hydroxy-5-methoxy phenyl)-3,4-dihydro-1H-pyrimido[4,5-d]pyrimidin-2-one;

1-Ethyl-7-(5-diisopropylamino-pentylamino)-3-(2-fluoro-6-chloro-3,5-dimethoxy phenyl)-3,4-dihydro-1H-pyrimido[4,5-d]pyrimidin-2-one;

1-Ethyl-7-(5-diisopropylamino-pentylamino)-3-(2-fluoro-6-chloro-3-methoxy-5-ethoxy phenyl)-3,4-dihydro-1H-pyrimido[4,5-d]pyrimidin-2-one;

1-Ethyl-7-(5-diisopropylamino-pentylamino)-3-(2-fluoro-6-chloro-3-hydroxy-5-ethoxy phenyl)-3,4-dihydro-1H-pyrimido[4,5-d]pyrimidin-2-one;

1-Ethyl-7-(5-diisopropylamino-pentylamino)-3-(2-fluoro-6-chloro-3-methoxy-phenyl)-3,4-dihydro-1H-pyrimido[4,5-d]pyrimidin-2-one;

1-Ethyl-7-(5-diisopropylamino-pentylamino)-3-(2-fluoro-6-chloro-3-ethoxy-phenyl)-3,4-dihydro-1H-pyrimido[4,5-d]pyrimidin-2-one;

1-Ethyl-7-(5-diisopropylamino-pentylamino)-3-(2-difluoro-6-chloro-3-hydroxy-phenyl)-3,4-dihydro-1H-pyrimido[4,5-d]pyrimidin-2-one;

1-Cyclopentyl-7-(4-amino-cyclohexylamino)-3-(2,6-difluoro-3-hydroxy-5-methoxy phenyl)-3,4-dihydro-1H-pyrimido[4,5-d]pyrimidin-2-one;

1-Cyclopentyl-7-(4-amino-cyclohexylamino)-3-(2,6-difluoro-3,5-dimethoxy phenyl)-3,4-dihydro-1H-pyrimido[4,5-d]pyrimidin-2-one;

1-Cyclopentyl-7-(4-amino-cyclohexylamino)-3-(2,6-difluoro-3-methoxy-5-ethoxy phenyl)-3,4-dihydro-1H-pyrimido[4,5-d]pyrimidin-2-one;

1-Cyclopentyl-7-(4-amino-cyclohexylamino)-3-(2,6-difluoro-3-hydroxy-5-ethoxy phenyl)-3,4-dihydro-1H-pyrimido[4,5-d]pyrimidin-2-one;

1-Cyclopentyl-7-(4-amino-cyclohexylamino)-3-(2,6-difluoro-3-methoxy-phenyl)-3,4-dihydro-1H-pyrimido[4,5-d]pyrimidin-2-one;

1-Cyclopentyl-7-(4-amino-cyclohexylamino)-3-(2,6-difluoro-3-ethoxy-phenyl)-3,4-dihydro-1H-pyrimido[4,5-d]pyrimidin-2-one;

1-Cyclopentyl-7-(4-amino-cyclohexylamino)-3-(2,6-difluoro-3-hydroxy-phenyl)-3,4-dihydro-1H-pyrimido[4,5-d]pyrimidin-2-one;

1-Cyclopropyl-7-(4-amino-cyclohexylamino)-3-(2,6-difluoro-3-hydroxy-5-methoxy phenyl)-3,4-dihydro-1H-pyrimido[4,5-d]pyrimidin-2-one;

1-Cyclopropyl-7-(4-amino-cyclohexylamino)-3-(2,6-difluoro-3,5-dimethoxy phenyl)-3,4-dihydro-1H-pyrimido[4,5-d]pyrimidin-2-one;

1-Cyclopropyl-7-(4-amino-cyclohexylamino)-3-(2,6-difluoro-3-methoxy-5-ethoxy phenyl)-3,4-dihydro-1H-pyrimido[4,5-d]pyrimidin-2-one;

1-Cyclopropyl-7-(4-amino-cyclohexylamino)-3-(2,6-difluoro-3-hydroxy-5-ethoxy phenyl)-3,4-dihydro-1H-pyrimido[4,5-d]pyrimidin-2-one;

1-Cyclopropyl-7-(4-amino-cyclohexylamino)-3-(2,6-difluoro-3-methoxy-phenyl)-3,4-dihydro-1H-pyrimido[4,5-d]pyrimidin-2-one;

1-Cyclopropyl-7-(4-amino-cyclohexylamino)-3-(2,6-difluoro-3-ethoxy-phenyl)-3,4-dihydro-1H-pyrimido[4,5-d]pyrimidin-2-one;

1-Cyclopropyl-7-(4-amino-cyclohexylamino)-3-(2,6-difluoro-3-hydroxy-phenyl)-3,4-dihydro-1H-pyrimido[4,5-d]pyrimidin-2-one;

1-Ethyl-7-(4-amino-cyclohexylamino)-3-(2,6-difluoro-3-hydroxy-5-methoxy phenyl)-3,4-dihydro-1H-pyrimido[4,5-d]pyrimidin-2-one;

1-Ethyl-7-(4-amino-cyclohexylamino)-3-(2,6-difluoro-3,5-dimethoxy phenyl)-3,4-dihydro-1H-pyrimido[4,5-d]pyrimidin-2-one;

1-Ethyl-7-(4-amino-cyclohexylamino)-3-(2,6-difluoro-3-methoxy-5-ethoxy phenyl)-3,4-dihydro-1H-pyrimido[4,5-d]pyrimidin-2-one;

1-Ethyl-7-(4-amino-cyclohexylamino)-3-(2,6-difluoro-3-hydroxy-5-ethoxy phenyl)-3,4-dihydro-1H-pyrimido[4,5-d]pyrimidin-2-one;

1-Ethyl-7-(4-amino-cyclohexylamino)-3-(2,6-difluoro-3-methoxy-phenyl)-3,4-dihydro-1H-pyrimido[4,5-d]pyrimidin-2-one;

1-Ethyl-7-(4-amino-cyclohexylamino)-3-(2,6-difluoro-3-ethoxy-phenyl)-3,4-dihydro-1H-pyrimido[4,5-d]pyrimidin-2-one;

1-Ethyl-7-(4-amino-cyclohexylamino)-3-(2,6-difluoro-3-hydoxy-phenyl)-3,4-dihydro-1H-pyrimido[4,5-d]pyrimidin-2-one;

1-Cyclopentyl-7-(4-amino-cyclohexylamino)-3-(2-fluoro-3-hydroxy-5-methoxy phenyl)-3,4-dihydro-1H-pyrimido[4,5-d]pyrimidin-2-one;

1-Cyclopentyl-7-(4-amino-cyclohexylamino)-3-(2-fluoro-3,5-dimethoxy phenyl)-3,4-dihydro-1H-pyrimido[4,5-d]pyrimidin-2-one;

1-Cyclopentyl-7-(4-amino-cyclohexylamino)-3-(2-fluoro-3-methoxy-5-ethoxy phenyl)-3,4-dihydro-1H-pyrimido[4,5-d]pyrimidin-2-one;

1-Cyclopentyl-7-(4-amino-cyclohexylamino)-3-(2-fluoro-3-hydroxy-5-ethoxy phenyl)-3,4-dihydro-1H-pyrimido[4,5-d]pyrimidin-2-one;

1-Cyclopentyl-7-(4-amino-cyclohexylamino)-3-(2-fluoro-3-methoxy-phenyl)-3,4-dihydro-1H-pyrimido[4,5-d]pyrimidin-2-one;

1-Cyclopentyl-7-(4-amino-cyclohexylamino)-3-(2-fluoro-3-ethoxy-phenyl)-3,4-dihydro-1H-pyrimido[4,5-d]pyrimidin-2-one;

1-Cyclopentyl-7-(4-amino-cyclohexylamino)-3-(2-difluoro-3-hydroxy-phenyl)-3,4-dihydro-1H-pyrimido[4,5-d]pyrimidin-2-one;

1-Cyclopropyl-7-(4-amino-cyclohexylamino)-3-(2-fluoro-3-hydroxy-5-methoxy phenyl)-3,4-dihydro-1H-pyrimido[4,5-d]pyrimidin-2-one;

1-Cyclopropyl-7-(4-amino-cyclohexylamino)-3-(2-fluoro-3,5-dimethoxy phenyl)-3,4-dihydro-1H-pyrimido[4,5-d]pyrimidin-2-one;

1-Cyclopropyl-7-(4-amino-cyclohexylamino)-3-(2-fluoro-3-methoxy-5-ethoxy phenyl)-3,4-dihydro-1H-pyrimido[4,5-d]pyrimidin-2-one;

1-Cyclopropyl-7-(4-amino-cyclohexylamino)-3-(2-fluoro-3-hydroxy-5-ethoxy phenyl)-3,4-dihydro-1H-pyrimido[4,5-d]pyrimidin-2-one;

1-Cyclopropyl-7-(4-amino-cyclohexylamino)-3-(2-fluoro-3-methoxy-phenyl)-3,4-dihydro-1H-pyrimido[4,5-d]pyrimidin-2-one;

1-Cyclopropyl-7-(4-amino-cyclohexylamino)-3-(2-fluoro-3-ethoxy-phenyl)-3,4-dihydro-1H-pyrimido[4,5-d]pyrimidin-2-one;

1-Cyclopropyl-7-(4-amino-cyclohexylamino)-3-(2-difluoro-3-hydroxy-phenyl)-3,4-dihydro-1H-pyrimido[4,5-d]pyrimidin-2-one;

1-Ethyl-7-(4-amino-cyclohexylamino)-3-(2-fluoro-3-hydroxy-5-methoxy phenyl)-3,4-dihydro-1H-pyrimido[4,5-d]pyrimidin-2-one;

1-Ethyl-7-(4-amino-cyclohexylamino)-3-(2-fluoro-3,5-dimethoxy phenyl)-3,4-dihydro-1H-pyrimido[4,5-d]pyrimidin-2-one;

1-Ethyl-7-(4-amino-cyclohexylamino)-3-(2-fluoro-3-methoxy-5-ethoxy phenyl)-3,4-dihydro-1H-pyrimido[4,5-d]pyrimidin-2-one;

1-Ethyl-7-(4-amino-cyclohexylamino)-3-(2-fluoro-3-hydroxy-5-ethoxy phenyl)-3,4-dihydro-1H-pyrimido[4,5-d]pyrimidin-2-one;

1-Ethyl-7-(4-amino-cyclohexylamino)-3-(2-fluoro-3-methoxy-phenyl)-3,4-dihydro-1H-pyrimido[4,5-d]pyrimidin-2-one;

1-Ethyl-7-(4-amino-cyclohexylamino)-3-(2-fluoro-3-ethoxy-phenyl)-3,4-dihydro-1H-pyrimido[4,5-d]pyrimidin-2-one;

1-Ethyl-7-(4-amino-cyclohexylamino)-3-(2-difluoro-3-hydroxy-phenyl)-3,4-dihydro-1H-pyrimido[4,5-d]pyrimidin-2-one;

1-Cyclopentyl-7-(4-amino-cyclohexylamino)-3-(2-fluoro-6-chloro-3-hydroxy-5-methoxy phenyl)-3,4-dihydro-1H-pyrimido[4,5-d]pyrimidin-2-one;

1-Cyclopentyl-7-(4-amino-cyclohexylamino)-3-(2-fluoro-6-chloro-3,5-dimethoxy phenyl)-3,4-dihydro-1H-pyrimido[4,5-d]pyrimidin-2-one;

1-Cyclopentyl-7-(4-amino-cyclohexylamino)-3-(2-fluoro-6-chloro-3-methoxy-5-ethoxy phenyl)-3,4-dihydro-1H-pyrimido[4,5-d]pyrimidin-2-one;

1-Cyclopentyl-7-(4-amino-cyclohexylamino)-3-(2-fluoro-6-chloro-3-hydroxy-5-ethoxy phenyl)-3,4-dihydro-1H-pyrimido[4,5-d]pyrimidin-2-one;

1-Cyclopentyl-7-(4-amino-cyclohexylamino)-3-(2-fluoro-6-chloro-3-methoxy-phenyl)-3,4-dihydro-1H-pyrimido[4,5-d]pyrimidin-2-one;

1-Cyclopentyl-7-(4-amino-cyclohexylamino)-3-(2-fluoro-6-chloro-3-ethoxy-phenyl)-3,4-dihydro-1H-pyrimido[4,5-d]pyrimidin-2-one;

1-Cyclopentyl-7-(4-amino-cyclohexylamino)-3-(2-difluoro-6-chloro-3-hydroxy-phenyl)-3,4-dihydro-1H-pyrimido[4,5-d]pyrimidin-2-one;

1-Cyclopropyl-7-(4-amino-cyclohexylamino)-3-(2-fluoro-6-chloro-3-hydroxy-5-methoxy phenyl)-3,4-dihydro-1H-pyrimido[4,5-d]pyrimidin-2-one;

1-Cyclopropyl-7-(4-amino-cyclohexylamino)-3-(2-fluoro-6-chloro-3,5-dimethoxy phenyl)-3,4-dihydro-1H-pyrimido[4,5-d]pyrimidin-2-one;

1-Cyclopropyl-7-(4-amino-cyclohexylamino)-3-(2-fluoro-6-chloro-3-methoxy-5-ethoxy phenyl)-3,4-dihydro-1H-pyrimido[4,5-d]pyrimidin-2-one;

1-Cyclopropyl-7-(4-amino-cyclohexylamino)-3-(2-fluoro-6-chloro-3-hydroxy-5-ethoxy phenyl)-3,4-dihydro-1H-pyrimido[4,5-d]pyrimidin-2-one;

1-Cyclopropyl-7-(4-amino-cyclohexylamino)-3-(2-fluoro-6-chloro-3-methoxy-phenyl)-3,4-dihydro-1H-pyrimido[4,5-d]pyrimidin-2-one;

1-Cyclopropyl-7-(4-amino-cyclohexylamino)-3-(2-fluoro-6-chloro-3-ethoxy-phenyl)-3,4-dihydro-1H-pyrimido[4,5-d]pyrimidin-2-one;

1-Cyclopropyl-7-(4-amino-cyclohexylamino)-3-(2-difluoro-6-chloro-3-hydroxy-phenyl)-3,4-dihydro-1H-pyrimido[4,5-d]pyrimidin-2-one;

1-Ethyl-7-(4-amino-cyclohexylamino)-3-(2-fluoro-6-chloro-3-hydroxy-5-methoxy phenyl)-3,4-dihydro-1H-pyrimido[4,5-d]pyrimidin-2-one;

1-Ethyl-7-(4-amino-cyclohexylamino)-3-(2-fluoro-6-chloro-3,5-dimethoxy phenyl)-3,4-dihydro-1 H-pyrimido[4,5-d]pyrimidin-2-one;

1-Ethyl-7-(4-amino-cyclohexylamino)-3-(2-fluoro-6-chloro-3-methoxy-5-ethoxy phenyl)-3,4-dihydro-1H-pyrimido[4,5-d]pyrimidin-2-one;

1-Ethyl-7-(4-amino-cyclohexylamino)-3-(2-fluoro-6-chloro-3-hydroxy-5-ethoxy phenyl)-3,4-dihydro-1H-pyrimido[4,5-d]pyrimidin-2-one;

1-Ethyl-7-(4-amino-cyclohexylamino)-3-(2-fluoro-6-chloro-3-methoxy-phenyl)-3,4-dihydro-1H-pyrimido[4,5-d]pyrimidin-2-one;

1-Ethyl-7-(4-amino-cyclohexylamino)-3-(2-fluoro-6-chloro-3-ethoxy-phenyl)-3,4-dihydro-1H-pyrimido[4,5-d]pyrimidin-2-one; and 1-Ethyl-7-(4-amino-cyclohexylamino)-3-(2-difluoro-6-chloro-3-hydroxy-phenyl)-3,4-dihydro-1H-pyrimido[4,5-d]pyrimidin-2-one;

as well as the pharmaceutically acceptable salt and ester forms thereof.

This invention also provides pharmaceutical formulations comprising a compound of Formula I together with a pharmaceutically acceptable carrier, diluent, or excipient therefore.

Compounds within the scope of the present invention are inhibitors of the cyclin-dependent kinases such as cdk2, cdc2, and cdk4. Some of the compounds of the present invention also inhibit growth factor mediated tyrosine kinases including those of platelet-derived growth factor (PDGF), fibroblast growth factor (FGF), and epidermal growth factor (EGF), as well as non-receptor tyrosine kinases such as c-Src. As inhibitors of cyclin-dependent, as well as growth factor-mediated and non-receptor tyrosine kinases, the compounds of the instant invention are useful in treating, inhibiting, controlling or slowing progression of excessive cellular proliferation and proliferative disorders, also known as hyperproliferative disorders, such as cancer, psoriasis, vascular smooth muscle cell proliferation associated with atherosclerosis, benign prostate hyperplasia, familial adenomatosis polyposis, neuro-fibromatosis, pulmonary fibrosis, arthritis glomerulonephritis, diabetic retinopathy, neovascular glaucoma or other ocular angiogenic disorders, such as retinopathy of prematurity (retrolental fibroplastic retinopathies) and angiogenesis, and post-surgical vascular stenosis and restenosis in mammals. The compounds of this invention may also be used in the treatment, inhibition, modulation or amelioration of autoimmune disorders associated with inappropriate protein tyrosine kinase activity, including multiple sclerosis, rheumatoid arthritis, including pannus formation in those experiencing rheumatoid arthritis, and systemic erythematosus. The compounds of this invention is also useful in regimens for inhibiting tyrosine kinase activity associated with osteoporosis or conditions of excessive osteoclastic bone resorption, and in diseases wherein cells receive pro-inflammatory signals, such as inflammatory bowel disease, pancreatitis and asthma.

Cancers which may be inhibited, treated or controlled with the compounds, methods and pharmaceutical formulations herein include, but are not limited to, cancers of the breast, prostate, testicular, lung, ovarian, uterine, bladder, colon, rectum, stomach, pancreatic, hepatic, melanoma, esophageal, brain, Kaposi's sarcoma, squamous cell carcinomas, leukemias, gliomas, and lymphomas.

A further embodiment of this invention is a method of treating subjects suffering from diseases caused by cellular proliferation. The method entails inhibiting proliferation of tumorigenic cells of epithelial origin and vascular smooth muscle proliferation, and/or cellular migration by administering an effective amount of a compound of Formula I to a subject in need of treatment.

A further embodiment of this invention is a method of treating subjects suffering from diseases caused by DNA tumor viruses such as herpes viruses.

The compounds of this invention may also be used in therapeutic combinations with other inhibitors of cyclin-dependent kinases (CDK). These include synthetic CDK inhibitors, such as purines, alkaloids, indirubins, flavonoids, paullones, butyrolactone I, and hymenialdisine.

Examples of purines which may be used in pharmaceutical combinations and regimens of this invention include olomoucine, roscovitine, CVT-313, isopentyl-adenine, purvalanol B, and 6-Cyclohexylmethoxy-9H-purin-2-ylamine, also known as NU-2058. Useful alkaloid CDK inhibitors include staurosporine, UCN-01 and CPG 41 251. Indirubins include indirubin and analogues, including indirubin-5-sulphonic acid, 5-chloro-indirubin, and indirubin-3'-monoxime. Useful Flavonoids include flavopiridol, its deschloro derivative, L86–8276, and thioflavopiridol. Also useful is genistein, a naturally occurring isoflavone.

The compounds herein may also be used in drug regimens with taxanes, such as paclitaxel and docetaxel.

For indications in treating bladder cancer, compounds herein may be used in regimens with agents such as PACIS® (BCG, live—BioChem Pharma Inc.) and VALSTAR® (valrubicin—Anthra Pharmaceuticals). Brain cancer, including recurrent glioblastoma multiforme, combinations may include GLIADEL® (carmustine wafer for implantation), sponsored by Guilford Pharmaceuticals Inc.

Breast cancer drugs which may be used in combinations of this invention include ADRIAMYCIN® (doxorubicin); AREDIA® (pamidronate disodium for injection—Ciba Geigy Corporation Pharmaceuticals Division); ARIMIDEX® (anastrozole—AstraZeneca Pharmaceuticals); AROMASIN® (exemestane—Pharmacia & Upjohn Company; CYTOXAN® (cyclophosphamide); ELLENCE® (epirubicin hydrochloride—Pharmacia & Upjohn); FARESTON® (toremifene citrate—Orion Corporation); FEMARA® (letrozole—Novartis Pharmaceuticals Company); GEMZAR® (gemcitabine); HERCEPTIN® (trastuzumab—Genentech, Inc.); MEGACE® (megestrol acetate); NAVELBINE® (vinorelbine); NOLVADEX® (tamoxifen citrate—AstraZeneca Pharmaceuticals); TAXOL® (paclitaxel—Bristol-Myers Squibb); TAXOTERE® (docetaxel—Aventis, Inc.); XELODA® (capecitabine—Roche); and ZOLADEX® (goserelin acetate).

The compounds of this invention can also be used in advance of, in combination with, or following chemotherapy combinations or regimens known in the art. Examples of chemotherapy combinations utilized in treatment or inhibition of breast cancer include cyclophosphamide (CYTOXAN®); methotrexate (AMETHOPTERIN®, MEXATE®, or FOLEX®); and fluorouracil (Fluorouracil, 5-Fu, OR ADRUCIL®). This combination therapy is often called "CMF". Another related regimen is the administration of doxorubicin (ADRIAMYCIN®), followed by the "CMF" therapy. The regimen referred to as "CAF" comprises combinations of cyclophosphamide, doxorubicin, and fluorouracil. Combinations of doxorubicin (ADRIAMYCIN®) and cyclophosphamide are called "AC". Another conventional therapeutic breast cancer combination is the AC regiment, doxorubicin (ADRIAMYCIN®) and cyclophosphamide, combined with paclitaxel (TAXOL®). Another conventional regimen of treatment is the combination of cyclophosphamide (CYTOXAN®), epirubicin (ELLENCE(®) and fluorouracil.

Combination therapies for colon and rectal cancer may include an effective amount of a compound of this invention and CAMPTOSAR® (irinotecan hydrochloride) injection, available from Pharmacia & Upjohn.

Head and neck cancers, including moderate to severe xerostomia, may be treated with a compound of this invention and ETHYOL® (amifostine) for Injection, available from US Bioscience. Regimens for treatment or amelioration of Kaposi's Sarcoma include compounds of this invention and PANRETIN® (Alitretinoin gel 0.1%—Ligand Pharmaceuticals), DAUNOXOME® (daunorubicin citrate liposome—NeXstar), and TAXOL® (paclitaxel for Injection—Bristol Myers Squibb Co. Pharmaceutical Research Institute).

Leukemia regimens can include combinations with BUSULFEX® (busulfan—Orphan Medical Inc); CAMPATH® (alemtuzumab—from Millennium and ILEX Partners, LP); Daunorubicin HCL (Bedford Laboratories, Div. Ben Venue Laboratories, Inc.); Elliotts B Solution (calcium chloride, dextrose, magnesium sulfate, potassium chloride, sodium bicarbonate, sodium chloride, sodium phosphate, dibasic) for injection sponsored by Orphan Medical Incorporated; GLEEVEC® (imatinib mesylate) from Novartis Pharmaceuticals Corporation; NEUPOGEN® (filgrastim) by Amgen, Inc.; MYLOTARG® (gemtuzumab ozogamicin) for injection available from Wyeth; and TRISENOX® (arsenic trioxide) from Cell Therapeutics, Inc.

Lung cancer regimens include combinations of agents of the present invention and ETHYOL® (amifostine—Alza); ETOPOPHOS(® (etoposide phosphate—Bristol-Myers Squibb); GEMZAR® (gemcitabine HCL for injection—Eli Lilly & Co.); HYCAMTIN® (topotecan hydrochloride for injection—GlaxoSmithKline); TAXOL® (paclitaxel for Injection—Bristol Myers Squibb Co. Pharmaceutical Research Institute); TAXOTERE® (docetaxel—available from Aventis Pharmaceuticals).

Combination treatments for lymphoma, such as meningeal leukemia or lymphocytic lymphoma, may include Elliotts B Solution (calcium chloride, dextrose, magnesium sulfate, potassium chloride, sodium bicarbonate, sodium chloride, sodium phosphate, and dibasic for injection—Orphan Medical Incorporated) in mixes with methotrexate sodium and/or cytarabine for intrathecal administration. Also useful are Intron A (interferon alfa-2a—Schering Corp.); RITUXAN® (rituximab) sponsored by Genentech, Inc.; ONTAK® (denileukindiftitox) marketed by Ligand Pharmaceuticals and manufactured by Seragen, Inc. for the treatment of persistent or recurrent cutaneous T-cell lymphoma (CTCL), a rare slow-growing form of non-Hodgkin's lymphoma, in which malignant cells express the CD25 component of the IL-2 receptor. The compounds of this invention may also be used in regimens with TARGRETIN® (bexarotene) capsules from Ligand Pharmaceuticals Inc. for treatment of cutaneous manifestations of cutaneous T-cell lymphoma, particularly in patients who are refractory to at least one prior systemic therapy, or with UVADEX® (methoxsalen sterile solution, 20 mcg/mL) available from Therakos, Inc. for palliative treatment of skin manifestations of cutaneous T-cell lymphoma that have been unresponsive to other treatments.

In combinations for the treatment or inhibition of melanoma, the compounds may be combined in regimens with PROLEUKIN® (aldesleukin) from Chiron Corporation, particularly for treatment of adults with metastatic melanoma and for metastatic renal cell carcinoma patients.

The compounds herein may be used in regimens with DepoCyt® (cytarabine liposomal injection, 10 mg/mL) by DepoTech Corporation for treatment of lymphomatous meningitis or other forms of neoplastic meningitis associated with solid tumors, lymphoma or leukemia.

DOSTINEX® (cabergoline) Tablets from Pharmacia & Upjohn Company may be combined with compounds herein for the treatment of hyperprolactinemic disorders, either idiopathic or due to pituitary adenomas.

For inhibition or treatment of ovarian cancers, the compound herein may be combined with DOXIL® (doxorubicin HCL liposome injection) from Alza Corporation; HYCAMTIN® (topotecan HCL) from SmithKline Beecham;, or TAXOL® (paclitaxel) from Bristol-Myers Squibb Company.

In regimens for pancreatic cancers, combinations herein may include GEMZAR® (gemcitabine HCL) available from Eli Lilly & Co. For prostate cancers, combination can include LUPRON DEPOT® (leuprolide acetate) for Injection sponsored by TAP Holdings Incorporated; NILANDRON® (nilutamide) Tablets sponsored by GH Besselaar Associates Incorporated; NOVANTRONE® (mitoxantrone hydrochloride) for Injection, Immunex Corporation; TRELSTAR DEPOT® (triptorelin pamoate) for injectable suspension from Debio Recherche Pharmaceutique S.A., VIADUR® (leuprolide acetate implant) from Alza Corporation; ZOLADEX® (goserelin acetate implant) by Zeneca Pharmaceuticals, or the Urowave Microwave Thermotherapy System by Dornier Medical Systems, Inc., which is a nonsurgical treatment alternative to transurethral resection of the prostate.

The compounds of this invention may also be used prior to, in conjunction with, or following regimens of chemotherapeutic alkylating agents. Useful alkylating agents include those known in the art including bis(chlorophenyl) amines such as cyclophosphamide, mechloroethamine, chlorambucil or melphalan; nitrosoureas such as carmustine, lomustine, or semustine; aziridines such as thiotepa or triethylenemelamine; alkylsulfonates, such as busulfan; or other alkylation agents, including procarbazine, dacarbazine, hexamethylmelamine, altretamine, and cisplatin.

The compounds of this invention may also be used in pharmaceutical combinations and regimens and other treatment methods for restinosis. The compounds herein may be used with brachytherapy (gamma or beta radiation), sonotherapy, cryotherapy, endothelial cell implantations, or nitric oxide treatments for restinosis. They may also be administered in conjunction with vascular stents used following angioplasty, including biodegradable stents, and drug-coated or other drug-eluting or DNA-coated stents. Examples of compounds which may be used in drug-containing stents include dexamethasone, Actinomycin-D, rapamycin, sirolimus, or paclitaxel.

A further embodiment of this invention comprises a compound of this invention incorporated into or coated onto a vascular stent, which may be accomplished by conventional techniques known in the art. Nonlimiting types of stents which could be modified or coated with compounds herein include the Cook ACHIEVE™ drug-eluting coronary stent (Cook Group Inc.), the Gianturco Rubin stent (Cook Europe, Denmark), the Palmaz-Shatz® Balloon Expandable Stent (Johnson & Johnson), the Guidant ACS Multi-Link (Guidant Corp.), Wiktor® stent (Medtronic—U.S. Pat. No. 4,886,062), the Strecker stent (Boston Scientific), Symphony stent (Boston Scientific), the NIR® Conformer paclitaxel-coated coronary stent (Boston Scientific), the DISA S-FLEX coronary stent (Disa Vascular), the ACS MULTI-LINK® stent (Guidant), and the WALLSTENT® intravascular stents (Schneider, Zurich, Switzerland).

Metallic stents can be coated with compounds of this invention by methods known in the art. The surface can be covalently linked with an organosilane containing amine reactive sites, such as a metal oxide or an organosilane with a vinyl functionality. Then, a biocompatible coating material can be covalently linked to the organosilane. The coating layer containing a compound of this invention, alone or in combination with other pharmacologically active agents, may also be applied with a polymeric precursor divided or dissolved in a polymer solvent or vehicle that can then be cured in situ. The coating may be applied by conventional techniques, such as dipping or spraying. Methods for coating stents are described in WO-96/32907; U.S. Pat. No. 5,607,475; U.S. Pat. No. 5,356,433; U.S. Pat. No. 5,213,898; U.S. Pat. No. 5,049,403; U.S. Pat. No. 4,807,784; U.S. Pat. No. 4,565,740; U.S. Pat. No. 6,361,819; US20020009535 A1; US20010027340 A1; U.S. Pat. No. 5,980,972; and WO0062830 A2.

Antiplatelet drugs which may be used along with compounds of this invention in treating, inhibiting or delaying onset of restinosis, optionally along with drug-eluding stents, are the platelet glycoprotein IIb/IIIa inhibitors, such as abciximab, eptifabatide, Integrelin, lamifiban, and tirofiban. Other useful antiplatelet agents include aspirin, cilostazol, ticlopidine, clopdogrel, sulfinpyrazone, dipyridamole, and Ridogrel.

The compounds of this invention can be formulated and administered in a wide variety of oral and parenteral dosage forms, including transdermal and rectal administration. It will be recognized to those skilled in the art that the following dosage forms may comprise as the active component, a compound of Formula I or a corresponding pharmaceutically acceptable salt or solvate thereof.

A further embodiment of this invention is a pharmaceutical formulation comprising a compound of Formula I together with a pharmaceutically acceptable carrier, diluent, or excipient therefor. For preparing pharmaceutical compositions with the compounds of the present invention, pharmaceutically acceptable carriers can be either a solid or liquid. Solid form preparations include powders, tablets, pills, capsules, cachets, suppositories, and dispensable granules. A solid carrier can be one or more substances which may also act as diluents, flavoring agents, binders, preservatives, tablet disintegrating agents, or an encapsulating material.

In powders, the carrier is a finely divided solid such as talc or starch in a mixture with the finely divided active component. In tablets, the active component is mixed with the carrier having the necessary binding properties in suitable proportions and compacted in the shape and size desired.

The formulations of this invention preferably contain from about 5% to about 70% or more of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. A preferred form for oral use are capsules, which include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogenously therein, as by stirring. The molten homogenous mixture is then poured into convenient size molds, allowed to cool, and thereby to solidify.

Liquid form preparations include solutions, suspensions, and emulsions such as water or water/propylene glycol solutions. For parenteral injection, liquid preparations can be formulated in solution in aqueous polyethylene glycol solution, isotonic saline, 5% aqueous glucose, and the like. Aqueous solutions suitable for oral use can be prepared by dissolving the active component in water and adding suitable colorants, flavors, and stabilizing and thickening agents as desired. Aqueous suspensions suitable for oral use can be made by dispersing the finely divided active component in water and mixing with a viscous material, such as natural or synthetic gums, resins, methylcellulose, sodium carboxymethylcellulose, or other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Waxes, polymers, microparticles, and the like can be used to prepare sustained-release dosage forms. Also, osmotic pumps can be employed to deliver the active compound uniformly over a prolonged period.

The pharmaceutical preparations of the invention are preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

A pharmaceutically or therapeutically effective amount or dose of a compound of this invention will generally be from about 1 mg to about 100 mg/kg of body weight per day. Typical adult doses will be about 50 mg to about 800 mg/day. The quantity of active component in a unit dose preparation may be varied or adjusted from about 0.1 mg to about 500 mg, preferably about 0.5 to 100 mg according to the particular application and the potency of the active component. The composition can, if desired, also contain other compatible therapeutic agents. A subject in need of treatment with a compound of this invention is administered a dosage of about 1 to about 500 mg/day, either singly or in multiple doses over a 24-hour period.

The compounds of the present invention are capable of binding to and inhibiting the activity of proteins having the ability to phosphorylate other proteins, such as cdks, PDGFr, FGFr, c-Src, and EGFr-FL. Cdks form complexes with cyclins, and these complexes phosphorylate key proteins allowing cells to proceed through the cell cycle (Meijer L., *Progress in Cell Cycle Research*, 1995;1:351–363). The compounds of this invention inhibit this phosphorylation and therefore can be used as antiproliferative agents for the treatment of cancer and/or restenosis and other proliferative diseases.

A pharmaceutically or therapeutically effective amount or dose of a compound of this invention will be understood to be an amount which will provide inhibition of the activity of the proteins and phosphorylation mechanisms described herein. A pharmaceutically or therapeutically effective amount or dose of a compound of this invention will also be understood to be an amount sufficient to provide a preventative, inhibitory, ameliorating or diminishing effect on the maladies described herein, their symptoms or physiological origins.

Because of their inhibitory activity against cdks and other kinases, the compounds of the present invention are also useful research tools for studying the mechanism of action of those kinases, both in vitro and in vivo.

While the forms of the invention herein constitute presently preferred embodiments, many others are possible. It is not intended herein to mention all of the possible equivalent forms or ramifications of the invention. It is understood that the terms used herein are merely descriptive rather than limiting, and those skilled in the art will realize that various changes may be made without departing from the spirit or scope of the invention.

The invention compounds can be formulated in conventional manners to provide convenient dosage forms for delivery to mammals by various routes, including oral, parenteral (i.e., subcutaneous, intravenous, and intramuscular), transdermal, e.g., slow release skin patch or cream, as well as by slow release delivery devices such as osmotic pumps, suppositories, and buccal seals. The following non-limiting examples further illustrate how the compounds of this invention may be readily formulated.

| 50 mg Tablet Formulation | | | |
|---|---|---|---|
| Per Tablet (g) | | | Per 10,000 Tablets (g) |
| 0.050 | 1-Cyclopentyl-3-(2,6-difluoro-3,5-dimethoxy-phenyl)-7-(4-dimethylamino-butylamino)-1H-pyrimido[4,5-d]pyrimidin-2-one | | 500 |
| 0.080 | Lactose | | 800 |
| 0.010 | Corn starch (for mix) | | 100 |
| 0.008 | Corn starch (for paste) | | 80 |
| 0.148 | | | 1480 |
| 0.002 | Magnesium stearate (1%) | | 20 |
| 0.150 | | | 1500 |

The active agent of this invention, lactose, and corn starch (for mix) are blended to uniformity. The corn starch (for paste) is suspended in 600 mL of water and heated with stirring to form a paste. This paste is used to granulate the mixed powders. The wet granules are passed through a No. 8 hand screen and dried at 80° C. The dry granules are then passed through a No. 16 screen. The mixture is lubricated with 1% magnesium stearate and compressed into tablets in a conventional tableting machine. The tablets are useful for treating cancers such as breast, prostate, lung, ovarian, colon, pancreatic, melanoma, esophageal, brain, Kaposi's sarcoma, and lymphomas.

| Preparation of Oral Suspension | |
|---|---|
| Ingredient | Amount |
| 1-Cyclopentyl-3-(2,6-difluoro-3,5-dimethoxy-phenyl)-7-(4-dimethylamino-butylamino)-1H-pyrimido[4,5-d]pyrimidin-2-one | 500 mg |
| Sorbitol solution (70% N.F.) | 40 mL |
| Sodium benzoate | 150 mg |
| Saccharin | 10 mg |
| Cherry flavor | 50 mg |
| Distilled water qs | 100 mL |

The sorbitol solution is added to 40 mL of distilled water, and the pyrido pyrimidine is suspended therein. The saccharin, sodium benzoate, and flavoring are added and dissolved. The volume is adjusted to 100 mL with distilled water. Each milliliter of syrup contains 5 mg of invention compound.

Preparation of Parenteral Solution

In a solution of 700 mL of propylene glycol and 200 mL of water for injection is suspended 20.0 g of 1-cyclopentyl-3-(2,6-difluoro-3,5-dimethoxy-phenyl)-7-(4-dimethylamino-butylamino)-1H-pyrimido[4,5-d]pyrimidin-2-one with stirring. After suspension is complete, the pH is adjusted to 5.5 with hydrochloric acid, and the volume is made up to 1000 mL with water for injection. The formulation is sterilized, filled into 5.0 mL ampoules, each containing 2.0 mL (representing 40 mg of invention compound) and sealed under nitrogen.

Suppositories

A mixture of 400 mg of 1-cyclopentyl-3-(2,6-difluoro-3,5-dimethoxy-phenyl)-7-(4-dimethylamino-butylamino)-1H-pyrimido[4,5-d]pyrimidin-2-one, and 600 mg of theobroma oil is stirred at 60° C. to uniformity. The mixture is cooled and allowed to harden in a tapered mold to provide a 1 g suppository.

Slow Release Formulation

Five hundred milligrams of 1-cyclopentyl-3-(2,6-difluoro-3,5-dimethoxy-phenyl)-7-(4-dimethylamino-butylamino)-1H-pyrimido[4,5-d]pyrimidin-2-one is converted to a hydrochloride salt and placed into an Oros osmotic pump for controlled release for treatment of atherosclerosis.

Skin Patch Formulation

Fifty milligrams of 1-cyclopentyl-3-(2,6-difluoro-3,5-dimethoxy-phenyl)-7-(4-dimethylamino-butylamino)-1H-pyrimido[4,5-d]pyrimidin-2-one is admixed with 50 mg of propylene glycol monolaurate in a polydimethylsiloxane adhesive. The mixture is layered onto an elastic film made with an adhesive formulation of polybutene, polyisobutylene, and propylene glycol monolaurate. The layers are placed between 2 layers of polyurethane film. A release liner is attached to the adhesive surface, and is removed prior to application to a skin surface. The propylene glycol monolaurate serves as a permeation-enhancing agent.

What is claimed is:

1. A compound of the formula:

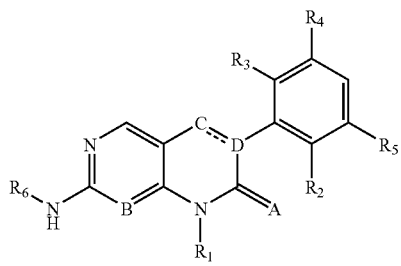

wherein:
- A is O, NH$_2$, NH(C$_1$–C$_6$ alkyl), N(C$_1$–C$_6$ alkyl)$_2$, or —NHC(O)—NHR$_{12}$;
- R$_{12}$ is C$_1$–C$_6$ straight or branched chain alkyl, or —(CH$_2$)n-C$_3$–C$_8$ cycloalkyl ring; n is an integer of from 1 to 3;
- B is N, C is CH, D is N,
- R$_1$ is selected from the group of C$_1$–C$_6$ straight or branched chain alkyl, optionally substituted by —COOH, or;
  a) a phenyl, benzyl or C$_3$–C$_8$ cycloalkyl ring, or —CH$_2$—C$_3$–C$_8$ cycloalkyl ring, with the phenyl, benzyl or cycloalkyl rings being optionally substituted by 1 or 2 COOH or —CH$_2$—COOH groups; or
  b) a piperidine or piperazine moiety selected from group of:

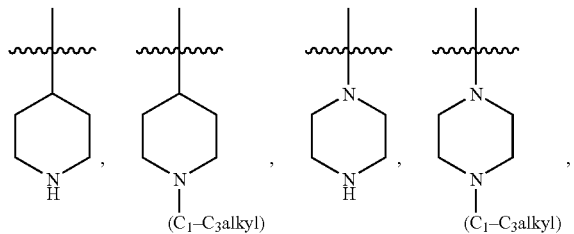

the rings of the piperidine or piperazine moieties being optionally substituted by 1 or 2 COOH or —CH$_2$—COOH groups; or
  c) a tetrahydropyran or morpholine moiety of the formulae:

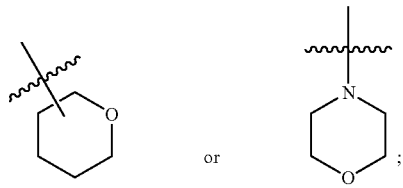

- R$_2$ is H, Cl or F;
- R$_3$ is H, Cl or F, with the proviso that at least one of R$_2$ or R$_3$ is F;
- R$_4$ is H, OH, —OCH$_3$, or —OCH$_2$CH$_3$, with the proviso that, if R$_4$ is H, R$_2$ and R$_3$ are not H;
- R$_5$ is —OCH$_3$, or —OCH$_2$CH$_3$;
- R$_6$ is selected from the group of H, —(C$_1$–C$_5$ alkyl)-NH$_2$, —(C$_1$–C$_5$ alkyl)-NH—(C$_1$–C$_3$ alkyl)-R$_{11}$, —(C$_1$–C$_5$ alkyl)-N—(C$_1$–C$_3$ alkyl-R$_{11}$)$_2$, —O—(C$_1$–C$_5$ alkyl)-NH$_2$, —O—(C$_1$–C$_5$ alkyl)-NH—(C$_1$–C$_3$ alkyl)-R$_{11}$, —O—(C$_1$–C$_5$ alkyl)-N—(C$_1$–C$_3$ alkyl-R$_{11}$)$_2$, —CH(CH$_2$OH)$_2$, —(C$_1$–C$_3$ alkyl)-(CH$_2$OH)$_2$, —(C$_1$–C$_3$ alkyl)-O—(C$_1$–C$_3$ alkyl)-R$_{11}$, —(C$_1$-C$_3$ alkyl)-O—(C$_1$–C$_3$ alkyl)-NH$_2$, —(C$_1$–C$_3$ alkyl)-O—(C$_1$–C$_3$ alkyl)-NH—(C$_1$–C$_3$ alkyl)-R$_{11}$, —(C$_1$–C$_3$ alkyl)-O—(C$_1$–C$_3$ alkyl)-N(C$_1$–C$_3$ alkyl-R$_{11}$)$_2$, phenyl substituted by one or two groups selected from NH$_2$, —N(C$_1$–C$_3$ alkyl), —N(C$_1$–C$_3$ alkyl)$_2$, CN or —(C$_1$–C$_3$ alkyl)-tetrazole, or C$_1$–C$_6$ alkyl,

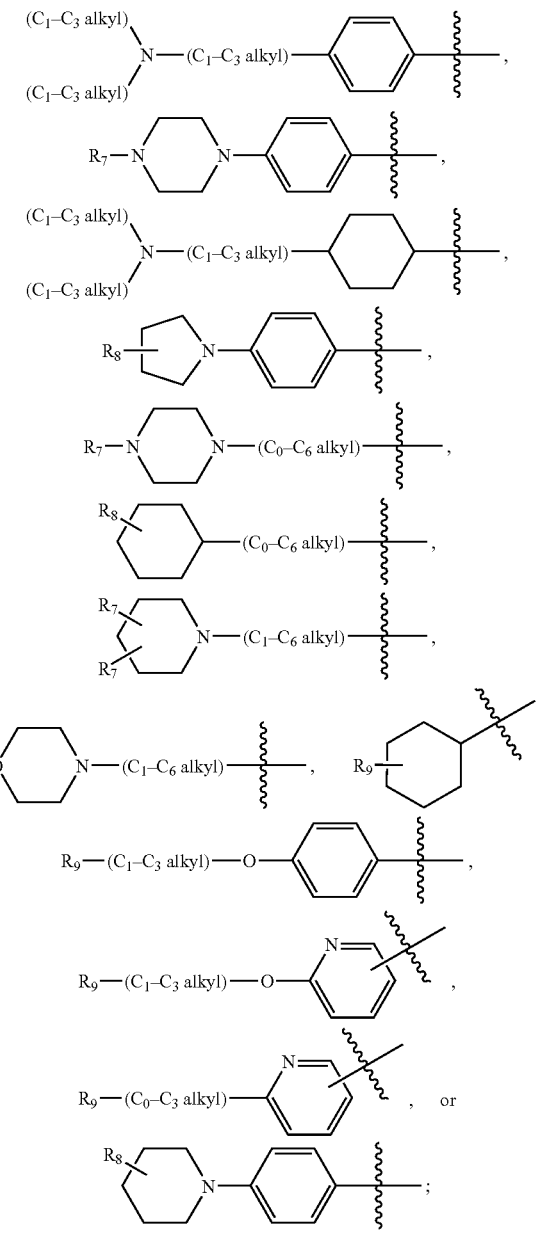

with each of the alkyl chains of any group in this R$_4$ definition being optionally substituted by from 1 to 4 OH groups;

R$_7$ in each instance is independently selected from H, —NH$_2$, NH(C$_1$–C$_3$ alkyl), N(C$_1$–C$_3$ alkyl)$_2$, or C$_1$–C$_3$ alkyl;

$R_8$ is H, OH or $C_1$–$C_3$ alkyl;

$R_9$ is H, OH, —$NH_2$, NH($C_1$–$C_3$ alkyl), or N($C_1$–$C_3$ alkyl)$_2$;

$R_{10}$ is H or $C_1$–$C_3$ alkyl;

$R_{11}$ is H, CN, OH, $NH_2$, F, or $CF_3$;

or a pharmaceutically acceptable salt or ester form thereof.

2. A compound of claim 1 selected from the group of:

1-Cyclopentyl-7-(4-diethylamino-butylamino)-3-(2,6-difluoro-3-hydroxy-5-methoxy phenyl)-3,4-dihydro -1H -pyrimido[4,5-d]pyrimidin-2-one;

1-Cyclopentyl-7-(4-diethylamino-butylamino)-3-(2,6-difluoro-3,5-dimethoxy-phenyl)-3,4-dihydro-1H-pyrimido [4,5-d]pyrimidin-2-one;

(S,S)-1-Cyclopentyl-3-(2,6-difluoro-3,5-dimethoxy-phenyl)-7-[(5-hydroxymethyl-2-phenyl-[1,3]dioxolan-4-ylmethyl)-amino]-3,4-dihydro-1H-pyrimido[4,5-d]pyrimidin-2-one;

(S,S)-1-Cyclopentyl-3-(2,6-difluoro-3,5-dimethoxy-phenyl)-7-(2,3,4-trihydroxy-butylamino)-3,4-dihydro-1H-pyrimido[4,5-d]pyrimidin-2-one; or 1-Cyclopentyl-3-(2,6-difluoro-3,5-dimethoxy-phenyl)-7-(4-hydroxy-cyclohexylamino)-3,4-dihydro-1H-pyrimido[4,5-d]pyrimidin-2-one;

1-Cyclopentyl-3-(2,6-difluoro-3,5-dimethoxy-phenyl)-7-(2-hydroxy-1-hydroxymethyl-ethylamino)-3,4-dihydro-1H-pyrimido[4,5-d]pyrimidin-2-one;

7-(3-Amino-2-hydroxy-propylamino)-1-cyclopentyl-3-(2,6-difluoro-3,5-dimethoxy-phenyl)-3,4-dihydro-1H-pyrimido[4,5-d]pyrimidin-2-one;

1-Cyclopentyl-3-(2,6-difluoro-3,5-dimethoxy-phenyl)-7-[2-(2-hydroxy-ethoxy)-ethylamino]-3,4-dihydro-1H-pyrimido[4,5-d]pyrimidin-2-one;

1-Cyclopropyl-7-(4-diethylamino-butylamino)-3-(2,6-difluoro-3,5-dimethoxy-phenyl)-3,4-dihydro-1H-pyrimido[4,5-d]pyrimidin-2-one; or 7-(4-Diethylamino-butylamino)-3-(2,6-difluoro-3,5-dimethoxy-phenyl)-1-ethyl-3,4-dihydro-1H-pyrimido[4,5-d]pyrimidin-2-one;

or a pharmaceutically acceptable salt or ester form thereof.

3. A compound of claim 1 selected from the group of:

3-(2,6-Difluoro-3,5-dimethoxy-phenyl)-1-ethyl-7-(2-hydroxy-1-hydroxymethyl-ethylamino)-3,4-dihydro-1H-pyrimido[4,5-d]pyrimidin-2-one;

3-(2,6-Difluoro-3,5-dimethoxy-phenyl)-1-ethyl-7-(4-hydroxy-cyclohexylamino)-3,4-dihydro-1H-pyrimido[4,5-d]pyrimidin-2-one;

1-Cyclopentyl-3-(2,6-difluoro-3,5-dimethoxy-phenyl)-7-(2,3-dihydroxy-butylamino)-3,4-dihydro-1H-pyrimido[4,5-d]pyrimidin-2-one 1-Cyclopentyl-3-(2,6-difluoro-3,5-dimethoxy-phenyl)-7-(2,3-dihydroxy-propylamino)-3,4-dihydro-1H-pyrimido[4,5-d]pyrimidin-2-one;

7-(4-Amino-2,3-dihydroxy-butylamino)-1-cyclopentyl-3-(2,6-difluoro-3,5-dimethoxy-phenyl)-3,4-dihydro-1H-pyrimido[4,5-d]pyrimidin-2-one;

1-Cyclopentyl-3-(2-fluoro-3,5-dimethoxy-phenyl)-7-([S,S]-2,3,4-trihydroxy-butylamino)-3,4-dihydro-1H-pyrimido[4,5-d]pyrimidin-2-one;

3-(2,6-Difluoro-3,5-dimethoxy-phenyl)-1-ethyl-7-[2-(2-hydroxy-ethoxy)-ethylamino]-3,4-dihydro-1H-pyrimido[4,5-d]pyrimidin-2-one;

7-(4-Amino-2,3-dihydroxy-butylamino)-3-(2,6-difluoro-3,5-dimethoxy-phenyl)-1-ethyl-3,4-dihydro-1H-pyrimido[4,5-d]pyrimidin-2-one;

7-{3-[Bis-(2-hydroxy-ethyl)-amino]-propylamino}-3-(2,6-difluoro-3,5-dimethoxy-phenyl)-1-ethyl-3,4-dihydro-1H-pyrimido[4,5-d]pyrimidin-2-one; or 1-Cyclopentyl-3-(2,6-difluoro-3,5-dimethoxy-phenyl)-7-(2,3-dihydroxy-propylamino)-3,4-dihydro-1H-pyrimido[4,5-d]pyrimidin-2-one;

or a pharmaceutically acceptable salt or ester form thereof.

4. A compound of claim 1 selected from the group of:

3-(2,6-Difluoro-3,5-dimethoxy-phenyl)-7-(2,3-dihydroxy-butylamino)-1-ethyl-3,4-dihydro-1H-pyrimido[4,5-d]pyrimidin-2-one;

Ethyl-4-[3-(2,6-difluoro-3,5-dimethoxy-phenyl)-7-methylamino-2-oxo-3,4-dihydro-2H-pyrimido[4,5-d]pyrimidin-1-yl]-cyclohexanecarboxylate;

4-[3-(2,6-Difluoro-3,5-dimethoxy-phenyl)-7-methylamino-2-oxo-3,4-dihydro-2H-pyrimido[4,5-d]pyrimidin-1-yl]-cyclohexanecarboxylic acid;

7-Amino-3-(2,6-difluoro-3,5-dimethoxy-phenyl)-1-piperidin-4-yl-3,4-dihydro-1H-pyrimido[4,5-d]pyrimidin-2-one; compound with trifluoroacetic acid; or 1-Cyclopentyl-3-(2-fluoro-3,5-dimethoxy-phenyl)-7-(2-hydroxy-1-hydroxymethyl-ethylamino)-3,4-dihydro-1H-pyrimido[4,5-d]pyrimidin-2-one;

1-Ethyl-3-(2-fluoro-3,5-dimethoxy-phenyl)-7-(4-hydroxy-butylamino)-3,4-dihydro-1H-pyrimido[4,5-d]pyrimidin-2-one;

(S)-1-Cyclopentyl-7-(2,3-dihydroxy-propylamino)-3-(2-fluoro-3,5-dimethoxy-phenyl)-3,4-dihydro-1H-pyrimido[4,5-d]pyrimidin-2-one;

1-Ethyl-3-(2-fluoro-3,5-dimethoxy-phenyl)-7-(4-hydroxy-cyclohexylamino)-3,4-dihydro-1H-pyrimido[4,5-d]pyrimidin-2-one;

4-[3-(2,6-Difluoro-3,5-dimethoxy-phenyl)-7-methylamino-2-oxo-3,4-dihydro-2H-pyrimido[4,5-d]pyrimidin-1-yl]-piperidine-1-carboxylic acid; or 3-(2,6-Difluoro-3,5-dimethoxy-phenyl)-7-methylamino-1-piperidin-4-yl-3,4-dihydro-1H-pyrimido[4,5-d]pyrimidin-2-one;

3-(2,6-Difluoro-3,5-dimethoxy-phenyl)-7-(2,3-dihydroxy-propylamino)-1-ethyl-3,4-dihydro-1H-pyrimido[4,5-d]pyrimidin-2-one;

1-Cyclopentyl-7-(4-diethylamino-butylamino)-3-(3-ethoxy-2,6-difluoro-phenyl)-3,4-dihydro-1H-pyrimido[4,5-d]pyrimidin-2-one;

(R)-1-Cyclopentyl-7-(2,3-dihydroxy-propylamino)-3-(2-fluoro-3,5-dimethoxy-phenyl)-3,4-dihydro-1H-pyrimido[4,5-d]pyrimidin-2-one;

1-Ethyl-3-(2-fluoro-3,5-dimethoxy-phenyl)-7-[2-(2-hydroxy-ethoxy)-ethylamino]-3,4-dihydro-1H-pyrimido[4,5-d]pyrimidin-2-one; or 1-Cyclopentyl-3-(2-fluoro-3,5-dimethoxy-phenyl)-7-(trans-4-hydroxy-cyclohexyl-amino)-3,4-dihydro-1H-pyrimido[4,5-d]pyrimidin-2-one;

or a pharmaceutically acceptable salt or ester form thereof.

5. A pharmaceutical composition comprising a pharmaceutically effective amount of a compound of claim 1 and a pharmaceutically acceptable carrier.

6. A compound of the formula:

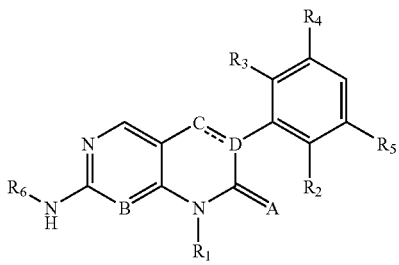

wherein:
A is O, NH$_2$, NH(C$_1$—C$_6$ alkyl), N(C$_1$—C$_6$alkyl)$_2$, or —NHC(O)NHR$_{12}$;
R$_{12}$ is C$_1$—C$_6$ straight or branched chain alkyl, or —(CH$_2$)n—C$_3$—C$_8$ cycloalkyl ring; n is an integer of from 1 to 3;
B is N, C is CH, D is N,
R$_1$ is selected from the group of C$_1$—C$_6$ straight or branched chain alkyl, optionally substituted by —COOH, or;
a) a phenyl, benzyl or C$_3$—C$_8$ cycloalkyl ring, or —CH$_2$—C$_3$—C$_8$ cycloalkyl ring, with the phenyl, benzyl or cycloalkyl rings being optionally substituted by 1 or 2 COOH or —CH$_2$—COOH groups; or
b) a piperidine or piperazine moiety selected from group of:

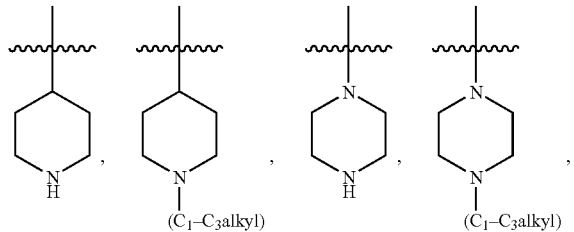

the rings of the piperidine or piperazine moieties being optionally substituted by 1 or 2 COOH or —CH2—COOH groups; or
c) a tetrahydropyran or morpholine moiety of the formulae:

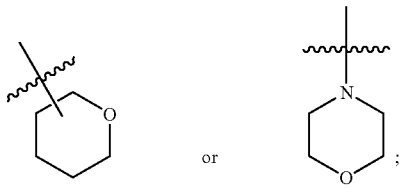

R$_2$ is H, Cl or F;
R$_3$ is H, Cl or F, with the proviso that at least one of R$_2$ or R$_3$ is F;
R$_4$ is H, OH, —OCH$_3$, or —OCH$_2$CH$_3$, with the proviso that, if R$_4$ is H, R$_2$ and R$_3$ are not H;
R$_5$ is —OCH$_3$, or —OCH$_2$CH$_3$;
R$_6$ is selected from the group of H, —(C$_1$—C$_5$ alkyl)—NH$_2$, —(C$_1$—C$_5$ alkyl)—NH—(C$_1$—C$_3$ alkyl)—R$_{11}$, —(C$_1$—C$_5$ alkyl)—N—(C$_1$—C$_3$ alkyl—R$_{11}$)$_2$, —O—(C$_1$—C$_5$ alkyl)—NH$_2$, —O—(C$_1$—C$_5$ alkyl)—NH—(C$_1$—C$_3$ alkyl)— R$_{11}$, —O—(C$_1$—C$_5$ alkyl)—N—(C$_1$—C$_3$ alkyl$_{R11}$)$_2$, —CH(CH$_2$OH)$_2$, —(C$_1$—C$_3$ alkyl (CH$_2$OH)$_2$, —(C$_1$—C$_3$ alkyl)—O—(C$_1$—C$_3$ alkyl)—R$_{11}$, —(C$_1$—C$_3$ alkyl)—O—(C$_1$—C$_3$ alkyl)— NH$_2$, —(C$_1$—C$_3$ alkyl)—O—(C$_1$—C$_3$ alkyl)—NH—(C$_1$—C$_3$ alkyl)—R$_{11}$, —(C$_1$—C$_3$ alkyl)—O—(C$_1$—C$_3$ alkyl)—N(C$_1$—C$_3$ alkyl—R$_{11}$)$_2$, phenyl substituted by one or two groups selected from NH$_2$, —N(C$_1$—C$_3$ alkyl), —N(C$_1$—C$_3$ alkyl)$_2$, CN or —(C$_1$—C$_3$ alkyl)—tetrazole, or C$_1$—C$_6$ alkyl,

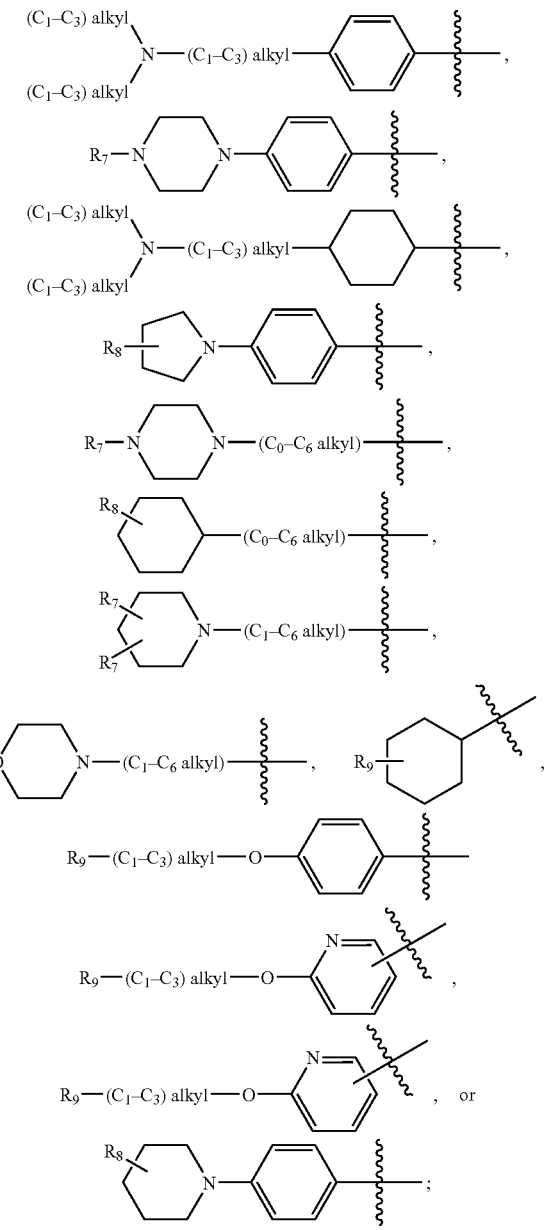

with each of the alkyl chains of any group in this R$_4$ definition being optionally substituted by from 1 to 4 OH groups;
R$_7$ in each instance is independently selected from H, —NH$_2$, NH(C$_1$—C$_3$ alkyl), N(C$_1$—C$_3$ alkyl)$_2$, or C$_1$—C$_3$ alkyl;

R$_8$ is H, OH or C$_1$—C$_3$ alkyl;
R$_9$ is H, OH, —NH$_2$, NH(C$_1$—C$_3$ alkyl), or N(C$_1$—C$_3$ alkyl)$_2$;
R$_{10}$ is H or C$_1$—C$_3$ alkyl;
R$_{11}$ is H, CN, OH, NH$_2$, F, or CF$_3$, or a pharmaceutically acceptable salt thereof.

7. A compound of claim 6 selected from the group of:
1-Cyclopentyl-7-(4-diethylamino-butylamino)-3-(2,6-difluoro-3-hydroxy-5-methoxy phenyl)-3,4-dihydro-1H-pyrimido[4,5-d]pyrimidin-2-one;
1-Cyclopentyl--7-(4-diethylamino-butylamino)-3-(2,6-difluoro-3,5-dimethoxy-phenyl)-3,4-dihydro-1H-pyrimido[4,5-d]pyrimidin-2-one;
(S,S)-1-Cyclopentyl-3-(2,6-difluoro-3,5-dimethoxy-phenyl)-7-[(5--hydroxymethyl-2-phenyl-[1,3]dioxolan-4-ylmethyl)-amino]-3,4-dihydro-1H-pyrimido[4,5-d]pyrimidin-2-one;
(S,S)-1-Cyclopentyl-3-(2,6-difluoro-3,5-dimethoxy-phenyl)-7-(2,3,4-trihydroxy-butylamino)-3,4-dihydro-1H-pyrimido[4,5-d]pyrimidin-2-one;
1-Cyclopentyl-3-(2,6-difluoro-3,5-dimethoxy-phenyl)-7-(4hydroxy-cyclohexyl-amino)-3,4-dihydro-1H-pyrimido[4,5-d]pyrimidin-2-one;
1-Cyclopentyl-3-(2,6-difluoro-3,5-dimethoxy-phenyl)-7-(2-hydroxy-1-hydroxy-methyl-ethylamino)-3,4-dihydro-1H-pyrimido[4,5-d]pyrimidin-2-one;
7-(3-Amino-hydroxy-propylamino)-1-cyclopentyl-3-(2,6-difluoro-3,5-dimethoxy-phenyl)-3,4-dihydro-1H-pyrimido[4,5-d]pyrimidin-2-one;
1-Cyclopentyl-3-(2,6-difluoro-3,5-dimethoxy-phenyl)-7-[2-(2-hydroxy-ethoxy)-ethylamino]-3,4-dihydro-1H-pyrimido[4,5-d]pyrimidin-2-one;
1-Cyclopropyl-7-(4-diethylamino-butylamino)-3-(2,6-difluoro-3,5-dimethoxy-phenyl)-3,4-dihydro-1H-pyrimido[4,5-d]pyrimidin-2-one; or 7-(4-Diethylamino-butylamino)-3-(2,6-difluoro-3,5-dimethoxy-phenyl)-1-ethyl-3,4-dihydro-1H-pyrimido[4,5-d]pyrimidin-2-one; or a pharmaceutically acceptable salt thereof.

8. A compound of claim 6 selected from the group of:
3-(2,6-Difluoro-3,5-dimethoxy-phenyl)-1-ethyl-7-(2-hydroxy-1-hydroxymethyl-ethylamino)-3,4-dihydro-1H-pyrimido[4,5-d]pyrimidin-2-one;
3-(2,6-Difluoro-3,5-dimethoxy-phenyl)-1-ethyl-7-(4-hydroxy-cyclohexylamino)-3,4-dihydro-1H-pyrimido[4,5-d]pyrimidin-2-one;
1-Cyclopentyl-3-(2,6-difluoro-3,5-dimethoxyphenyl)-7-(2,3-dihydroxybutylamino)-3,4-dihydro-1H-pyrimido[4,5-d]pyrimidin-2-one;
1-Cyclopentyl-3-(2,6-difluoro-3,5-dimethoxy-phenyl)-7-(2,3-dihydroxypropyl-amino)-3,4-dihydro-1H-pyrimido[4,5-]pyrimidin-2-one;
7-(4-Amino-2,3-dihydroxy-butylamino)-1-cyclopentyl-3-(2,6-difluoro-3,5-dimethoxy-phenyl)-3,4-dihydro-1H-pyrimido[4,5-d]pyrimidin-2-one;
1-Cyclopentyl-3-(2-fluoro-3,5-dimethoxy-phenyl)-7-([S,S]-2,3,4-trihydroxy-butylamino)-3,4-dihydro-1H-pyrimido[4,5-d]pyrimidin-2-one;
3-(2,6-Difluoro-3,5-dimethoxy-phenyl)-1-ethyl-7-[2-(2-hydroxyethoxy)-ethyl-amino]-3,4-dihydro-1H-pyrimido[4,5-d]pyrimidin-2-one;
7-(4-Amino-2,3-dihydroxy-butylamino)-3-(2,6-difluoro-3,5-dimethoxyphenyl)-1-ethyl-3,4-dihydro-1H-pyrimido[4,5-d]pyrimidin-2-one;
7-(3-[Bis-(2-hydroxy-ethyl)-amino]-propylamino)-3-(2,6-difluoro-3,5-dimethoxy-phenyl)-1-ethyl-3,4-dihydro-1H-pyrimido[4,5-d]pyrimidin-2-one;
1-Cyclopentyl-3-(2,6-difluoro-3,5-dimethoxy-phenyl)-7-(2,3-dihydroxypropyl-amino)-3,4-dihydro-1H-pyrimido[4,5-d]pyrimidin-2-one;
or a pharmaceutically acceptable salt thereof.

9. A compound of claim 6 selected from the group of:
3-(2,6-Difluoro-3,5-dimethoxy-phenyl)-7-(2,3-dihydroxy-butylamino)-1-ethyl-3,4- dihydro-1H-pyrimido[4,5-d]pyrimidin-2-one;
Ethyl-4-[3-(2,6-difluoro-3,5-dimethoxy-phenyl)-7-methylamino-2-oxo-3,4-dihydro-2H-pyrimido[4,5-d]pyrimidin-1-yl-cyclohexanecarboxylate;
4-[3-(2,6-Difluoro-3,5-dimethoxy-phenyl)-7-methylamino-2-oxo-3,4-dihydro-2H-pyrimido[4,5-d]pyrimidin-1-yl-cyclohexanecarboxylic acid;
7-Amino-3-(2,6-difluoro-3,5-dimethoxy-phenyl)-1-piperidin-4-yl-3,4-dihydro-1H-pyrimido[4,5-d]pyrimidin-2-one; compound with trifluoroacetic acid;
1-Cyclopentyl-3-(2-fluoro-3,5-dimethoxyphenyl)-7-(2-hydroxy-1-hydroxymethyl-ethylamino)-3,4-dihydro-1H-pyrimido[4,5-d]pyrimidin-2-one;
1-Ethyl-3-(2-fluoro-3,5-dimethoxyphenyl)-7-(4-hydroxy-butylamino)-3,4-dihydro-1H-pyrimido[4,5-d]pyrimidin-2-one;
(S)-1-Cyclopentyl-7-(2,3-dihydroxypropylamino)-3-(2-fluoro-3,5-dimethoxy-phenyl)-3,4-dihydro-1H-pyrimido[4,5-d]pyrimidin-2-one;
1-Ethyl-3-(2-fluoro-3,5-dimethoxypheynl)-7-(4-hydroxy-cyclohexylamino)3,4-dihydro-1H-pyrimido[4,5-d]pyrimidin-2-one;
4-[3-(2,6-Difluoro-3,5-dimethoxyphenyl)-7-methylamino-2-oxo-3,4-dihydro-2H-pyrimido[4,5-d]pyrimidin-1-yl-piperidine-1-carboxylic acid;
3-(2,6-Difluoro-3,5-dimethoxy-phenyl)-7-methylamino-1-piperidin-4-yl-3,4-dihydro-1H-pyrimido[4,5-d]pyrimidin-2-one;
3-(2,6-Difluoro-3,5-dimethoxy-phenyl)-7-(2,3-dihydroxy-propylamino)-1-ethyl-3,4-dihydro-1H-pyrimido[4,5-d]pyrimidin-2-one;
1-Cyclopentyl-7-(4-diethylamino-butylamino)-3-(3-ethoxy-2,6-difluoro-phenyl)-3,4-dihydro-1H-pyrimido[4,5-d]pyrimidin-2-one;
(R)-1-Cyclopentyl-7-(2,3-dihydroxy-propylamino)-3-(2-fluoro-3,5-dimethoxy-phenyl)-3,4-dihydro-1H-pyrimido[4,5-d]pyrimidin-2-one;
1-Ethyl-3-(2-fluoro-3,5-dimethoxy-phenol)-7-[2-(2-hydroxy-ethoxy)-ethylamino]-3,4-dihydro-1H-pyrimido[4,5-d]pyrimidin-2-one; or
1-Cyclopentyl-3-(2-fluoro-3,5-dimethoxy-phenyl)-7-(trans-4-hydroxycyclohexyl-amino)-3,4-dihydro-1H-pyrimido[4,5-d]pyrimidin-2-one;
or a pharmaceutically acceptable salt thereof.

10. A pharmaceutical composition comprising a pharmaceutically effective amount of a compound of claim 6 or a pharmaceutically acceptable salt thereof, and a pharmaceutically acceptable carrier.

* * * * *